United States Patent
Kawooya et al.

(10) Patent No.: US 12,384,849 B2
(45) Date of Patent: Aug. 12, 2025

(54) BISPECIFIC ANTIBODIES WITH CLEAVABLE C-TERMINAL CHARGE-PAIRED TAGS

(71) Applicant: Amgen Inc., Thousand Oaks, CA (US)

(72) Inventors: John K. Kawooya, Moorpark, CA (US); Alex W. Jacobitz, Thousand Oaks, CA (US); Christopher Mohr, Newbury Park, CA (US); Stephen Smith, Newbury Park, CA (US); Kevin Graham, Thousand Oaks, CA (US); Ray Lieh Yoon Low, Redwood City, CA (US); Oliver Thiel, Lexington, MA (US); Dante Romanini, Sherman Oaks, CA (US); Victoria Wagner, Simi Valley, CA (US); Neeraj J. Agrawal, Natick, MA (US)

(73) Assignee: AMGEN INC., Thousand Oaks, CA (US)

( * ) Notice: Subject to any disclaimer, the term of this patent is extended or adjusted under 35 U.S.C. 154(b) by 1039 days.

(21) Appl. No.: 17/053,728

(22) PCT Filed: May 8, 2019

(86) PCT No.: PCT/US2019/031379
§ 371 (c)(1),
(2) Date: Nov. 6, 2020

(87) PCT Pub. No.: WO2019/217587
PCT Pub. Date: Nov. 14, 2019

(65) Prior Publication Data
US 2022/0089756 A1 Mar. 24, 2022

Related U.S. Application Data

(60) Provisional application No. 62/668,626, filed on May 8, 2018.

(51) Int. Cl.
*C07K 16/28* (2006.01)
*C07K 16/46* (2006.01)

(52) U.S. Cl.
CPC ........ *C07K 16/2875* (2013.01); *C07K 16/468* (2013.01); *C07K 2317/526* (2013.01); *C07K 2319/50* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner | |
| 5,260,203 A | 11/1993 | Ladner | |
| 5,591,828 A | 1/1997 | Bosslet | |
| 5,932,448 A | 8/1999 | Tso | |
| 6,833,441 B2 | 12/2004 | Wang | |
| 7,101,692 B2* | 9/2006 | Schneewind | C12N 9/104 435/193 |
| 7,129,330 B1 | 10/2006 | Little | |
| 7,507,796 B2 | 3/2009 | Little | |
| 2005/0214300 A1* | 9/2005 | Venetsanakos | C07K 16/3092 424/155.1 |
| 2010/0322934 A1 | 12/2010 | Imhof-Jung | |
| 2013/0171095 A1* | 7/2013 | Bernett | C07K 16/22 435/328 |
| 2014/0322218 A1* | 10/2014 | Xiao | C07K 16/468 424/136.1 |
| 2015/0183859 A1* | 7/2015 | Rother | A61P 25/04 536/23.53 |
| 2016/0137720 A1* | 5/2016 | Song | C12N 9/52 435/68.1 |
| 2018/0209983 A1† | 7/2018 | Lafleur | |

FOREIGN PATENT DOCUMENTS

| | | |
|---|---|---|
| WO | 8801649 A1 | 3/1988 |
| WO | 9632478 A1 | 10/1996 |
| WO | 9734631 A1 | 9/1997 |
| WO | 200100814 A1 | 1/2001 |
| WO | 2006106905 A1 | 10/2006 |
| WO | 201134605 A1 | 3/2011 |
| WO | 201734770 A1 | 3/2017 |

OTHER PUBLICATIONS

Carrigan et al., "Site-Directed Mutagenesis," Methods Mol. Biol., pp. 107-124 (2011).
Clancy et al., "Sortase transpeptidases: insights into mechanism, substrate specificity, and inhibition." Biopolymers, 94(4), pp. 385-396 (2010).
Dasgupta et al., "Isopeptide ligation catalyzed by quintessential sortase A: mechanistic cues from cyclic and branched oligomers of indolicidin." J. Biol. Chem., 286(27), pp. 23996-24006 (2011).
Davis et al., "SEEDbodies: fusion proteins based on strand-exchange engineered domain (SEED) CH3 heterodimers in an Fc analogue platform for asymmetric binders or immunofusions and bispecific antibodies," Protein Eng. Des. & Sel. 23:195-202 (2010).
Engler et al., A One Pot, One Step, Precision Cloning Method with High Throughput Capability, PLoS One, 3(11), p. e3647 (2008).
Hollinger et al., ""Diabodies": small bivalent and bispecific antibody fragments," PNAS, 90, pp. 6444-6448 (1993).
International Preliminary Report on Patentability, PCT/US2019/031379, dated Nov. 10, 2020.

(Continued)

*Primary Examiner* — Phuong Huynh
(74) *Attorney, Agent, or Firm* — Megan Thobe

(57) ABSTRACT

The present invention is directed to a CH3-containing molecule comprising (a) a first polypeptide comprising a CH3 domain and a negatively charged domain comprising consecutive negatively charged amino acid residues; and (b) a second polypeptide comprising a CH3 domain and a positively charged domain comprising consecutive positively charged amino acid residues. Also provided are methods for conjugating synthetic molecules to a multi-specific antigen binding molecule.

13 Claims, 40 Drawing Sheets

Specification includes a Sequence Listing.

(56) References Cited

OTHER PUBLICATIONS

International Search Report and Written Opinion of the International Search Authority, PCT/US2019/031379, European Patent Office, dated Jul. 24, 2019.
Jacobitz et al., "Sortase Transpeptidases: Structural Biology and Catalytic Mechanism," Adv. Protein Chem. Struct. Biol., 109, pp. 223-264 (2017).
Levary et al., "Protein-Protein Fusion Catalyzed by Sortase A," J. Najbauer, ed. PLoS One, 6(4), p. e18342 (2011).
Longo et al., Transient mammalian cell transfection with polyethylenimine (PEI). Meth. Enzymol., 529, pp. 227-240 (2013).
Mao et al., "Sortase-mediated protein ligation: a new method for protein engineering," J. Amer. Chem. Soc., 126(9), pp. 2670-2671 (2004).
Marvin et al., "Bispecific antibodies for dual-modality cancer therapy: killing two signaling cascades with one stone," Curr. Opin. Drug Discov. Devel. 9(2):184-193 (2006).
O'Shea et al., Peptide 'Velcro': Design of a heterodimeric coiled coil, Curr. Biol., vol. 3, No. 10 pp. 658-667 (1993).
Parthasarathy et al., "Sortase A as a Novel Molecular "Stapler" for Sequence-Specific Protein Conjugation", Bioconjug. Chem., 18(2), pp. 469-476 (2007).
Popp et al., "Sortagging: a versatile method for protein labeling". Nature Chemical Biology, 3(11), pp. 707-708 (2007).
Proft, T., "Sortase-mediated protein ligation: an emerging biotechnology tool for protein modification and immobilization" Biotechnol. Lett., 32(1), pp. 1-10 (2010).
Spirig et al., "Sortase enzymes in Gram-positive bacteria" Molec. Microbiol., 82(5), pp. 1044-1059 (2011).
Swee et al., "Sortase-mediated modification of αDEC205 affords optimization of antigen presentation and immunization against a set of viral epitopes" Proc. Nat. Acad. Sci. USA 110(4), pp. 1428-3 (2013).
Ton-That et al., "Anchoring of Surface Proteins to the Cell Wall of *Staphylococcus aureus*. Sortase catalyzed in vitro transpeptidation reaction using LPXTG peptide and NH2-GLY3 substrates", J. Biol. Chem., 275(13), pp. 9876-9881 (2000).
Wagner et al., "Bispecific antibody generated with sortase and click chemistry has broad antiinfluenza virus activity", Proc. Natl. Acad. Sci. USA, vol. 111, NR:47, pp. 16820-16825 (2014).
Wranik et al., "Luz-Y, A Novel Platform for the Mammalian Cell Production of Full-length IgG-bispecific Antibodies" J. Biol. Chem., 287(52), pp. 43331-43339 (2012).
Antos et al., "Recent advances in sortase-catalyzed ligation methodology." Current Opinion in Structural Biology, 38, pp. 111-118 (2016).
Ausubel et al. (Eds.), Current Protocols in Molecular Biology, vol. 1, Suppl. 47, John Wiley & Sons Inc., Table of Contents (1992).
Beerli et al., "Sortase Enzyme-Mediated Generation Of Site-Specifically Conjugated Antibody Drug Conjugates With High In Vitro And In Vivo Potency," pLos One, 10(7), pp. e0131177(1-17) (2015).
Bootcov et al., "MIC-1, a novel macrophage inhibitory cytokine, is a divergent member of the TGF-beta superfamily", Proc Natl Acad Sci USA, vol. 94 (21), pp. 11514-11519 (1997).
Booy et al., "Monoclonal and bispecific antibodies as novel therapeutics," Arch. Immunol. Ther. Exp., 54, 85-101 (2006).
Bostrom et al., "Variants of the antibody herceptin that interact with HER2 and VEGF at the antigen binding site", Science, vol. 323 (5921), pp. 1610-1614 (2009).
Brinkmann and Kontermann, "The making of bispecific antibodies", mAbs., vol. 9 (2), pp. 182-212 (2017).
Cao et al., "Bispecific antibody conjugates in therapeutics" Adv. Drug Deliv. Rev., 55, pp. 171-197 (2003).
Carillo et al., "The Multiple Sequence Alignment Problem in Biology", Siam J. Applied Math, vol. 48, pp. 1073-1082 (1988).
Cheung et al., Epitope-Specific Antibody Response to the Surface Antigen of Duck Hepatitis B Virus in Infected Ducks, Virology (1990), 176(2):546-552.

Chothia et al., Canonical Structures for the Hypervariable Regions of Immunoglobulins, J. Mol. Biol. (1987) 196(4):901-917.
Chothia et al., Conformations of Immunoglobulin Hypervariable Regions, Nature (1989), 342(6252): 877-883.
Creighton, "Proteins: Structure and Molecular Properties," 2nd ed., W. H. Freeman and Company, N.Y. (1984) (Table of Contents Only).
Dayhoff, M. O., "Atlas of Protein Sequence and Structure", National Biomedical Research, vol. 5 (Supplement 3) (1978) (Table of Contents Only).
Devereux et al., A Comprehensive Set of Sequence Analysis Programs for the VAX, Nucl. Acid Res. (1984), 12(1):387-395.
Digiammarino et al., "Design and generation of DVD-Ig™ molecules for dual-specific targeting," Methods Mol Biol., Chapter 9, vol. 899, pp. 145-156 (2012).
Fairlie et al., "Expression of a TGF-beta Superfamily Protein, Macrophage Inhibitory Cytokine-1, In the Yeast Pichia Pastoris", Gene, vol. 254(1-2), pp. 67-76 (Aug. 22, 2000).
Fischer et al., "Isolation, Renaturation, and Formation of Disulfide Bonds of Eukaryotic Proteins Expressed in *Escherichia coli* as Inclusion Bodies", Biotechnol Bioeng., vol. 41 (1), pp. 3-13 (Jan. 5, 1993).
Florio et al., "A bispecific antibody targeting sclerostin and DKK-1 promotes bone mass accrual and fracture repair", Nat Commun., vol. 7, 14 pages (2016).
Gribskov and Devereux (Eds.), Sequence Analysis Primer, Stockton Press, Table of Contents (1991).
Griffin and Griffin (Eds.), "Computer Analysis of Sequence Data, Part I", Methods in Molecular Biology, vol. 24, Humana Press, New Jersey, Table of Contents (1994).
Gunasekaran et al., "Enhancing Antibody Fc Heterodimer Formation Through Electrostatic Steering Effects: Applications to Bispecific Molecules and Monovalent IgG", J. Biol. Chem., vol. 285 (25), pp. 19637-19646 (2010).
Harlow and Lane, Antibodies: A Laboratory Manual, Cold Spring Harbor Laboratory, USA, Table of Contents (1988).
Henikoff et al., Amino Acid Substitution Matrices from Protein Blocks, Proc. Natl. Acad. Sci. U.S.A. (1992), 89(22):10915-10919.
Honegger et al., Yet Another Numbering Scheme for Immunoglobulin Variable Domains: An Automatic Modeling and Analysis Tool, J. Mol. Biol. (2001), 309:657-670.
Kabat et al., "Sequences of proteins of immunological interest", 5th Ed., U.S. Dept. of Health and Human Services, Table of Contents (1991).
Kirkland et al., Analysis of the Fine Specificity and Cross-Reactivity of Monoclonal Anti-Lipid A Antibodies, J. Immunol. (1986), 137(11):3614-3619.
Kostelny et al., "Formation of a bispecific antibody by the use of leucine zippers", J. Immunol., vol. 148 (5), pp. 1547-1553 (1992).
Lesk, Arthur M. (Ed.), Computational Molecular Biology: Sources and Methods for Sequence Analysis, Oxford University Press: New York, Table of Contents (1988).
Lindhofer et al., "Preferential species-restricted heavy/light chain pairing in rat/mouse quadromas. Implications for a single-step purification of bispecific antibodies", J Immunol., vol. 155 (1), pp. 219-225 (1995).
Liu et al., "A Novel Antibody Engineering Strategy for Making Monovalent Bispecific Heterodimeric IgG Antibodies by Electrostatic Steering Mechanism", J Biol Chem., vol. 290 (12), pp. 7535-7562 (2015).
Mack, M. et al., "A small bispecific antibody construct expressed as a functional single-chain molecule with high tumor cell cytotoxicity," PNAS, 92(15):7021-7025 (1995).
Moldenhauer et al., Identity of HML-1 Antigen on Intestinal Intraepithelial T Cells and of B-ly7 Antigen on Hairy Cell Leukaemia, Scand. J. Immunol. (1990), 32(2):77-82.
Morel et al., Monoclonal Antibodies to Bovine Serum Albumin: Affinity and Specificity Determinations, Molecular Immunol. (1988), 25(1):7-15.
Needleman et al., "A general method applicable to the search for similarities in the amino acid sequence of two proteins", J. Mol. Biol., vol. 48 (3), pp. 443-453 (1970).

(56) References Cited

OTHER PUBLICATIONS

Paul W E., "Immunoglobulins: Molecular Genetics", Fundamental Immunology, Raven Press, Ltd., 2nd Edition, 4 pages (1989).
Ridgway et al., "'Knobs-into-holes' engineering of antibody CH3 domains for heavy chain heterodimerization", Protein Eng., vol. 9 (7), pp. 617-621 (1996).
Rothman, et al., Antibody-dependent cytotoxicity mediated by natural killer cells is enhanced by castanospermine-induced alterations of IgG glycosylation, Mol Immunol. Dec. 1989;26(12):1113-23. doi: 10.1016/0161-5890(89)90055-2.
Sambrook and Russell, "Molecular Cloning: A Laboratory Manual", 3rd Ed., Cold Spring Harbor Laboratory Press, New York, vol. 1, Table of Contents (2001).
Schaefer et al., "Immunoglobulin domain crossover as a generic approach for the production of bispecific IgG antibodies", Proc. Natl. Acad. Sci. USA, vol. 108 (27), pp. 11187-11192 (2011).
Shields, et al., Lack of fucose on human IgG1 N-linked oligosaccharide improves binding to human Fcgamma RIII and antibody-dependent cellular toxicity, J Biol Chem. Jul. 26, 2002;277(30):26733-40. doi: 10.1074/jbc.M202069200. Epub May 1, 2002.
Shinkawa, et al., The absence of fucose but not the presence of galactose or bisecting N-acetylglucosamine of human IgG1 complex-type oligosaccharides shows the critical role of enhancing antibody-dependent cellular cytotoxicity, J Biol Chem. Jan. 31, 2003;278(5):3466-73. doi: 10.1074/jbc.M210665200. Epub Nov. 8, 2002.
Smith, "Biocomputing: Informatics and Genome Projects", Academic Press Inc., 10 pages (1994) (Table of Contents Only).
Songsivilai and Lachmann, "Bispecific antibody: a tool for diagnosis and treatment of disease", Clin. Exp. Immunol., vol. 79 (3), pp. 315-321 (1990).
Stahli et al., Distinction of Epitopes by Monoclonal Antibodies, Methods of Enzymology (1983), 92:242-253.
Umana, et al., Engineered glycoforms of an antineuroblastoma IgG1 with optimized antibody-dependent cellular cytotoxic activity, Nat Biotechnol. 17(2):176-80, 1999.
Van Heeke et al., "Expression of human asparagine synthetase in *Escherichia coli*", J Biol Chem., vol. 264 (10), pp. 5503-5509 (1989).
Von Heinje, G., Sequence Analysis in Molecular Biology, New York: Academic Press, Inc., Harcourt Brace Jovanovich, Publishers (1987) Table of Contents Only.
Wu et al., "Simultaneous Targeting of Multiple Disease Mediators by a Dual-variable domain Immunoglobulin," Nature Biotechnology vol. 25 (11), pp. 1290-1297 (2007).
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnol Bioeng., vol. 87 (5), pp. 614.

\* cited by examiner
† cited by third party

ANALYSIS OF TNFA/TLA1 PURITY BY ANALYTICAL SIZE EXCLUSION AND CATION EXCHANGE CHROMATOGRAPHIES

FIG. 16
ANALYSIS OF PAC1/CGRPR1 PURITY BY ANALYTICAL SIZE EXCLUSION AND CATION EXCHANGE CHROMATOGRAPHIES
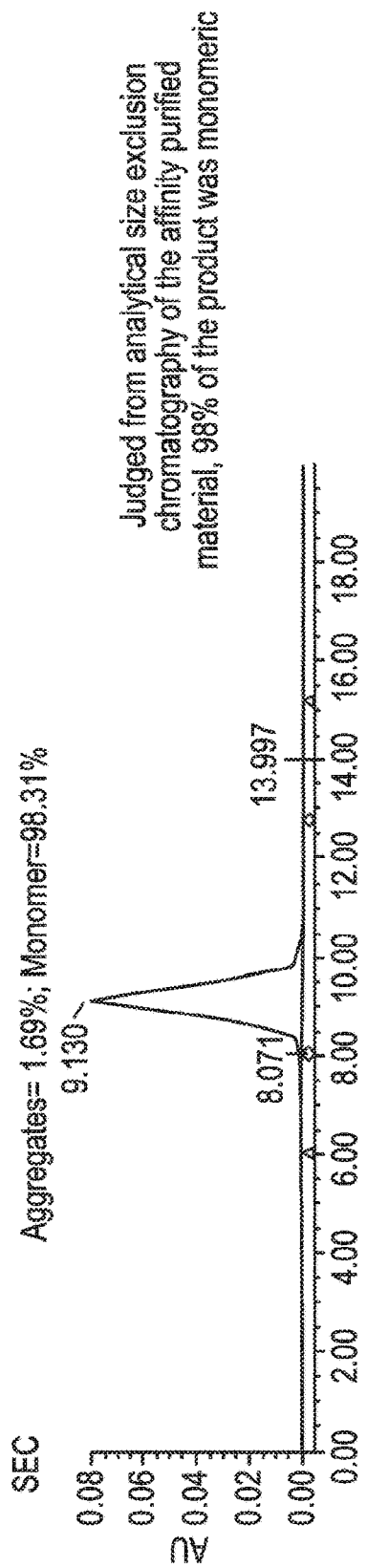
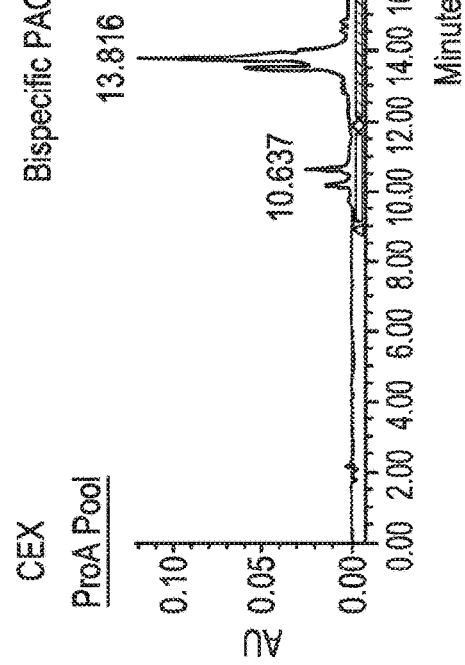

UPLC: ANALYTICAL SEC PROFILE OF PAC1/CGRPR1 AFTER PRO A PURIFICATION

CALIPER ANALYSIS OF PAC1/CGRPR1 BISPECIFIC ANTIBODY PRODUCED BY C-TERMINAL CHARGE PAIRED TAG

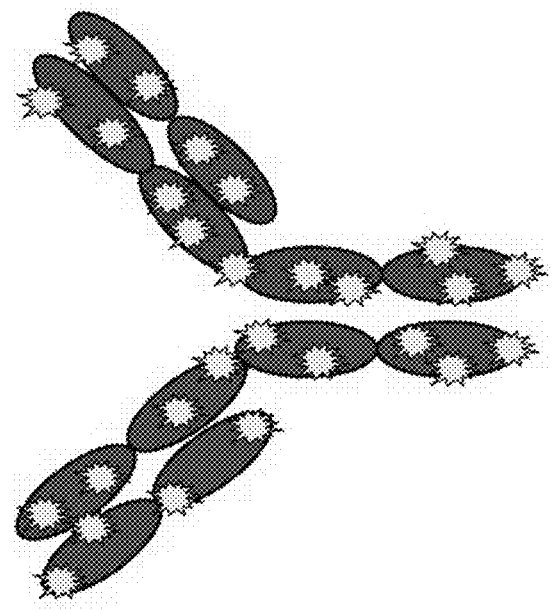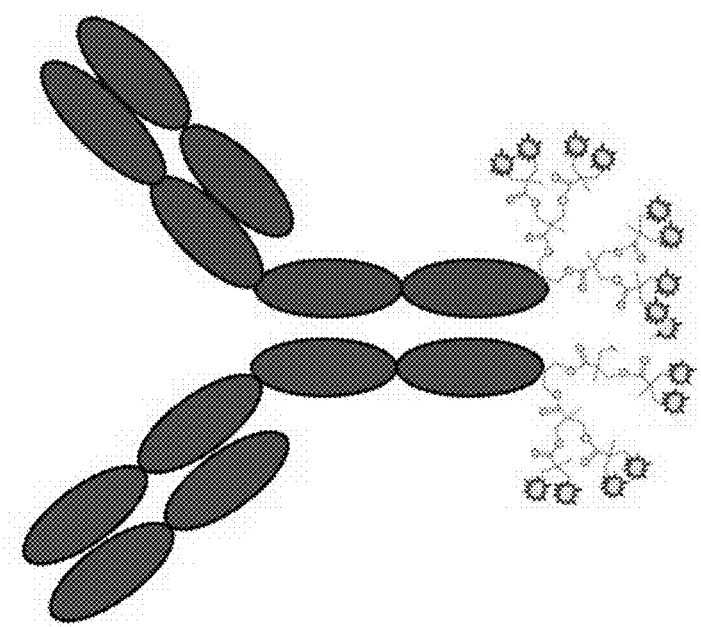
FIG. 29

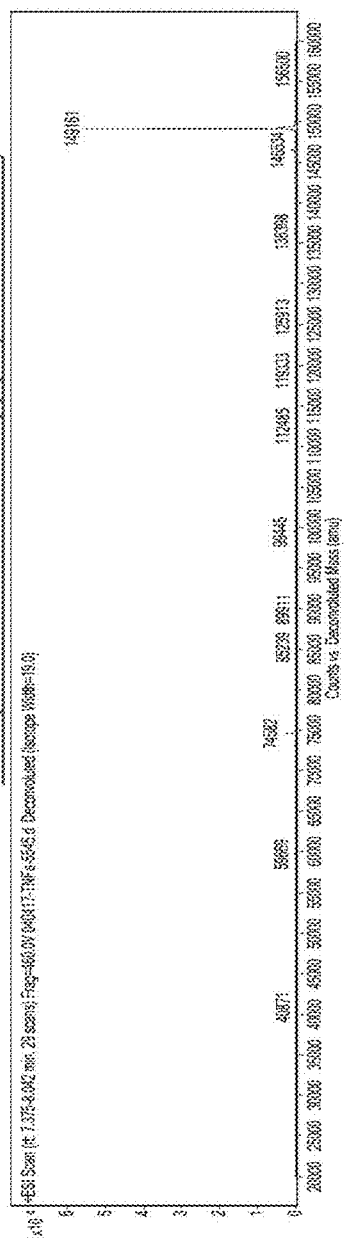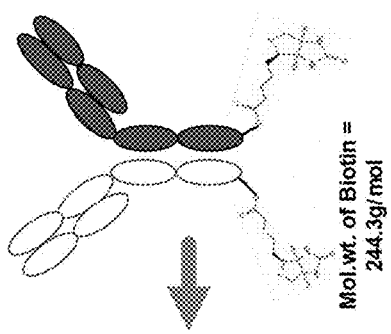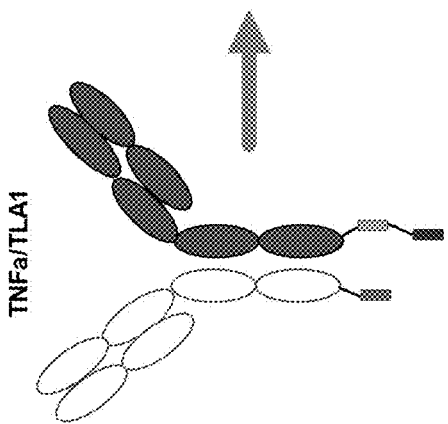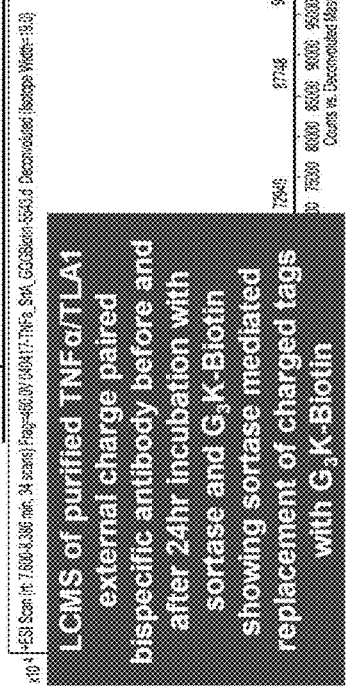
FIG. 30

PEGYLATION OF PAC1/CGRPR1 AND TNFα/TLA1 THROUGH SORTASE A

SDS PAGE: PEGYLATION OF PAC1/CGRPR1 AND TNFα/TLA1 BISPECIFICS WITH 20KD-PEG USING SORTASE A – BIABS + SRTA + G₃C-PEG20K

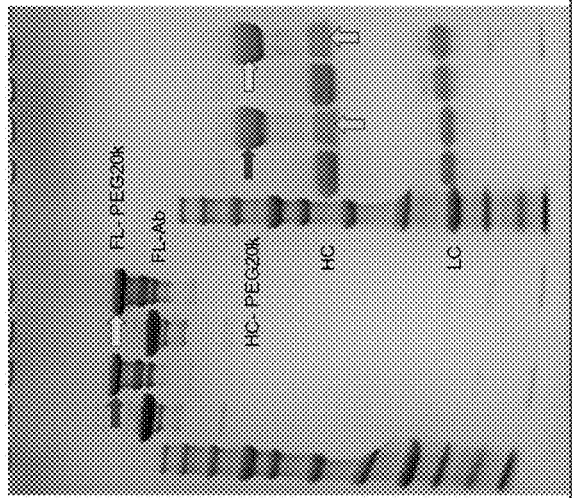

Lanes:
1. NEB Blue broad range prestained protein standard
2. TNFa/TLA1 + G3-PEG20k (-)
3. TNFa/TLA1 + G3-PEG20k + SrtA2.0
4. PAC1/CGRPR1 + G3-PEG20k (-)
5. PAC1/CGRPR1 + G3-PEG20k + SrtA2.0
6. Blank
7. Blank
8. NEB Blue broad range prestained protein standard
9. TNFa/TLA1 + G3-PEG20k (-) - Reduced
10. TNFa/TLA1 + G3-PEG20k + SrtA2.0- Reduced
11. PAC1/CGRPR1 + G3-PEG20k (-) - Reduced
12. PAC1/CGRPR1 + G3-PEG20k + SrtA2.0- Reduced Shift in size of bispecific PAC1/CGRPR1 and TNFalpha/TLA1 after conjugation with 20kd PEG. Molar Conjugated antibody could potentially be eliminated from non-conjugated by ion-exchange due to charge quenching of the PEGylated form

FIG. 35

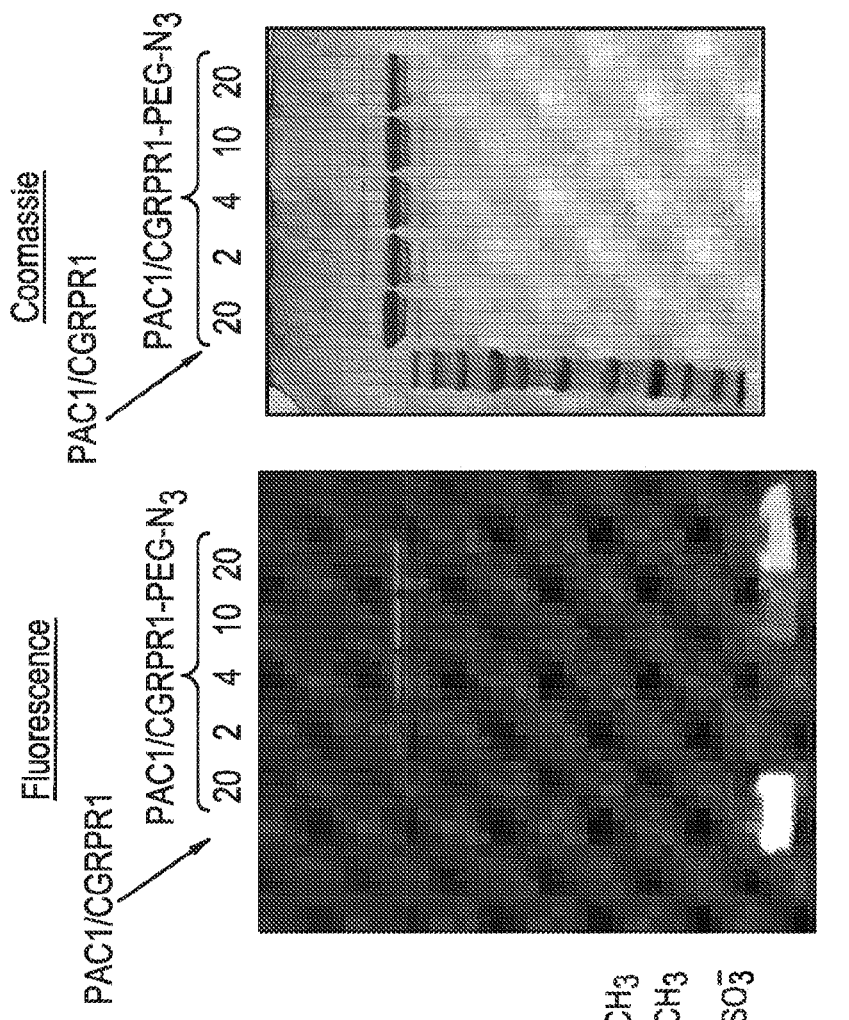
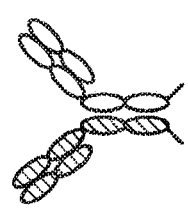
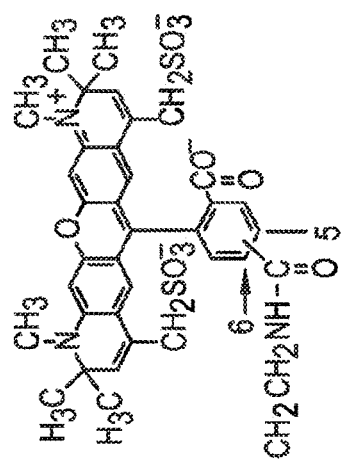
FIG. 40

BISPECIFIC ANTIBODIES WITH CLEAVABLE C-TERMINAL CHARGE-PAIRED TAGS

CROSS REFERENCE TO RELATED APPLICATIONS

This application is a national stage application under 35 U.S.C. § 371 of International Application No. PCT/US2019/031379, having an international filing date of 8 May 2019, which claims the benefit of U.S. Provisional Patent Application No. 62/668,626, filed 8 May 2018, each of which is incorporated herein by reference in its entirety.

FIELD OF THE INVENTION

This invention relates to novel engineered proteins, multi-specific protein complexes, including multi-specific antibodies, methods of constructing them and producing them. This invention also relates to the new application of technologies useful in obtaining the multi-specific protein complexes.

The instant application contains an ASCII "txt" compliant sequence listing which serves as both the computer readable form (CRF) and the paper copy required by 37 C.F.R. Section 1.821 (c) and 1.821 (e), and is hereby incorporated by reference in its entirety. The name of the "txt" file created on May 8, 2019, is: A-2238-WO-PCT_SEQ_LIST_050719_ST25, and is 30 kb in size.

BACKGROUND OF THE INVENTION

The development of multi-specific antibodies as therapeutic agents for human diseases has great clinical potential. Multi-specific antibodies can simultaneously recognize two different antigens, neutralize different pathogenic mediators, recruit different type of effector cells, and modulate signal pathways. However, production of multi-specific antibodies has been very challenging. The broad application of multi-specific antibodies has been hindered by the difficulties of developing a platform for producing multi-specific antibodies that exhibit favorable half-life, high stability, lack of immunogenicity, and feasibilities for large scale manufacturing and purification. Promising multi-specific antibodies formats such as DVD-Ig (Dual Variable Domain Ig) (Nature Biotechnology 25, 1290-1297 (2007)); Cross-over Ig [Schaefer W et al (2011) PNAS 108 (27): 11187-11192]; Two-in-One Ig (Science 2009, 323, 1610); BiTER antibodies [PNAS 92 (15): 7021-7025; 1995] allow the production of a multi-specific antibody, but they do have different kinds of liabilities.

Several innovative technologies have enabled the almost exclusive assembly of the Fc heterodimer to provide the backbone for designing multi-specific ity, e.g. knob-in-hole (Ridgway et al, Protein Eng. 9:617, 1996), electrostatic steering (Gunasekaran et al, J. Biol. Chem. 285:19637, 2010) and strand-exchange engineering domain (SEED) (Davis, Protein Eng. Des. & Sel. 23:195, 2010). In the Dual Variable Domains (DVD)-Ig approach, the VL and VH of the second antibody are fused via flexible linkers to the N-termini of the light and heavy chains, respectively, of the first antibody, creating two variable domains (VD) in tandem, called the outer VD and the inner VD (Wu et al, ibid). Due to the steric hindrance caused by the proximity of the outer VD to the ligand-binding site of the inner VD, extensive optimization involving VD selection from a number of available monoclonal antibodies, orientation of VDs, and linker designs, most of which have to be empirically determined, is necessary to retain the binding affinity of the inner VD (DiGiammarino et al, Methods Mol. Biol. 899:145, 2012).

Another method takes advantage of the species-restricted heavy and light chain pairing in rat/mouse quadromas (Lindhofer et al, J. Immunol. 155:219, 1995). However, the multi-specific antibody generated is a rat/mouse antibody, which obviously has immunogenicity issues as a therapeutic.

The Crossmab approach, based on the knob-into-hole heterodimerized heavy chains, in addition uses immunoglobulin domain crossover as a generic approach for the production of multi-specific IgG antibodies (Schaefer et al, Proc. Natl. Acad. Sci. USA, 108:1 1 187, 201 1). Nevertheless, the correct pairings of the H chain heterodimer and the cognate Fv's are not exclusive, and the unwanted side products have to be removed during purification.

An extension of the Crossmab approach was used to generate a tetravalent multi-specific antibody by tagging an extra set of Fab and Crossmab Fab fragments to the C-termini of Crossmab (Regula et al, US Patent Application No: 2010/0322934), and the challenges of obtaining exclusively correct pairings of the H chain heterodimer and the cognate Fv's remain.

A further approach to multi-specificity is to use a single binding site to target two different antigens was demonstrated by a "two-in-one" antibody. One such "two-in-one" antibody is a variant of the antibody Herceptin, which interacts with both Her2 and VEGF (Bostrom et al, Science 323:1610, 2009). This approach is attractive for clinical applications because it provides a multi-specific antibody that has an identical format as a normal IgG. However, screening for such a variant is very labor intensive and there is no guarantee that a single binding site which can bind both antigens of interest can be obtained.

Finding technologies for building multi-specific antibodies that are useful and scalable for commercial and therapeutic purposes has been elusive. Many methods have been tried, but nearly all suffer significant drawbacks such as being poorly soluble; inexpressible in mammalian cells, demonstrating low yield of heterodimer formation, technically challenging to manufacture, immunogenic, short half-life in vivo, unstable among other problems (e.g., Hollinger et al., (1993) PNAS 90:6444-6448; U.S. Pat. Nos. 5,932, 448; 6,833,441; 5,591,828; 7,129,330; 7,507,796; Fischer et al., (2007) Pathobiology 74:3-14; Booy (2006) Arch. Immunol. Ther. Exp. 54:85-101; Cao et al (2003) 55:171-197; and Marvin et al., (2006) Current Opinion in Drug Discovery & Development 9 (2): 184-193. Thus, there is a need for improved technologies and processes to make multi-specific antibodies.

SUMMARY OF THE INVENTION

In one aspect, the present invention is directed to a CH3-containing molecule comprising (a) a first polypeptide comprising a CH3 domain and a negatively charged domain comprising at least four consecutive negatively charged amino acid residues; and (b) a second polypeptide comprising a CH3 domain and a positively charged domain comprising at least four consecutive positively charged amino acid residues.

In one embodiment, the CH3 domain and the negatively charged domain of the first polypeptide are positioned relative to each other in an N-terminal to C-terminal direction and the CH3 domain and the positively charged domain of the second polypeptide are positioned relative to each other in an N-terminal to C-terminal direction. In one embodiment, the first and second polypeptides each further comprise a CH2 domain. In one embodiment, the first and second polypeptides each further comprise a hinge domain. In one embodiment, the first and second polypeptides each comprise VH, CH1, hinge, CH2, and CH3 domains positioned relative to each other in an N-terminal to C-terminal direction.

In one embodiment, the molecule further comprises a third and a fourth polypeptide, wherein the third polypeptide comprises a first VL domain and the fourth polypeptide comprises a second VL domain. In one embodiment, the third polypeptide further comprises a first CL domain wherein the first VL and CL domains are positioned relative to each other within the third polypeptide in an N-terminal to C-terminal direction, and the fourth polypeptide further comprises a second CL domain, and wherein the second VL and CL domains are positioned relative to each other within the fourth polypeptide in an N-terminal to C-terminal direction.

In one embodiment, the negatively charged domain comprises at least five, at least six, or at least seven consecutive negatively charged amino acid residues and the positively charged domain comprises at least five consecutive positively charged amino acid residues.

In one embodiment, the negatively charged amino acid residues are aspartic acid residues and the positively charged amino acid residues are selected from the group consisting of lysine, arginine, and histidine residues. In one embodiment, the negatively charged amino acid residues are aspartic acid residues and the positively charged amino acid residues are lysine residues.

In one embodiment, the negatively charged amino acid residues are glutamic acid residues and the positively charged amino acid residues are selected from the group consisting of lysine, arginine, and histidine residues.

In one embodiment, the first polypeptide further comprises a linker sequence covalently attached to the C-terminus of the CH3 domain and the linker is attached to the N-terminus of the negatively charged domain; and wherein the second polypeptide further comprises a linker sequence covalently attached to the C-terminus of the CH3 domain and the linker is attached to the N-terminus of the positively charged domain.

In one embodiment, the linker of the first polypeptide is the same as the linker of the second polypeptide.

In one embodiment, the linker can be cleaved by an enzyme. In one embodiment, the enzyme is selected from the group consisting of sortase A, sortase B, sortase C, sortase D, sortase E, and sortase F.

In one embodiment, the linker comprises the amino acid sequence of SEQ ID NO: 1 (LPETGGEEST); SEQ ID NO: 2 (LPXTG, wherein X can be any amino acid); SEQ ID NO: 3 (LPETG); SEQ ID NO: 4 (LPETGG); SEQ ID NO: 5 (LPXTA, wherein X can be any amino acid): SEQ ID NO: 6 (NPX [T/S] [N/G/S], wherein X can be any amino acid); SEQ ID NO: 7 (IPXTG, wherein X can be any amino acid); and SEQ ID NO: 8 (LAXTG, wherein X can be any amino acid).

In one embodiment, either the first polypeptide, the second polypeptide, or both further comprises a purification tag attached to its C-terminus.

In one embodiment, the purification tag is selected from the group consisting of a his-tag, a strep-tag, a flag-tag, a T7-tag, a V5-peptide-tag, a GST-tag, a CBP-tag, a MBP-tag and a c-Myc-tag. In one embodiment, the purification tag is a his-tag comprising at least five consecutive histidine amino acid residues.

In one embodiment, the first polypeptide comprises the amino acid sequence of SEQ ID NO: 9 (LPETGGEESTDDDDDDD) and the second polypeptide comprises the amino acid sequence of SEQ ID NO: 10 (LPETGGEESTKKKKKKKHHHHHH).

In one embodiment, the first polypeptide comprises the amino acid sequence of SEQ ID NO: 11 (LPETGGEESTDDDDDDDHHHHHH) and the second polypeptide comprises the amino acid sequence of SEQ ID NO: 12 (LPETGGEESTKKKKKKK).

In one aspect the present invention is directed to a multi-specific antibody comprising a first heavy chain polypeptide, a first light chain polypeptide, a second heavy chain polypeptide, and a second light chain polypeptide, wherein
  the first heavy chain polypeptide comprises a CH3 domain and a negatively charged domain comprising at least four consecutive negatively charged amino acid residues and the first heavy chain polypeptide and the first light chain polypeptide bind to a first antigen; and
  the second heavy chain polypeptide comprises a CH3 domain and a positively charged domain comprising at least four consecutive positively charged amino acid residues and the second heavy chain polypeptide and the second light chain polypeptide bind to a second antigen.

In one embodiment, the multi-specific antibody is expressed by a mammalian cell. In one embodiment, the mammalian cell is a HEK or a CHO cell.

In one aspect, the present invention is directed to a method of producing a multi-specific antibody, the method comprising the step of culturing a cell comprising a vector encoding a multi-specific antibody of the present invention in a culture medium.

In one embodiment, the method further comprises recovering the multi-specific antibody from the cell or the culture medium.

In one aspect, the present invention is directed to a method for preparing an antibody conjugate, the method comprising the steps of;
  a) providing a multi-specific antibody; and
  b) treating the antibody with a sortase enzyme in the presence a synthetic molecule, wherein the molecule comprises an gly-gly-gly sequence. In one embodiment, step b) is performed using a synthetic molecule: antibody molar ratio of about 2 to about 1000.

Other features and advantages of the invention will be apparent from the following Detailed Description, the Drawings, and the Claims.

BRIEF DESCRIPTION OF THE DRAWINGS

FIG. 16 depicts Analysis of PAC1/CGRPR1 Purity by Analytical Size Exclusion and Cation Exchange Chromatographies.

FIG. 29 depicts Site Specific Labeling of Bispecific Antibody.

FIG. 30 depicts Sortase A Mediated Biotinylation of TNFα/TLA1.

FIG. 35 depicts SDS Page: PEGylation of PAC1/CGRPR1 and TNFα/TLA1 Bispecifics With 20kd-PEG Using Sortase A-Biabs+Sortase A+G3c-PEG20k.

FIG. 40 depicts PAC1/CGRPR1-PEG3-N3+Dibo-Alexa488 Click Chemistry Reaction—24 hour Incubation.

DETAILED DESCRIPTION

Figure 1:
FIG. 1 depicts the Engineering of Bispecific Antibody Through C-Terminal Charge Paired Tags.
Figure 2:
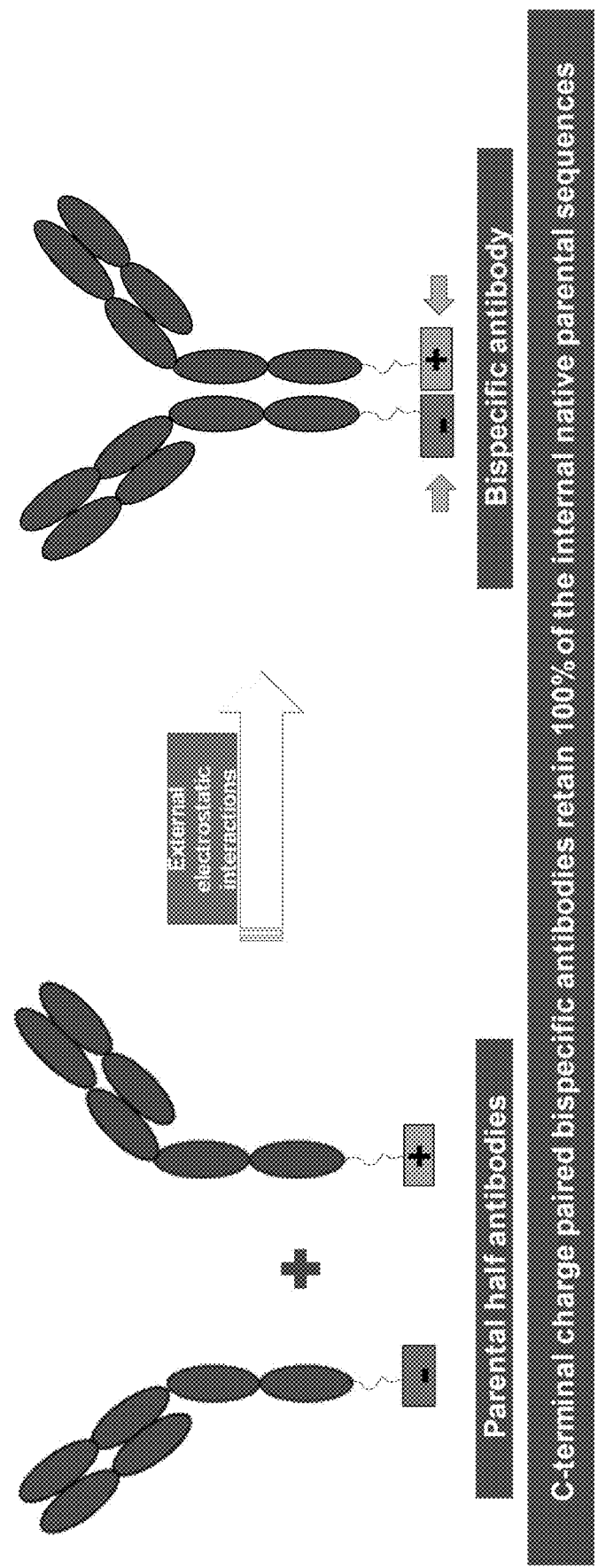
FIG. 2 depicts Bispecific Antibody Based On C-Terminal Charge Paired Tags.
Figure 3:
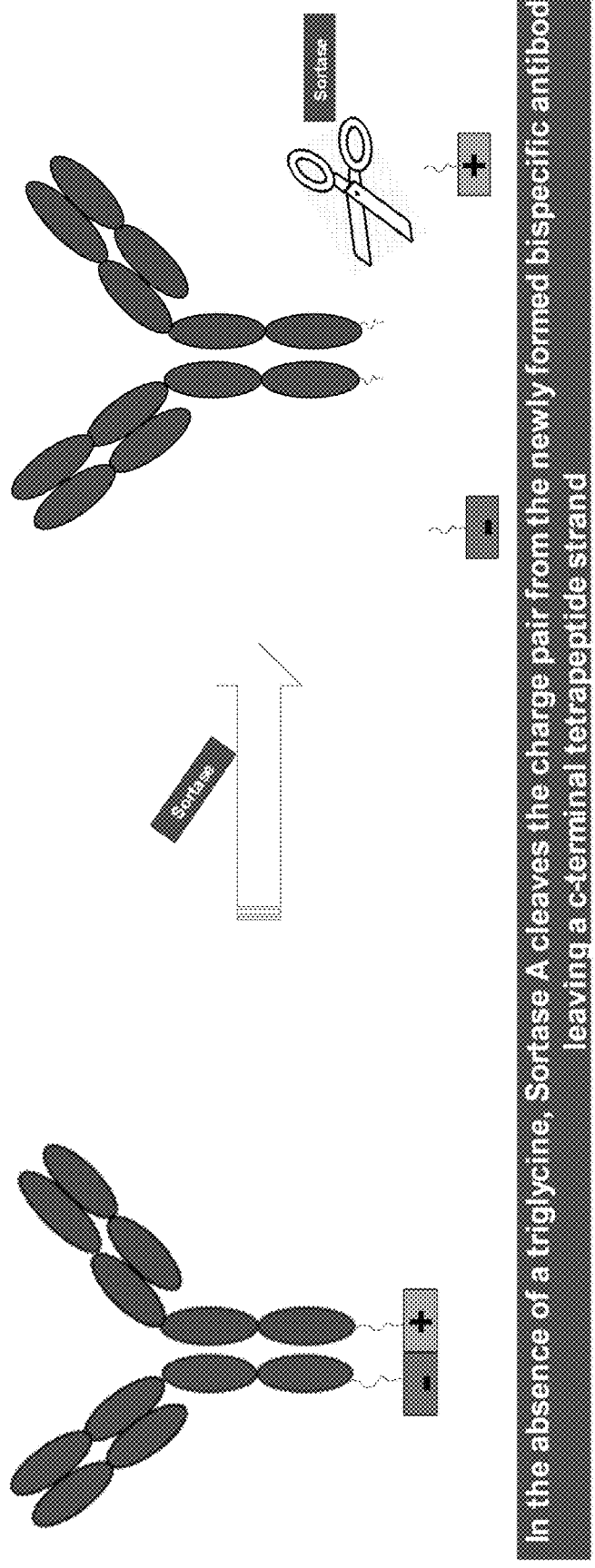
FIG. 3 depicts Bispecific Antibody Based C-Terminal Charge Paired Tags.
Figure 4:
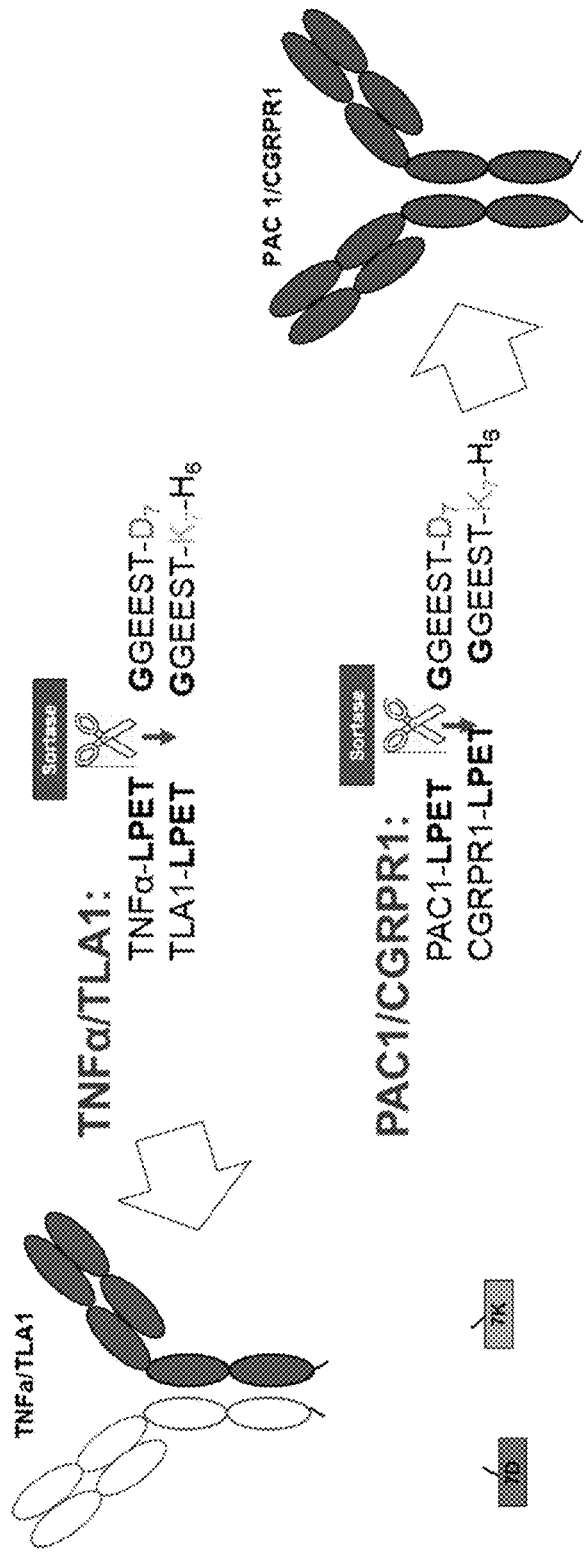
FIG. 4 depicts Excision of C-Terminal Charge Paired Tags from Bispecific Antibody by Sortase.
Figure 5:
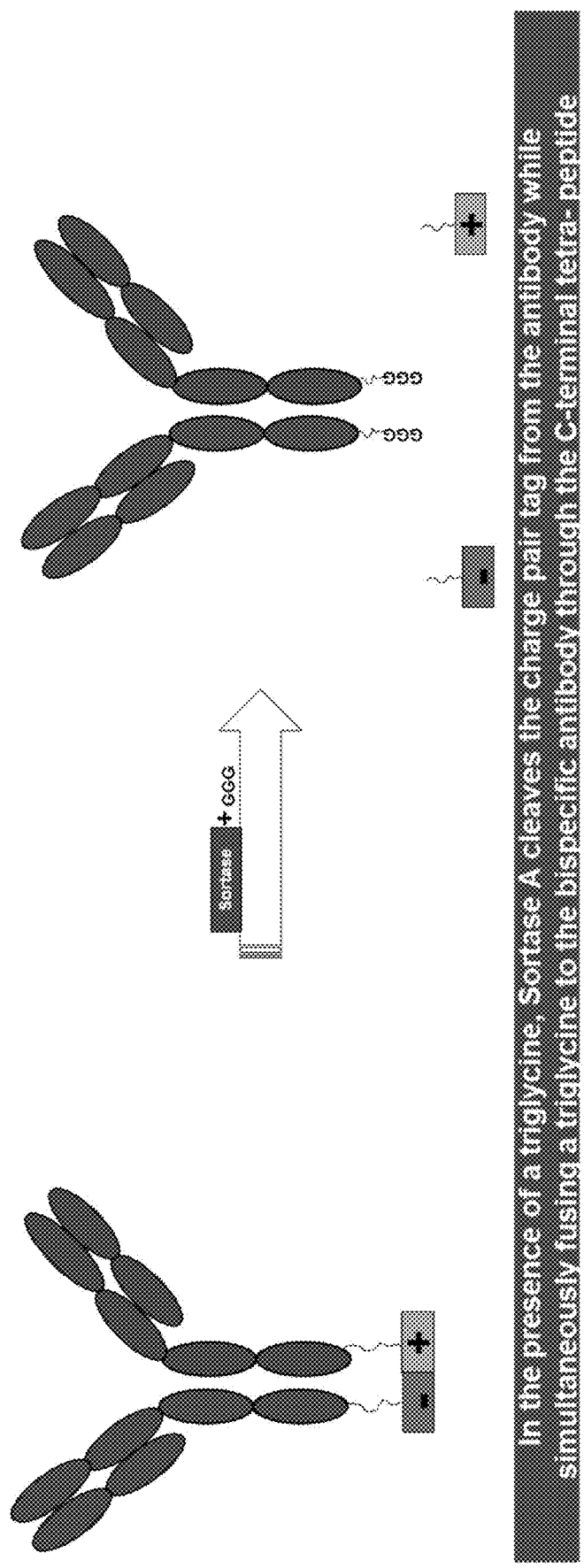
FIG. 5 depicts Transpeptidation of Bispecific Antibody Produced Through C-Terminal Charge Paired Tags.
Figure 6:
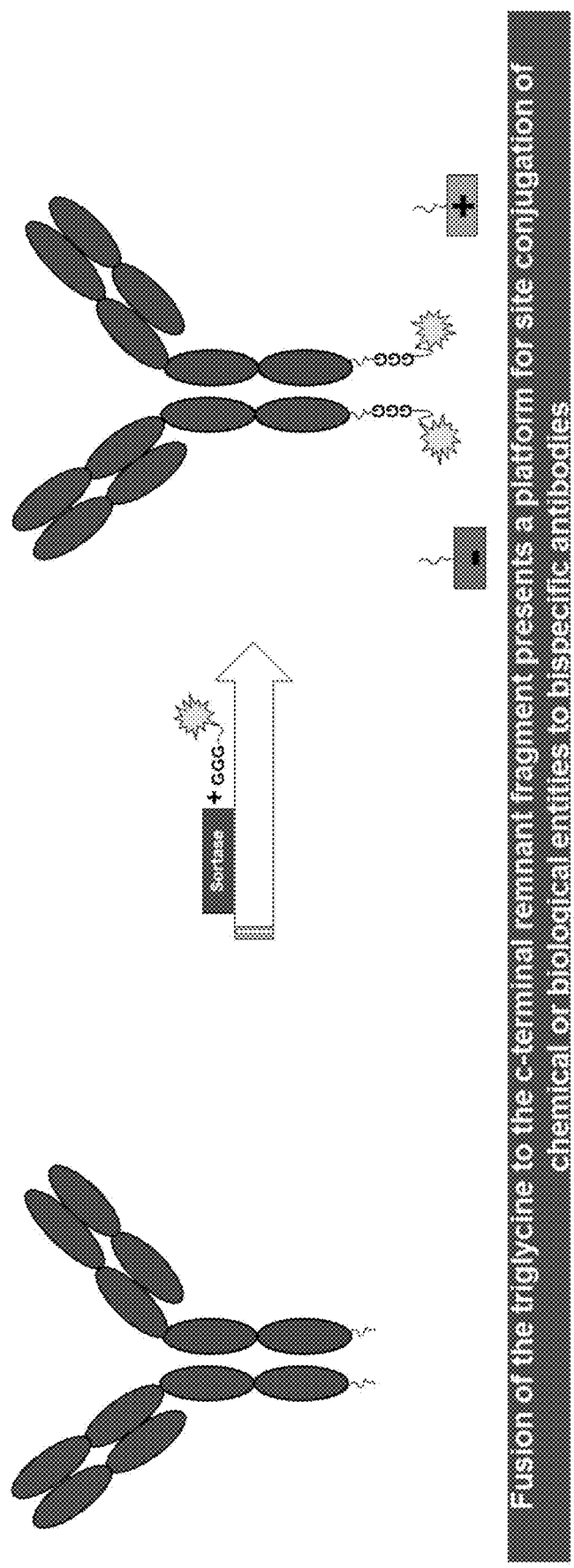
FIG. 6 depicts Bispecific Antibody Drug Conjugate Produced Through C-Terminal Charge Paired Tags.
Figure 7:
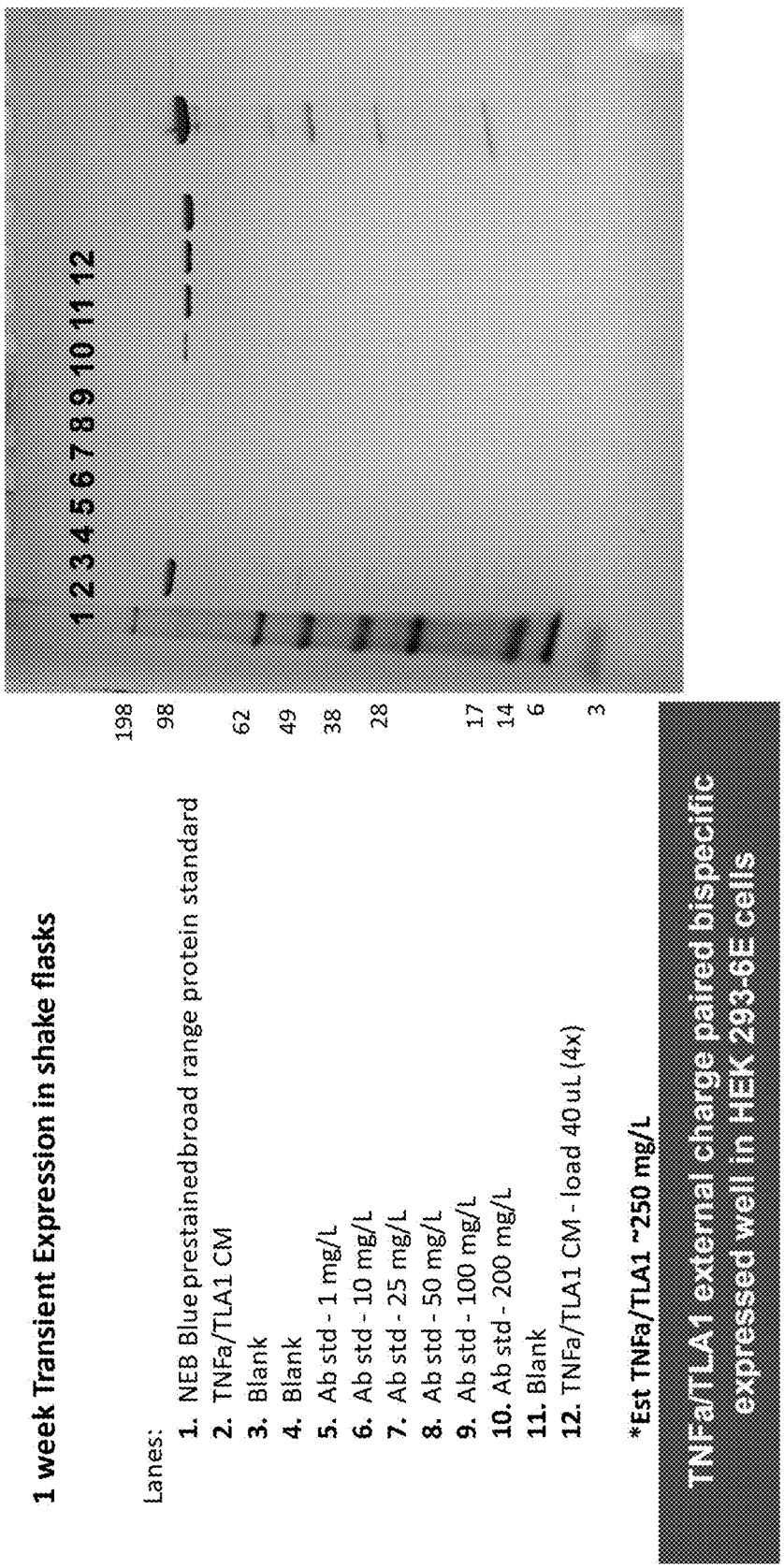
FIG. 7 depicts Transient HEK 293-6e Expression-TNFα/TLA1.
Figure 8:
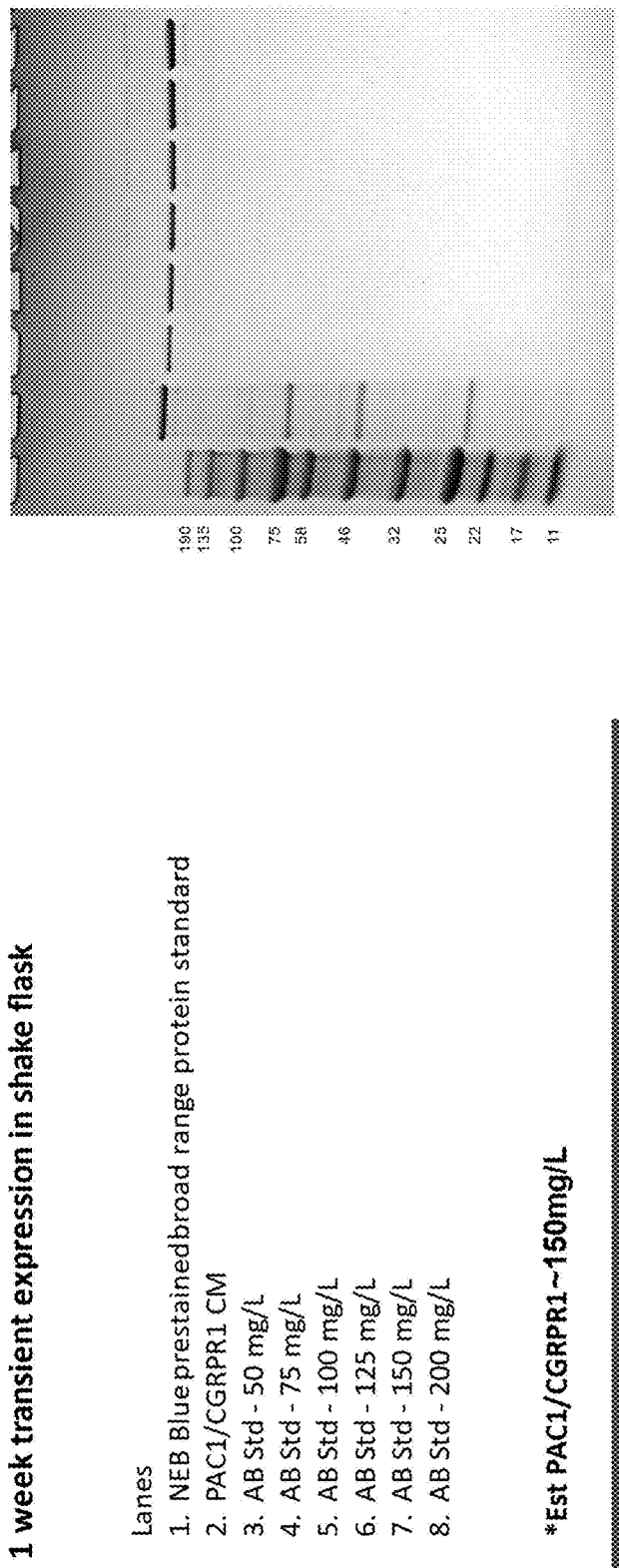
FIG. 8 depicts Transient HEK 293-6e Expression-PAC1/CGRPR1.
Figure 9:
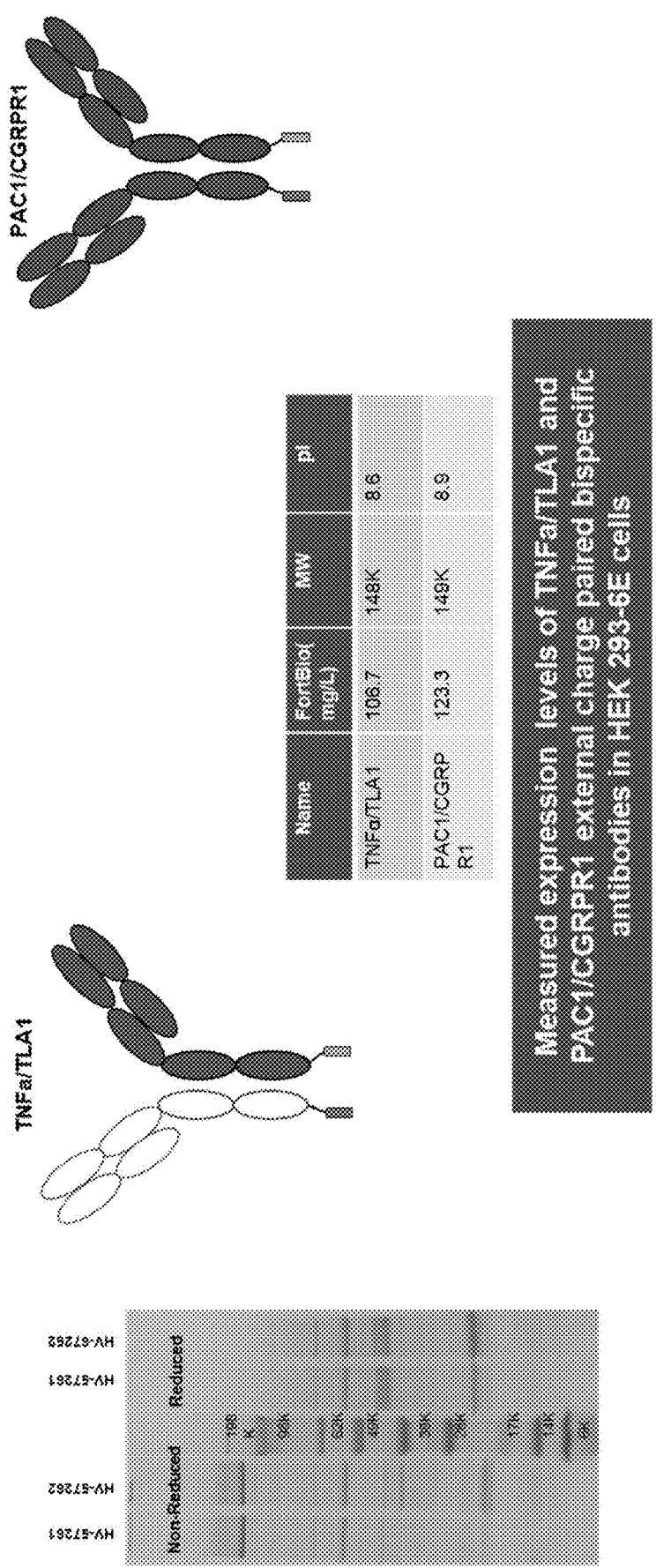
FIG. 9 depicts Expression Levels of C-Terminal Charge-Paired Bispecific TNFα/TLA1 and PAC1/CGRPR1 (150-250 mg/L).
Figure 10:
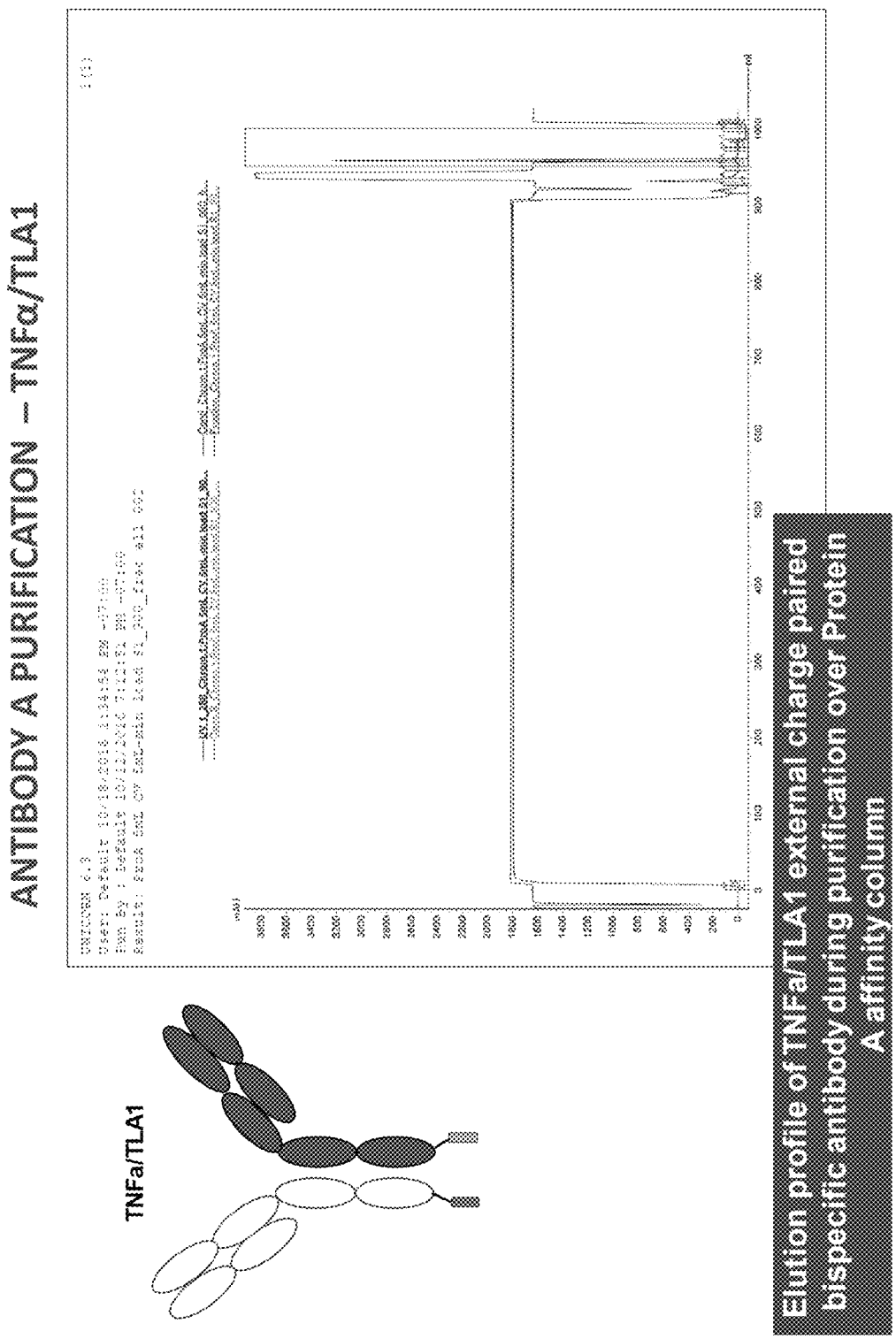
FIG. 10 depicts Antibody A Purification-TNFα/TLA1.
Figure 11:
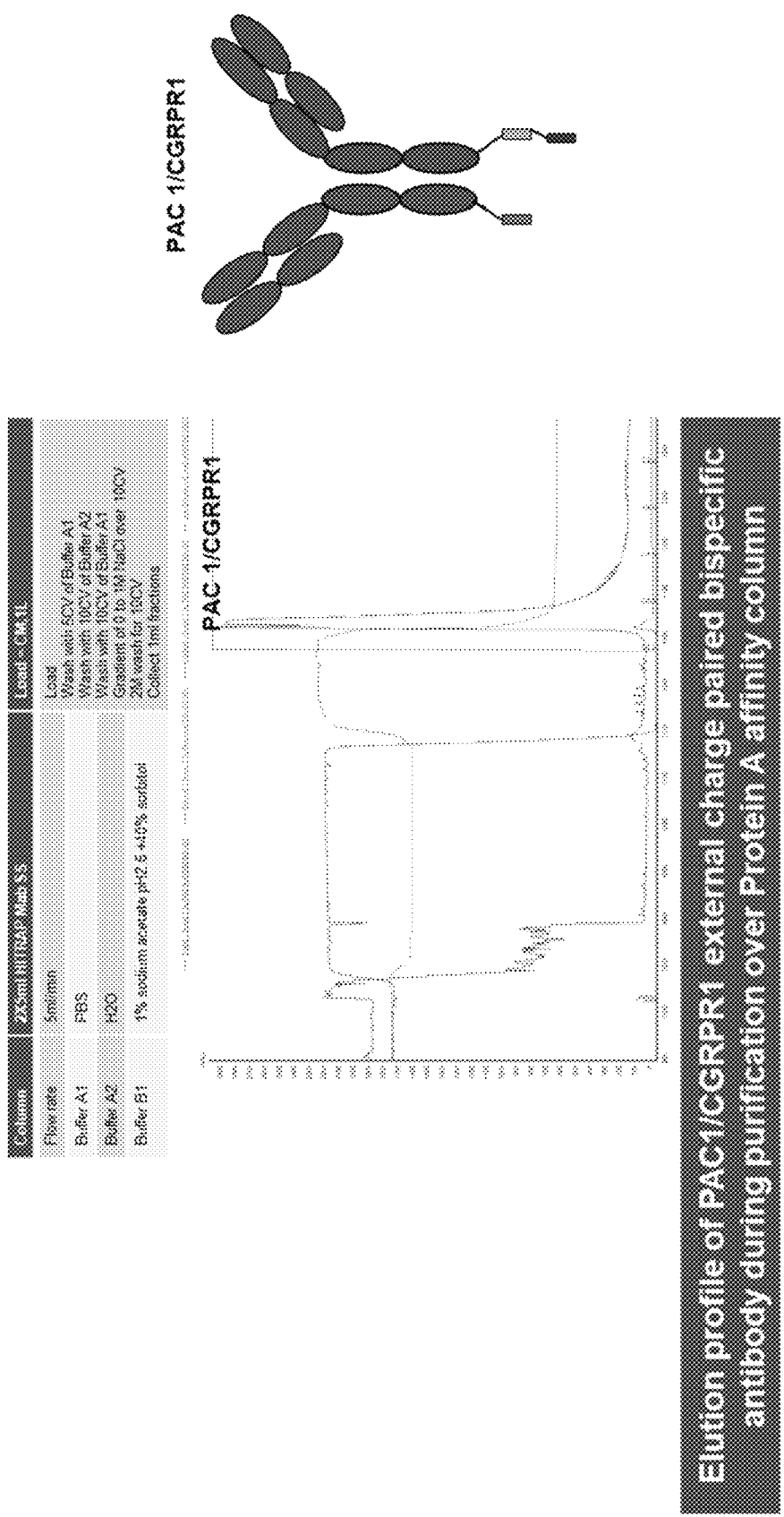
FIG. 11 depicts Elution Profile: Protein A Affinity Purification of PAC1/CGRPR1.
Figure 12:
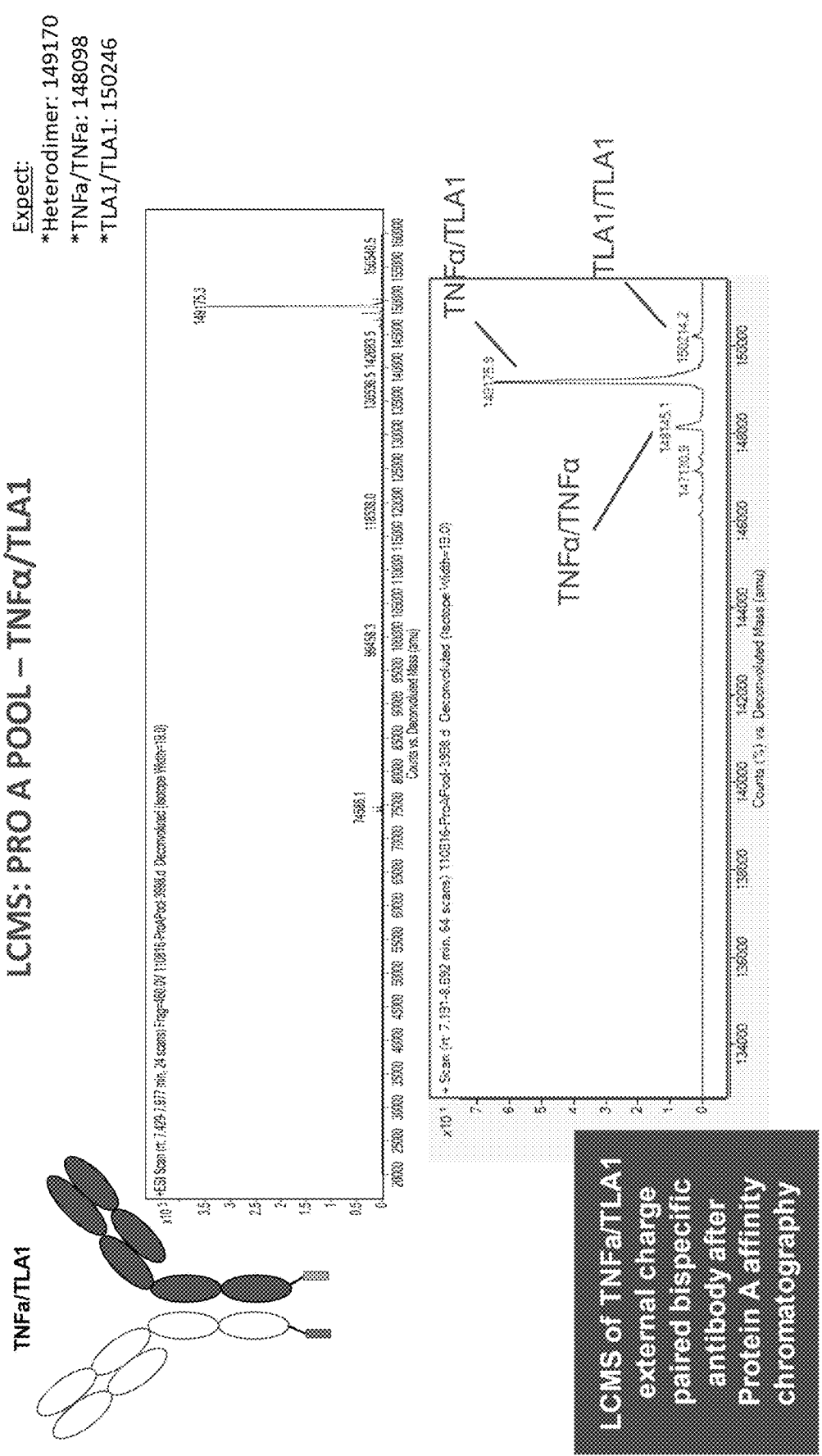
FIG. 12 depicts LCMS: Pro A Pool-TNFα/TLA1.
Figure 13:
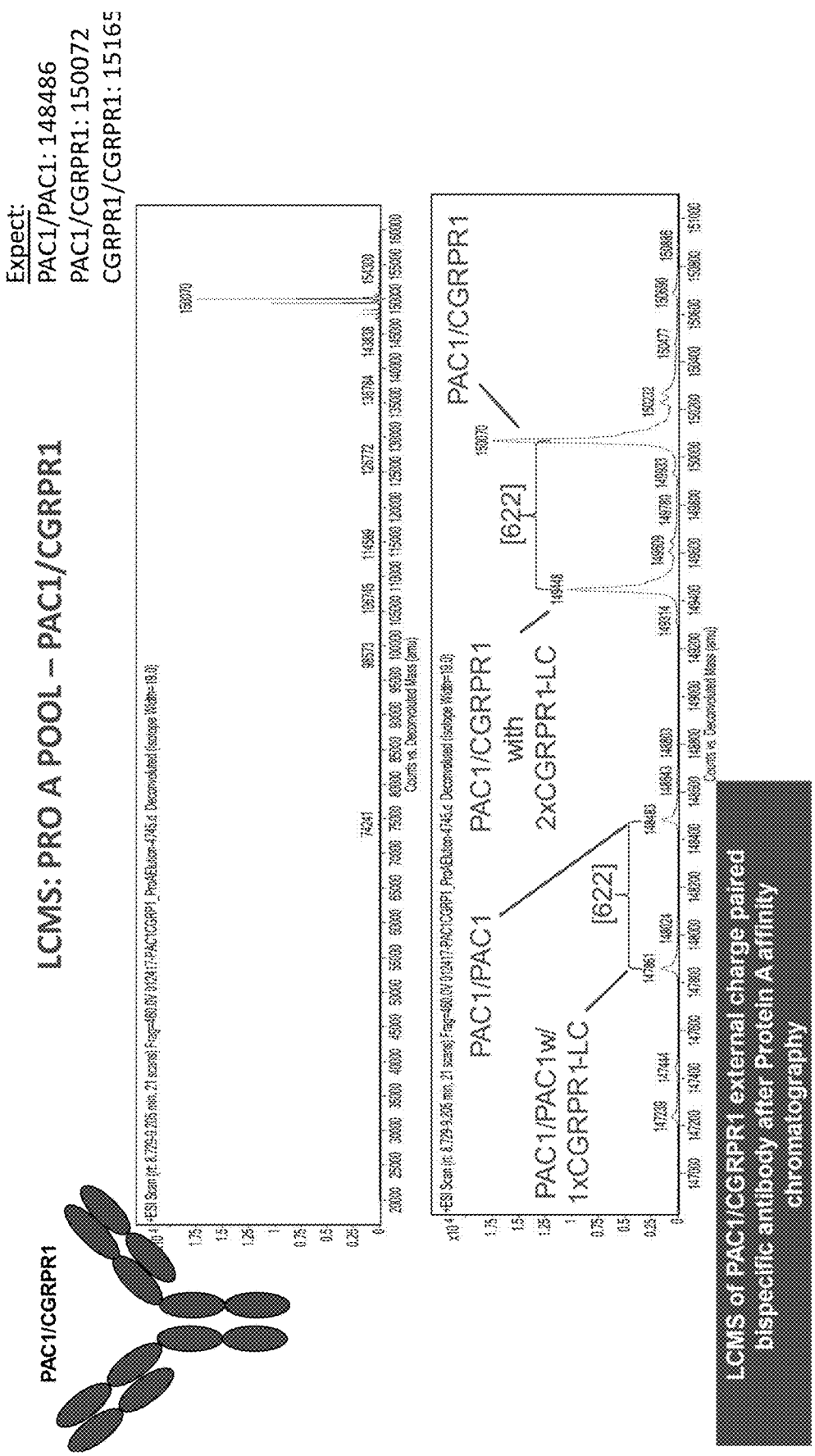
FIG. 13 depicts LCMS: Pro A Pool-PAC1/CGRPR1.
Figure 14:
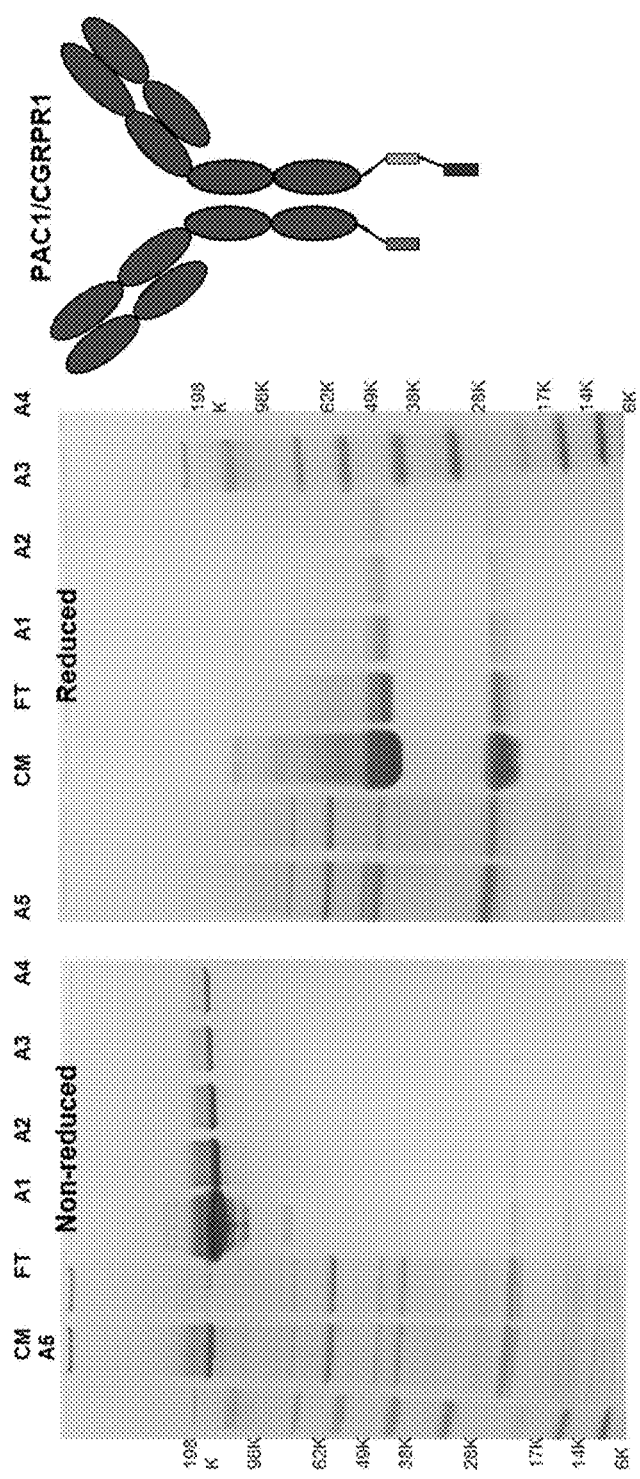
FIG. 14 depicts SDS-Page: Protein A Affinity Purification of PAC1/CGRPR1.
Figure 15:
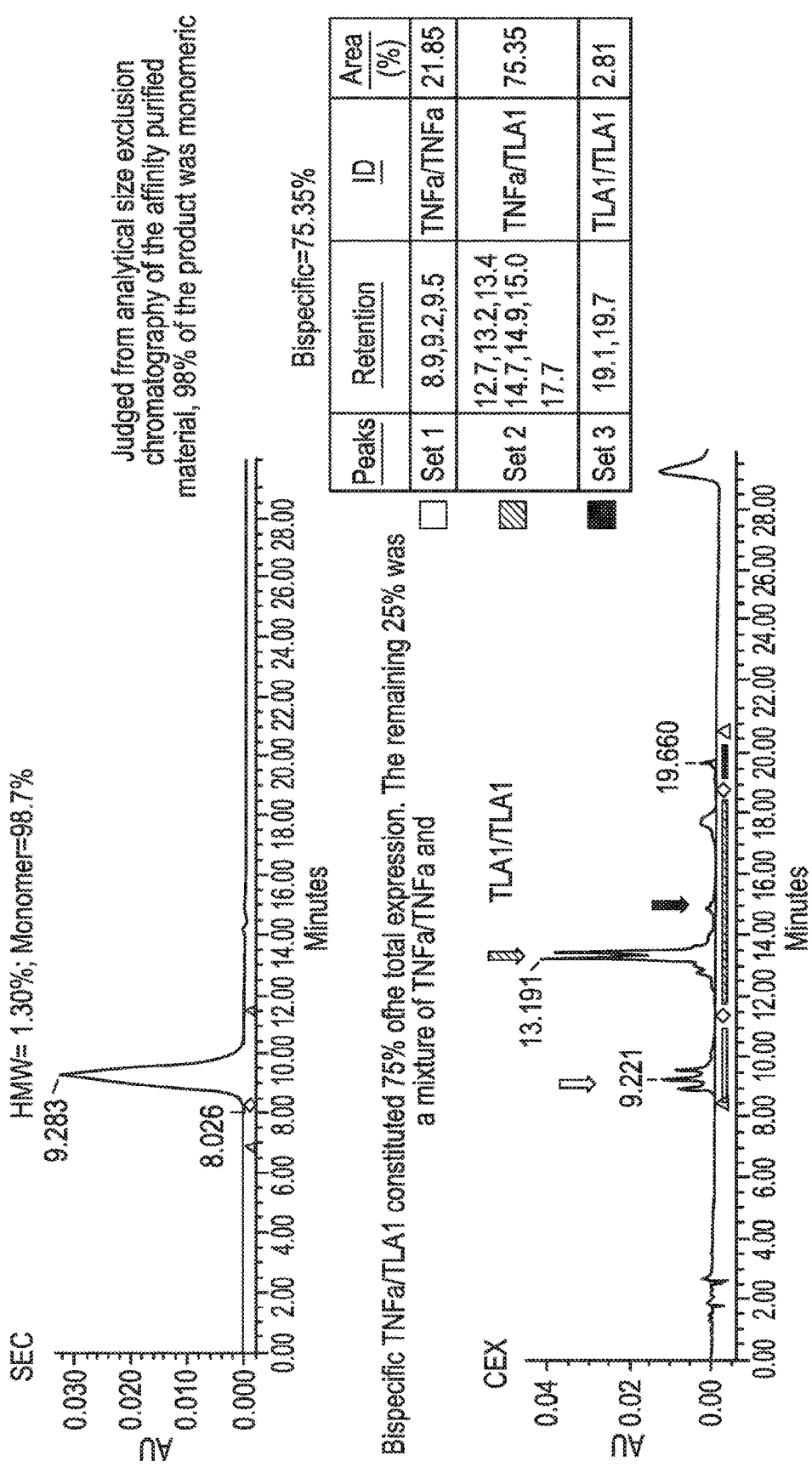
FIG. 15 depicts Analysis of TNFα/TLA1 Purity by Analytical Size Exclusion and Cation Exchange Chromatographies.
Figure 17:
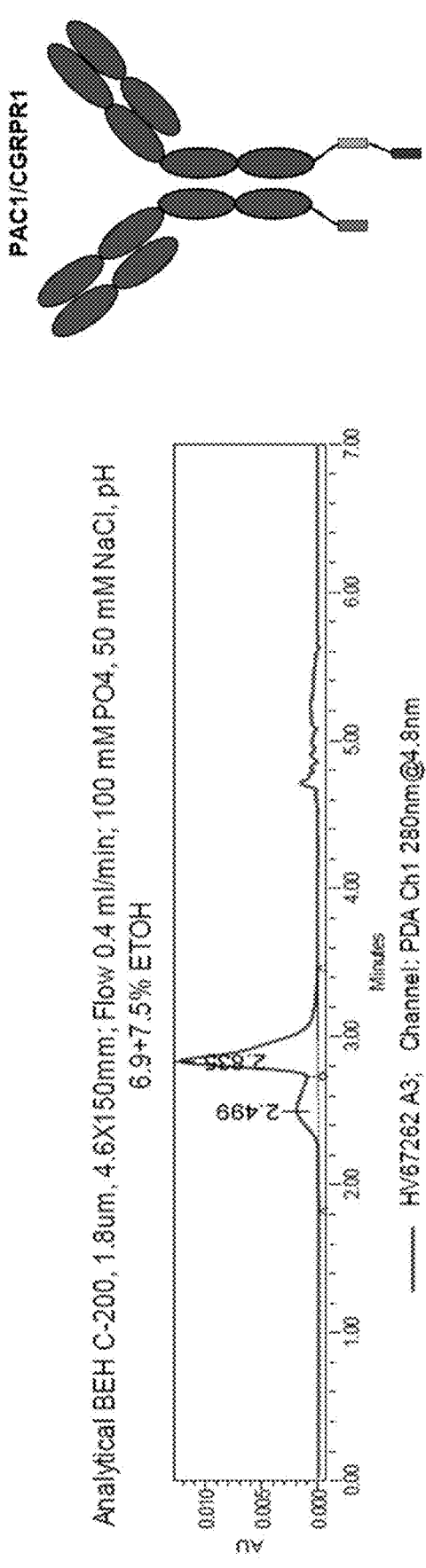
FIG. 17 depicts UPLC: Analytical Sec Profile of PAC1/CGRPR1 After Pro A Purification.
Figure 18:
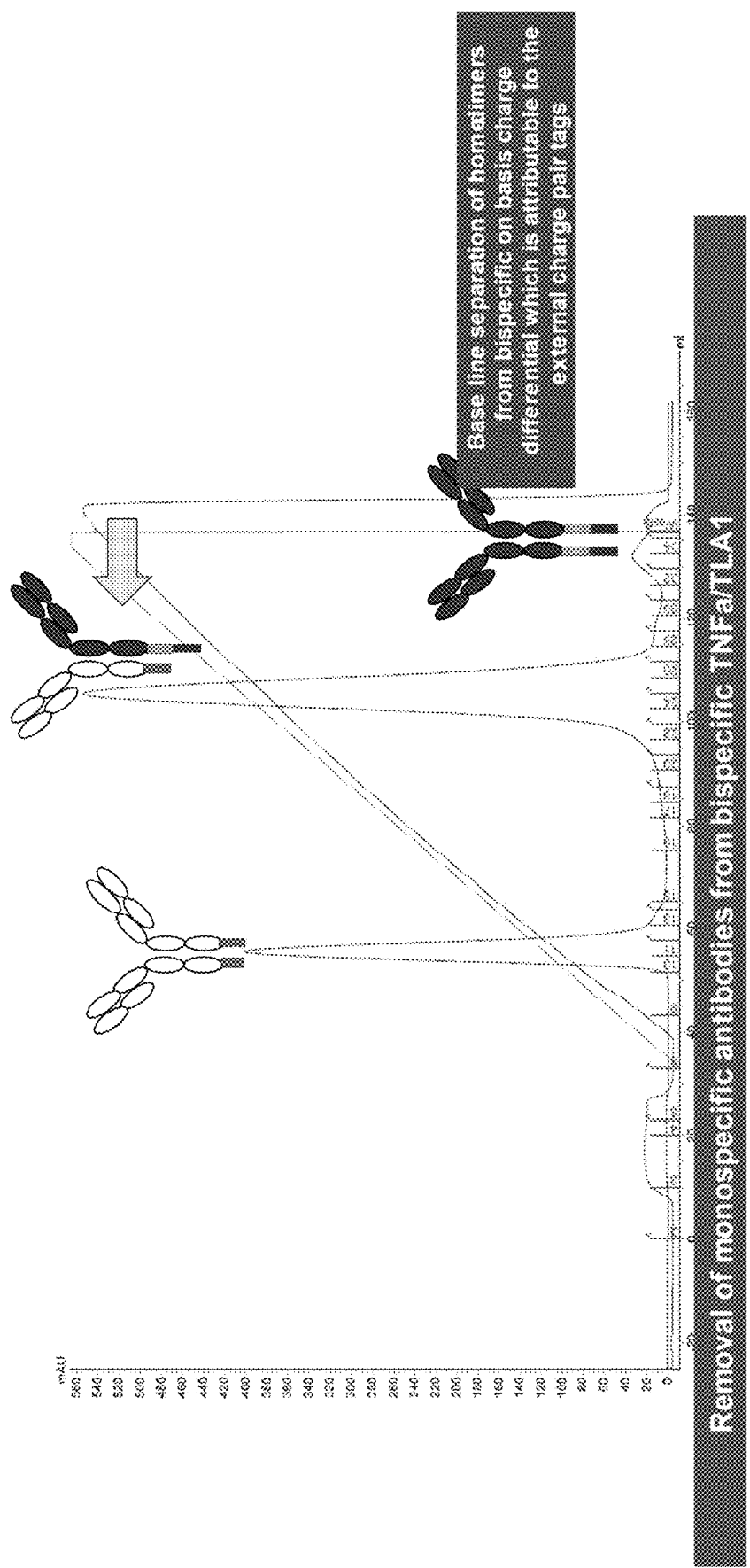
FIG. 18 depicts TNFα/TLA1: Preparative Cation Exchange Chromatography.
Figure 19:
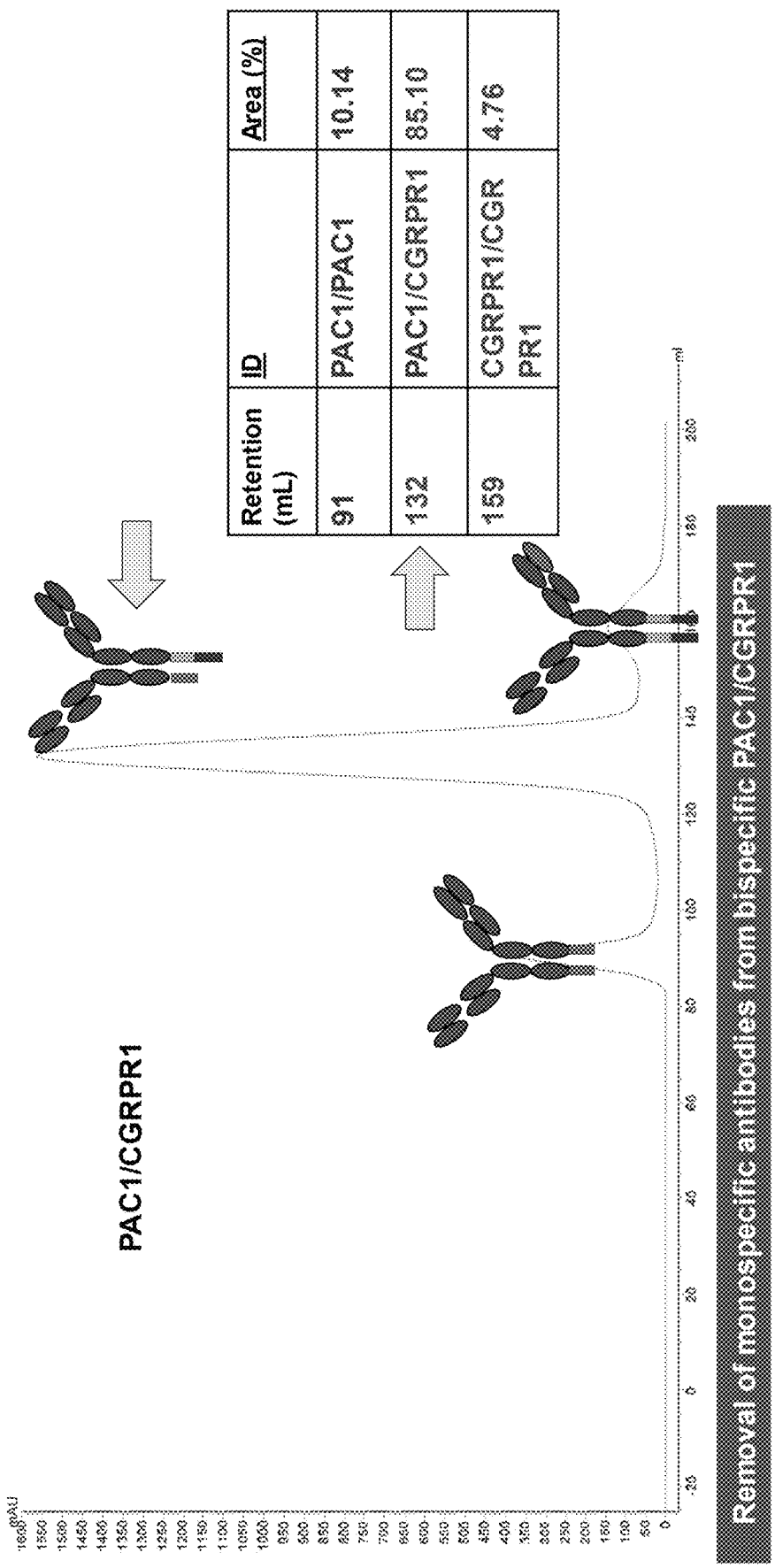
FIG. 19 depicts Preparative Cation Exchange Chromatography.
Figure 20:
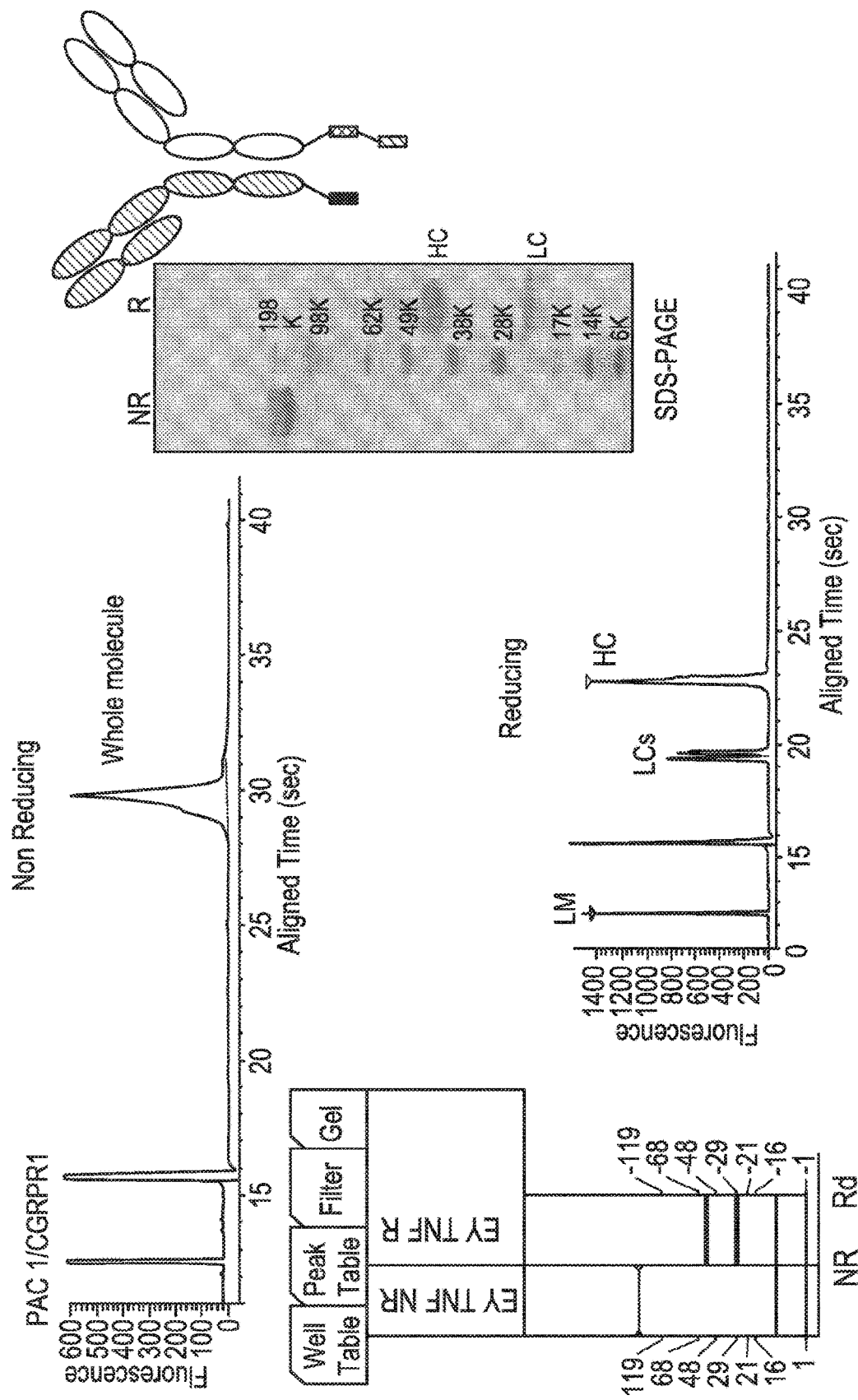
FIG. 20 depicts Caliper Analysis of PAC1/CGRPR1 Bispecific Antibody Produced by C-Terminal Charge Paired Tag.
Figure 21:
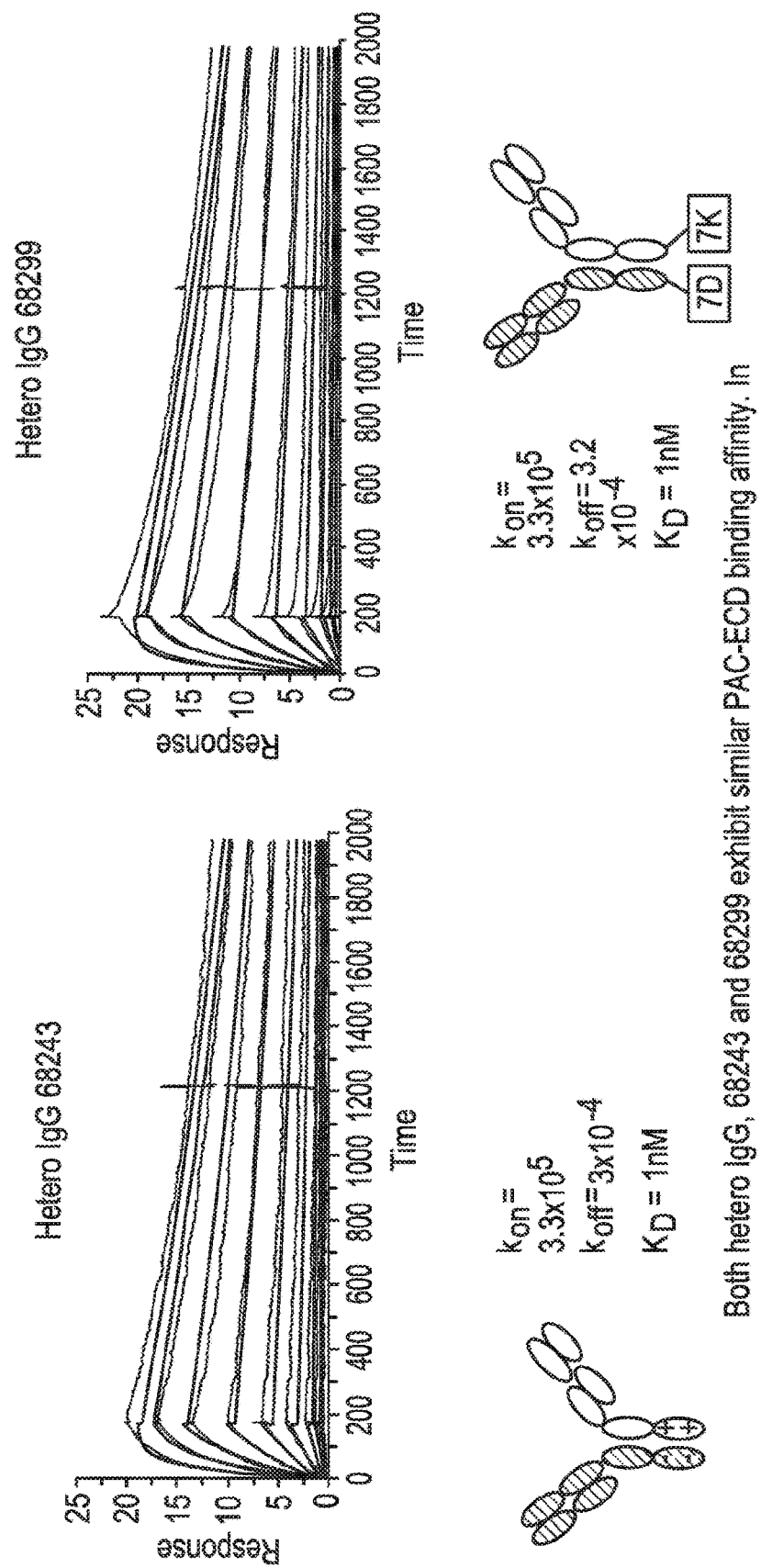
FIG. 21 depicts Bispecific PAC1/CGRPR1 Antibody Binding Analysis.
Figure 22:
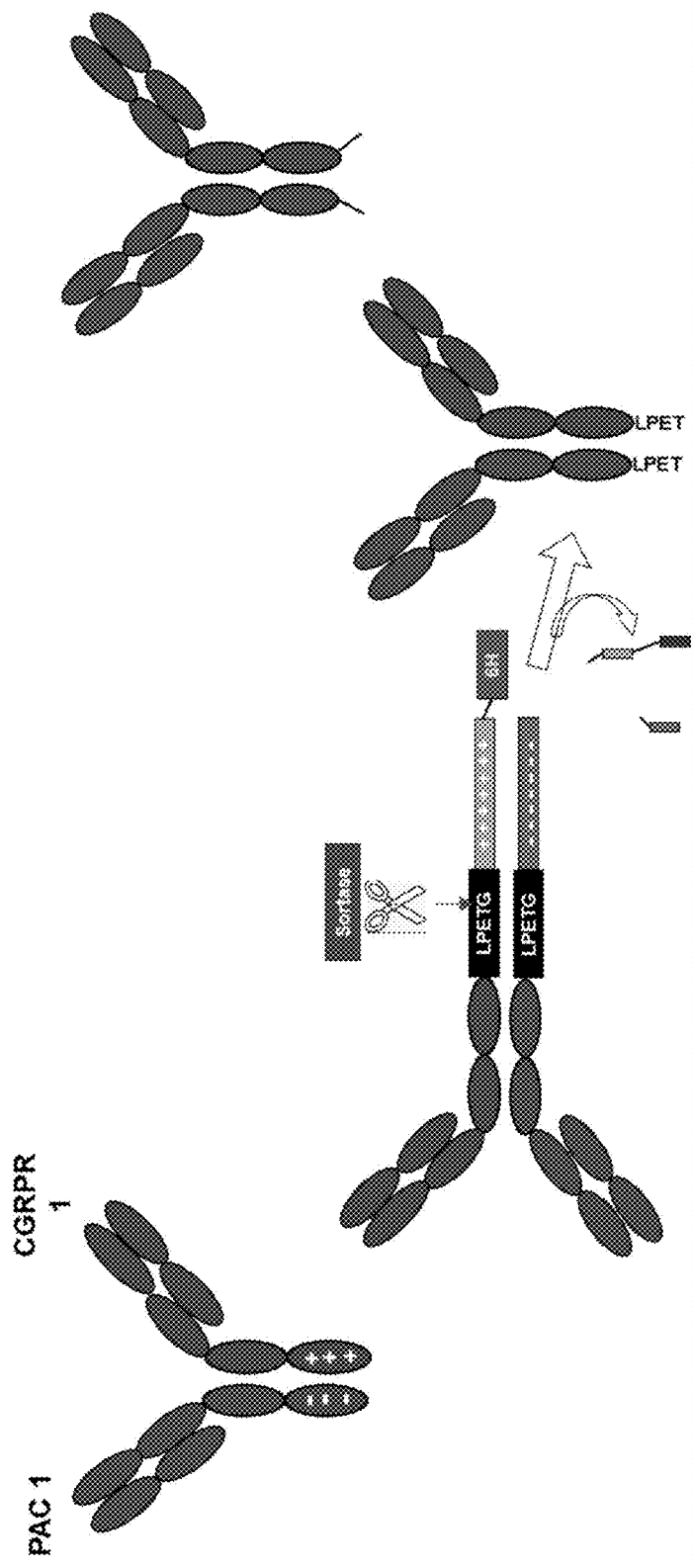
FIG. 22 depicts Site Specific Cleavage of C-Terminal Charge Paired Tags.
Figure 23:
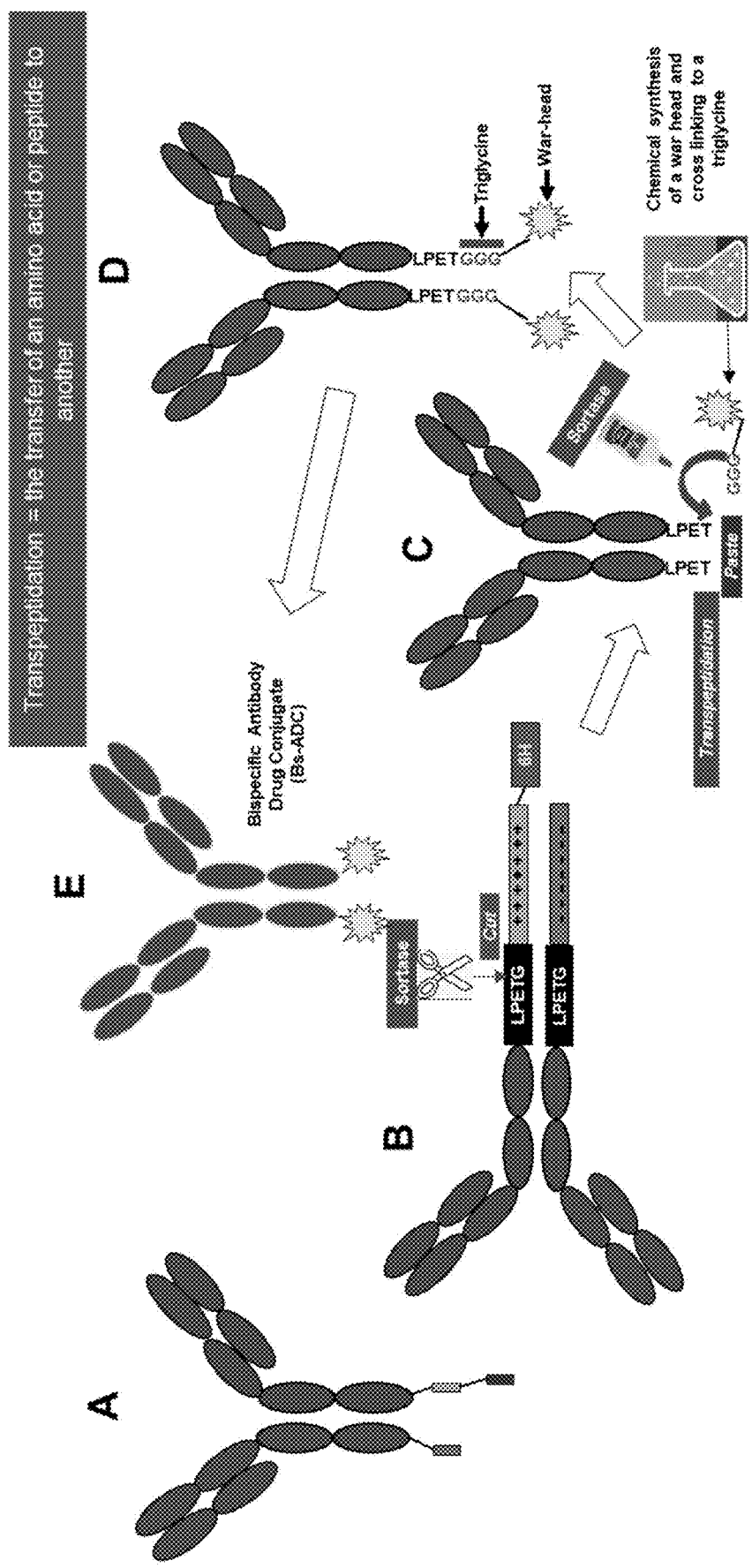
FIG. 23 depicts Site Specific Conjugation of Bispecific Antibody Through Transpeptidation.
Figure 24:
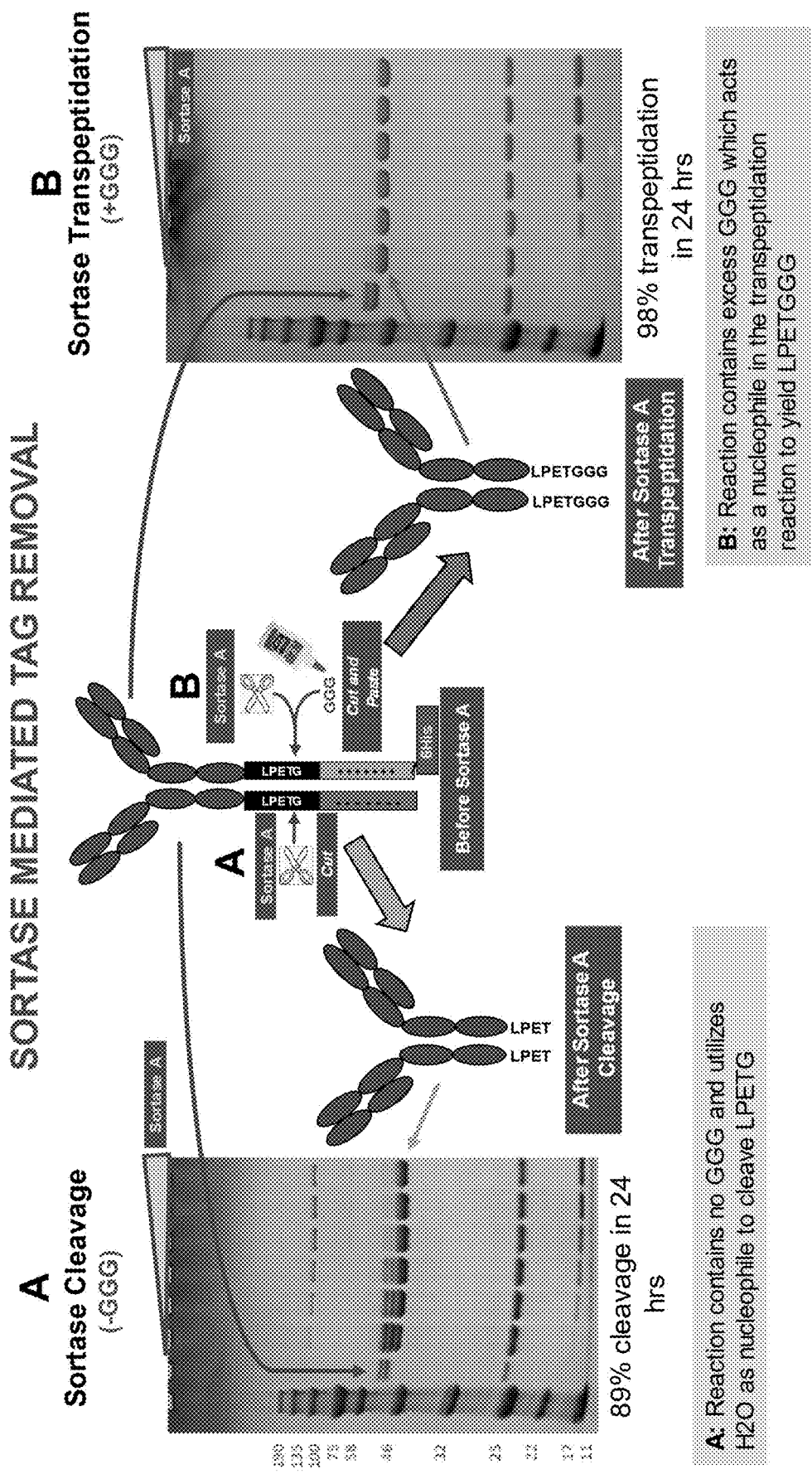
FIG. 24 depicts Sortase Mediated Tag Removal.
Figure 25:
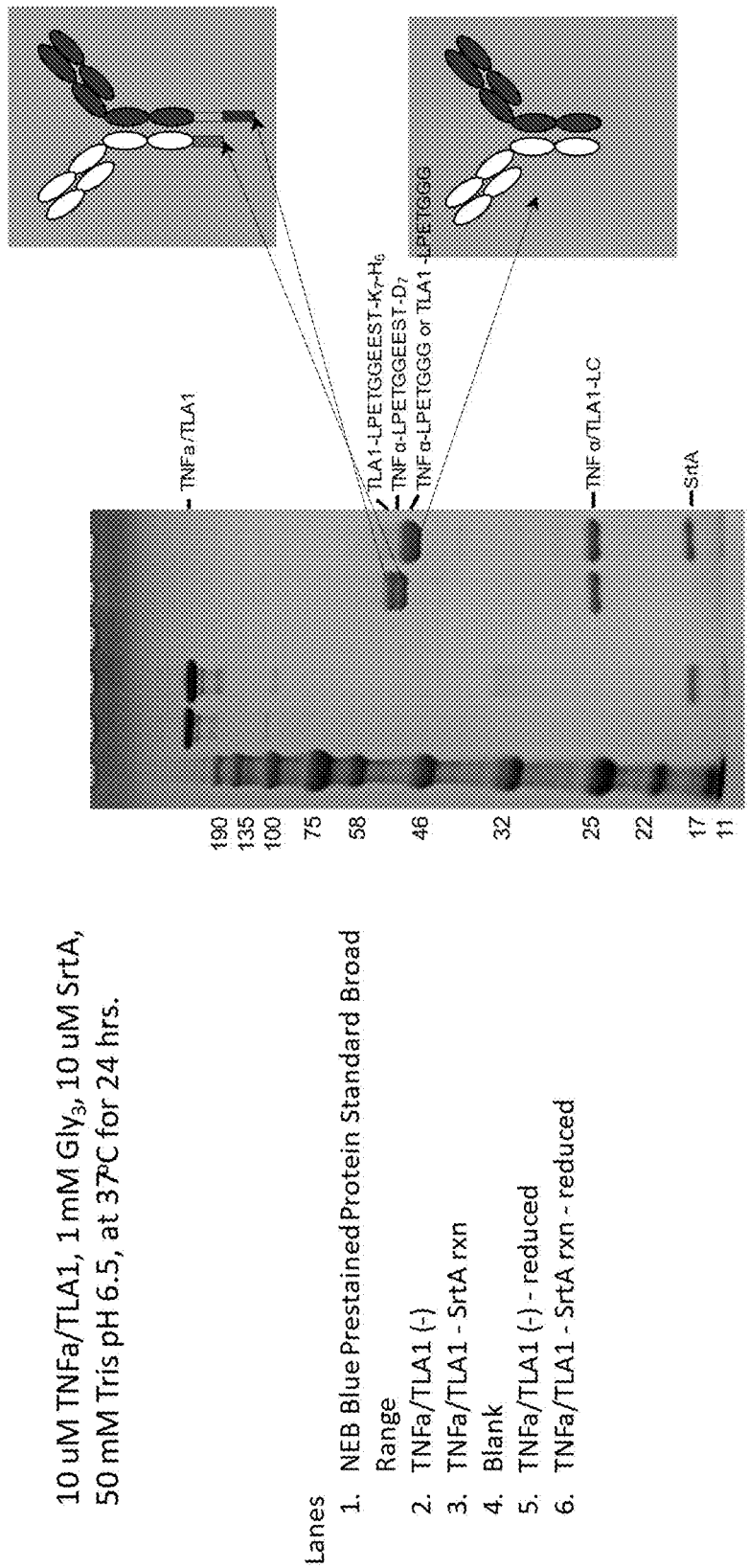
FIG. 25 depicts Large Scale Transpeptidation.
Figure 26:
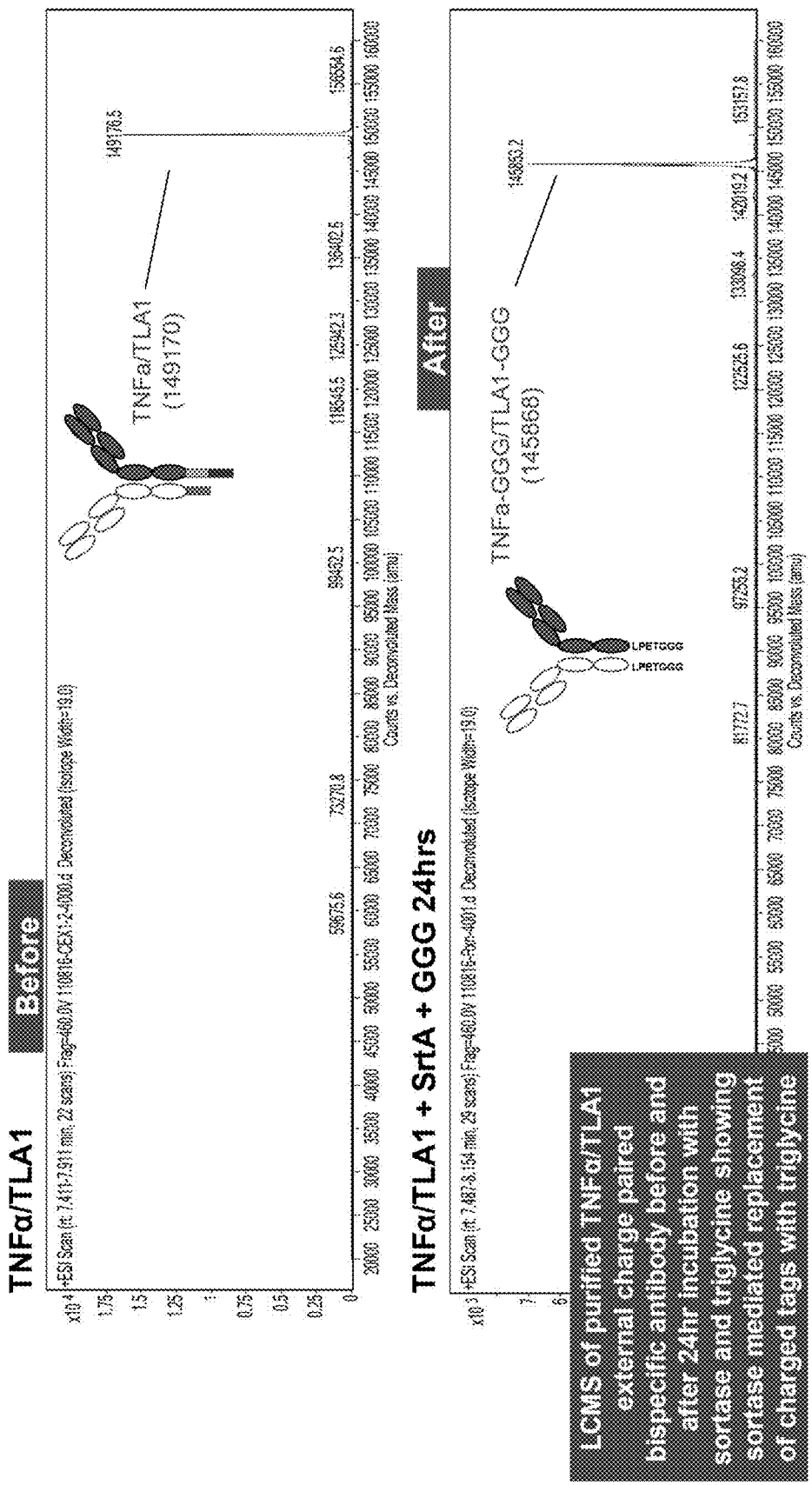
FIG. 26 depicts LCMS Removal of Charge Paired Tags from TNFα/TLA1.
Figure 27:
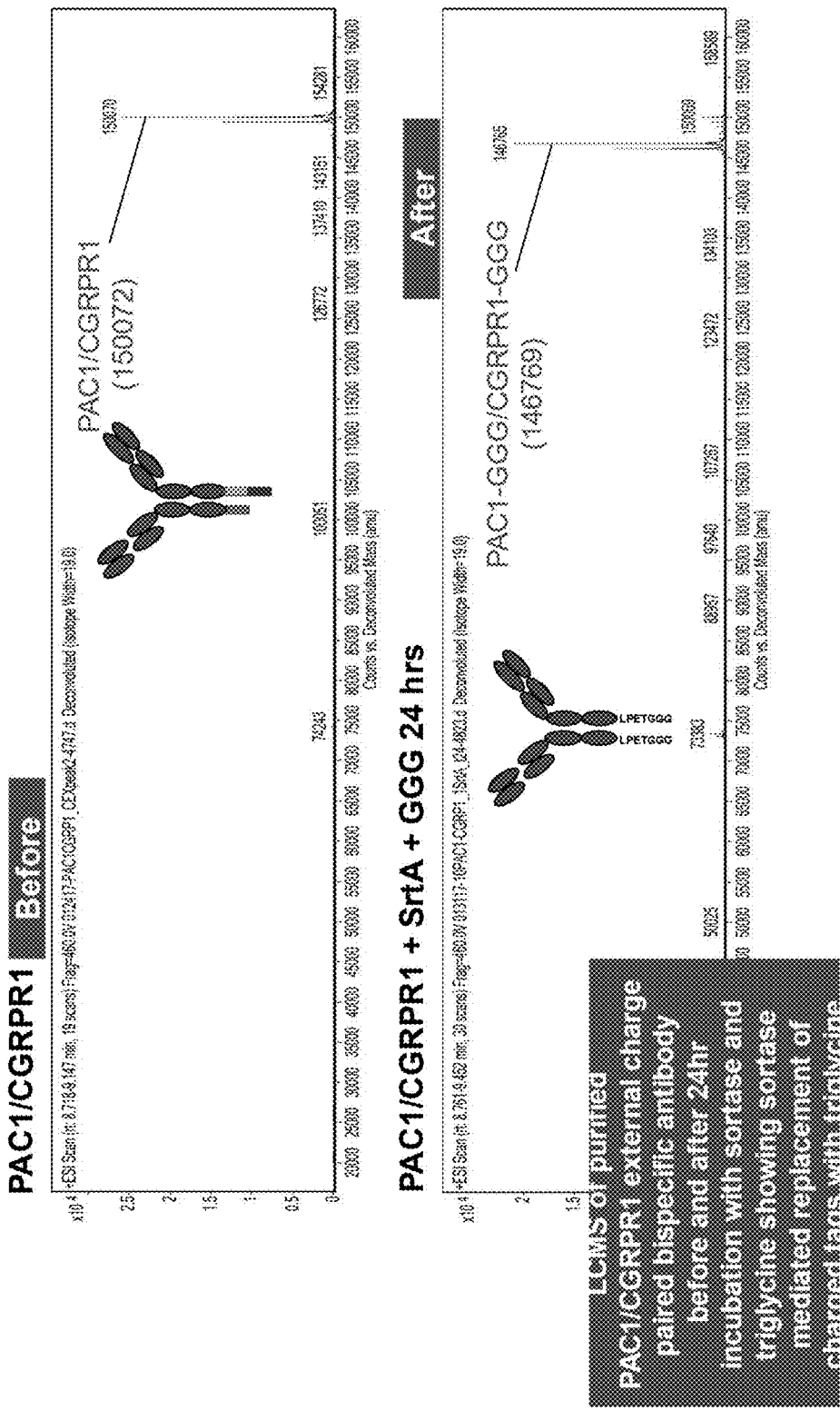
FIG. 27 depicts LCMS Removal of Charge Paired Tags from PAC1/CGRPR1.
Figure 28:
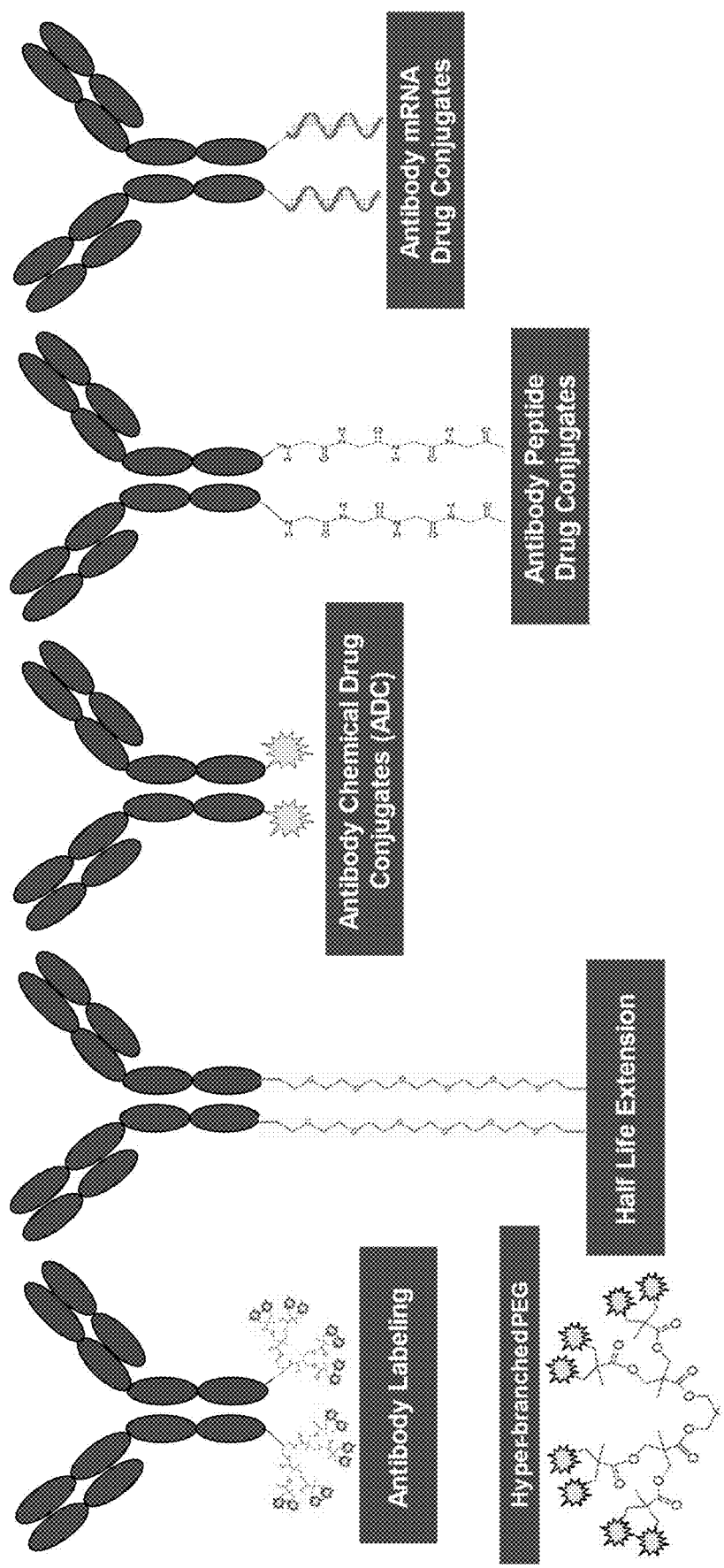
FIG. 28 depicts C-Terminal Conjugation of Charge-Pair Derived Bispecific Antibodies.
Figure 31:
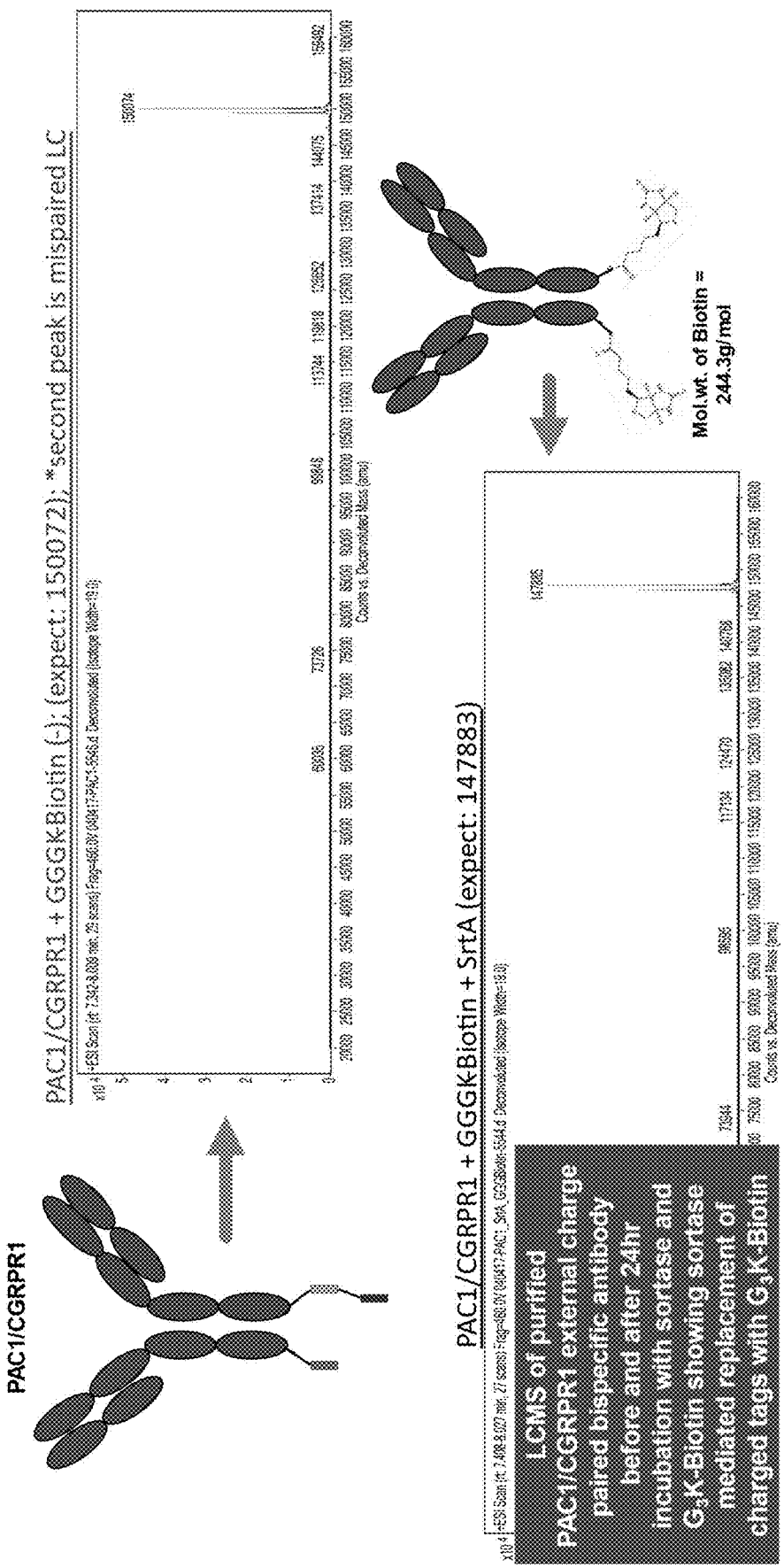
FIG. 31 depicts Sortase A Mediated Biotinylation of PAC1/CGRPR1.
Figure 32:
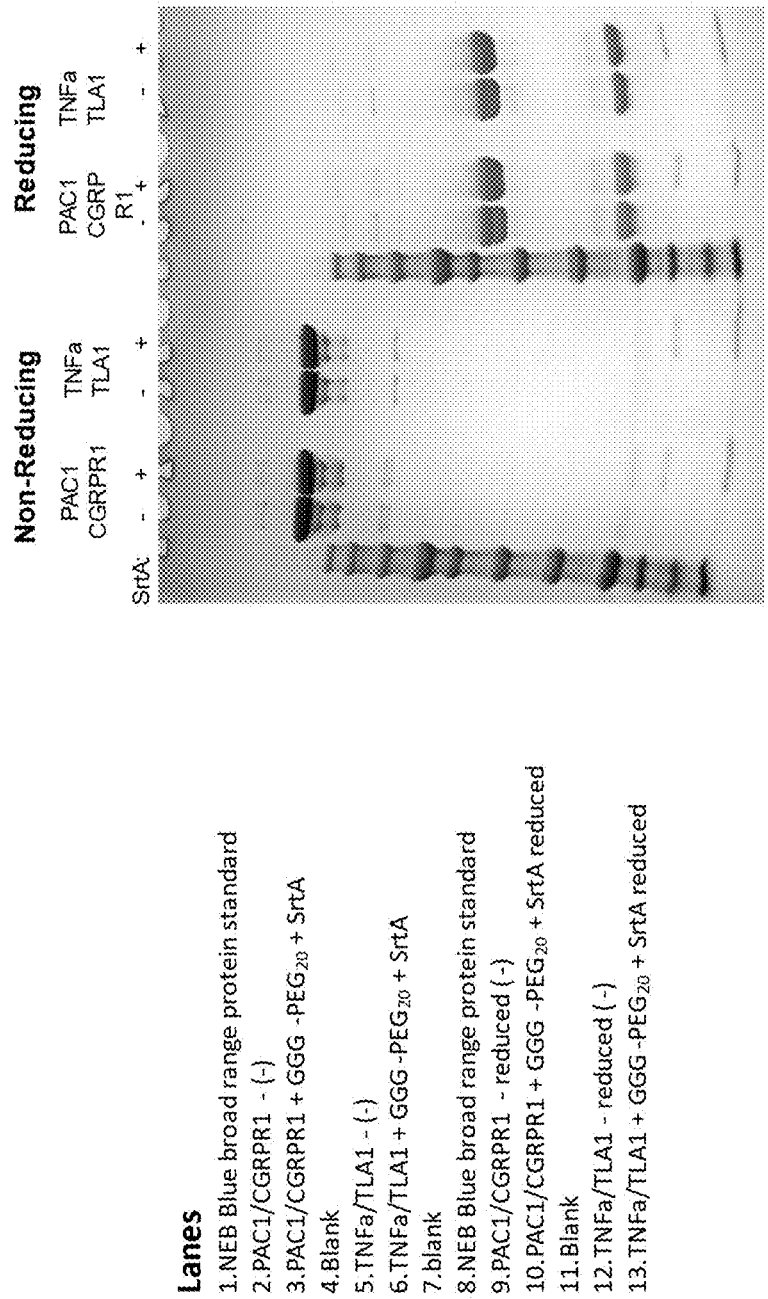
FIG. 32 depicts PEGylation of PAC1/CGRPR1 and TNFα/TLA1 Through Sortase A.
Figure 33:
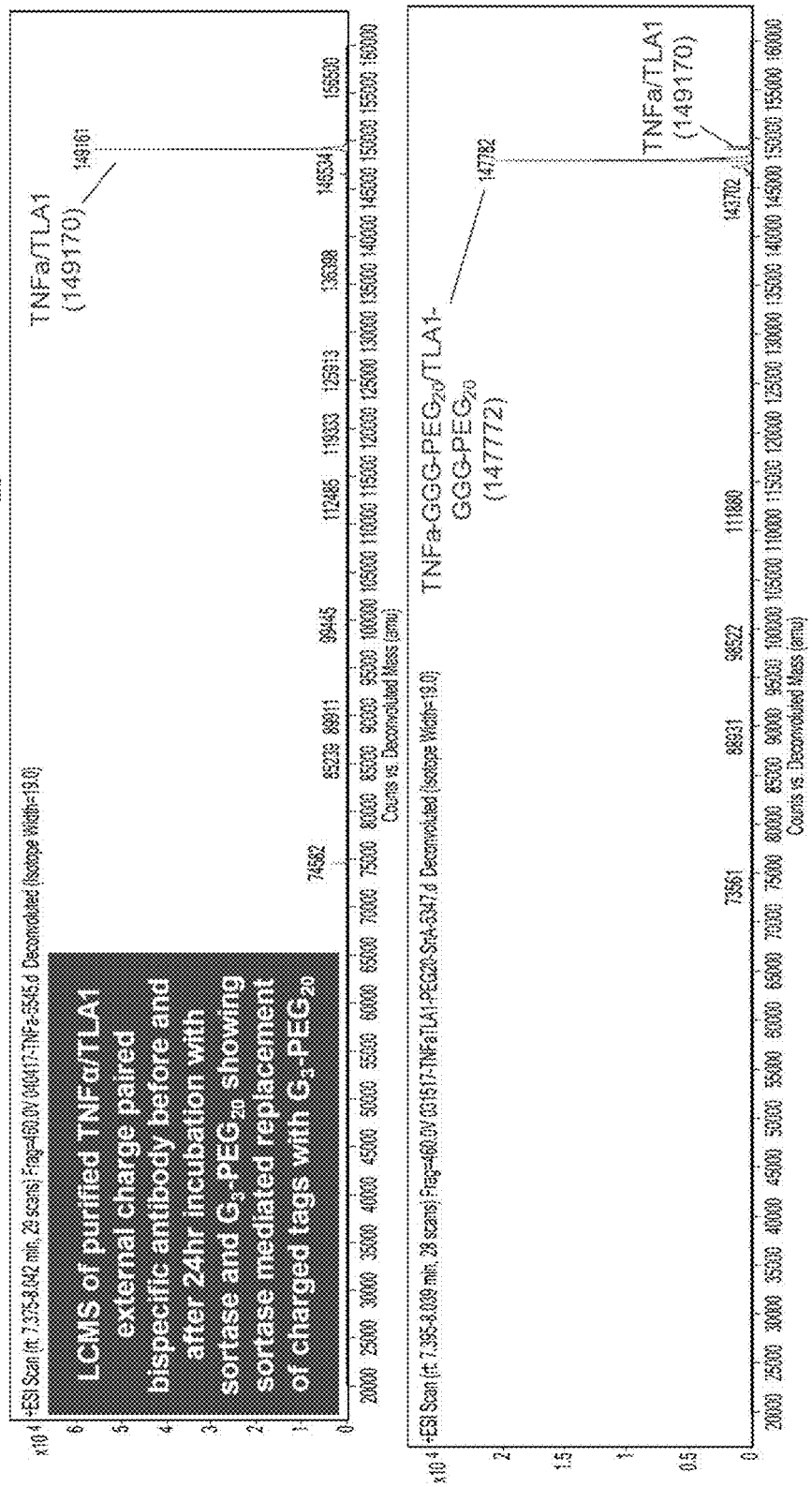
FIG. 33 depicts PEGylation of TNFα/TLA1 With GGG-PEG20 by Sortase A.
Figure 34:
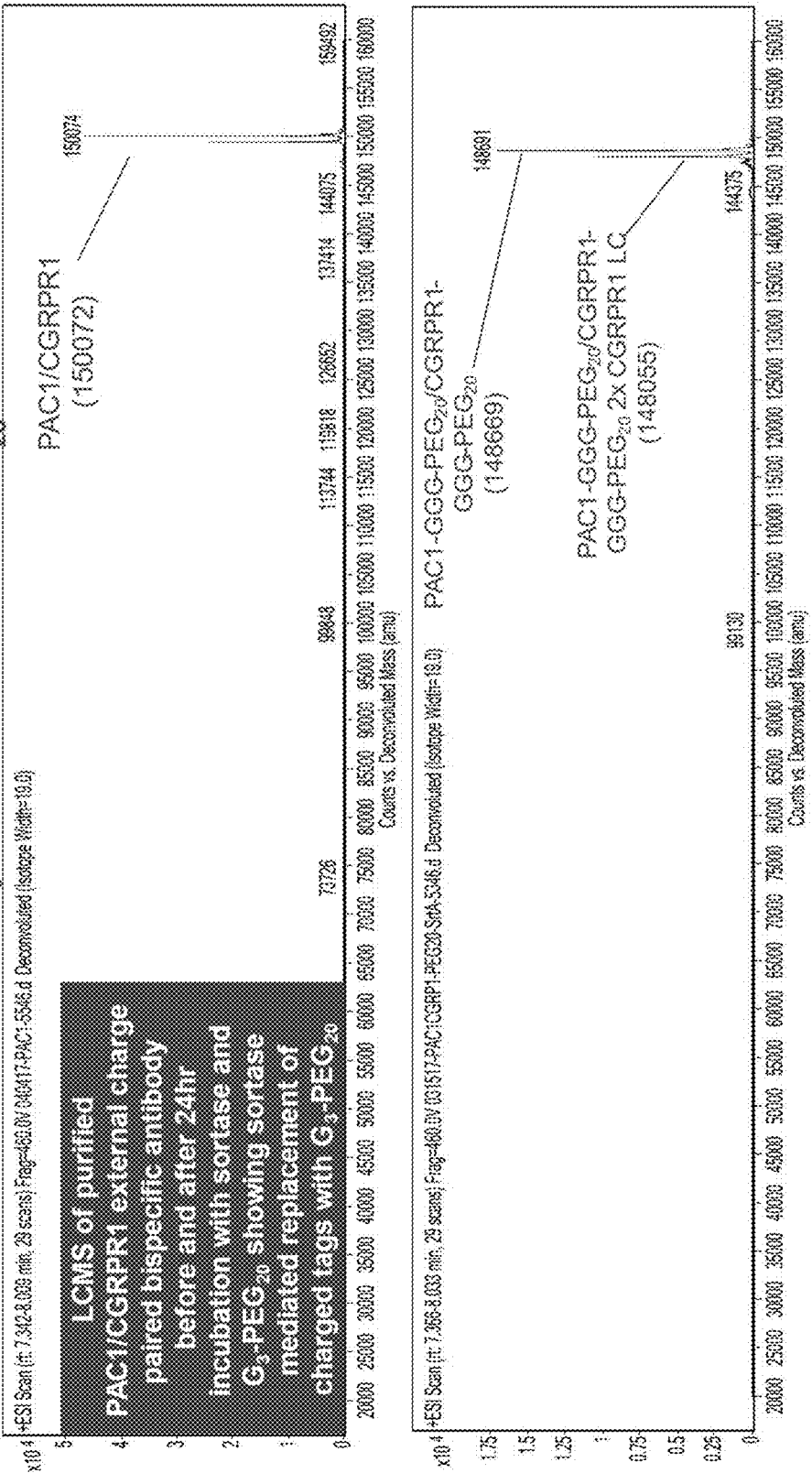
FIG. 34 depicts PEGylation of PAC1/CGRPR1 With GGG-PEG20 by Sortase A.
Figure 36:
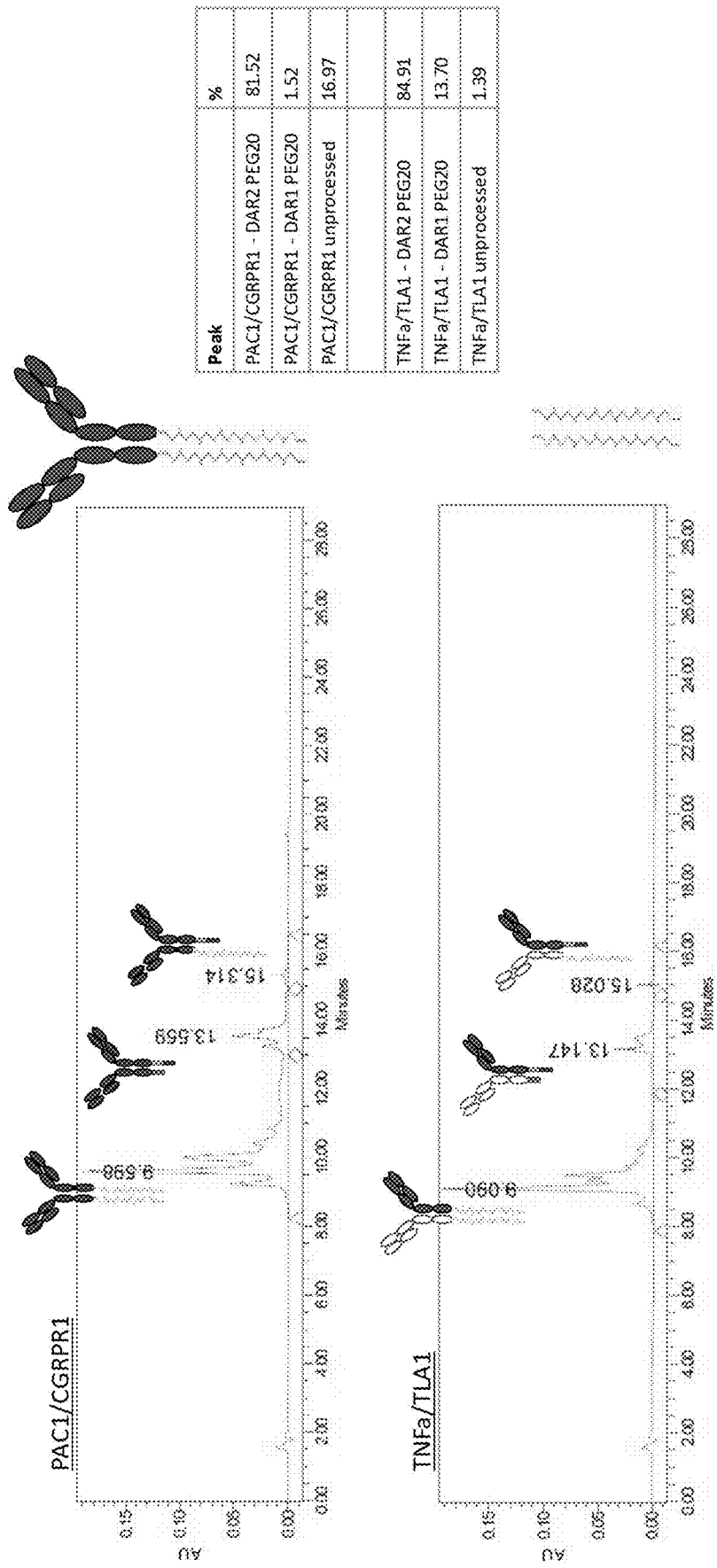
FIG. 36 depicts Analytical Cex of Bispecific Antibodies PEGylated With PEG20k.
Figure 37:
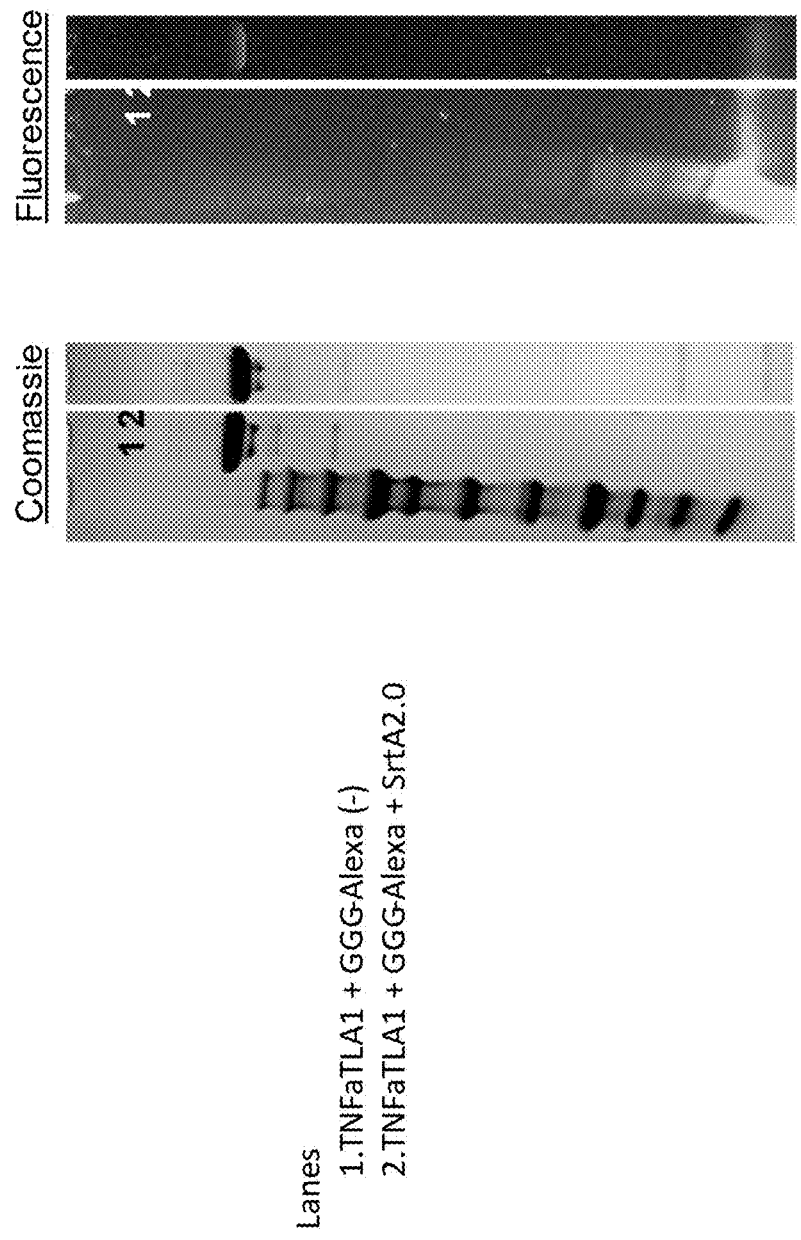
FIG. 37 depicts Site Specific Fusion of GGG-Alexa Fluorophore by Sortase A—TNFα/TLA1.
Figure 38:
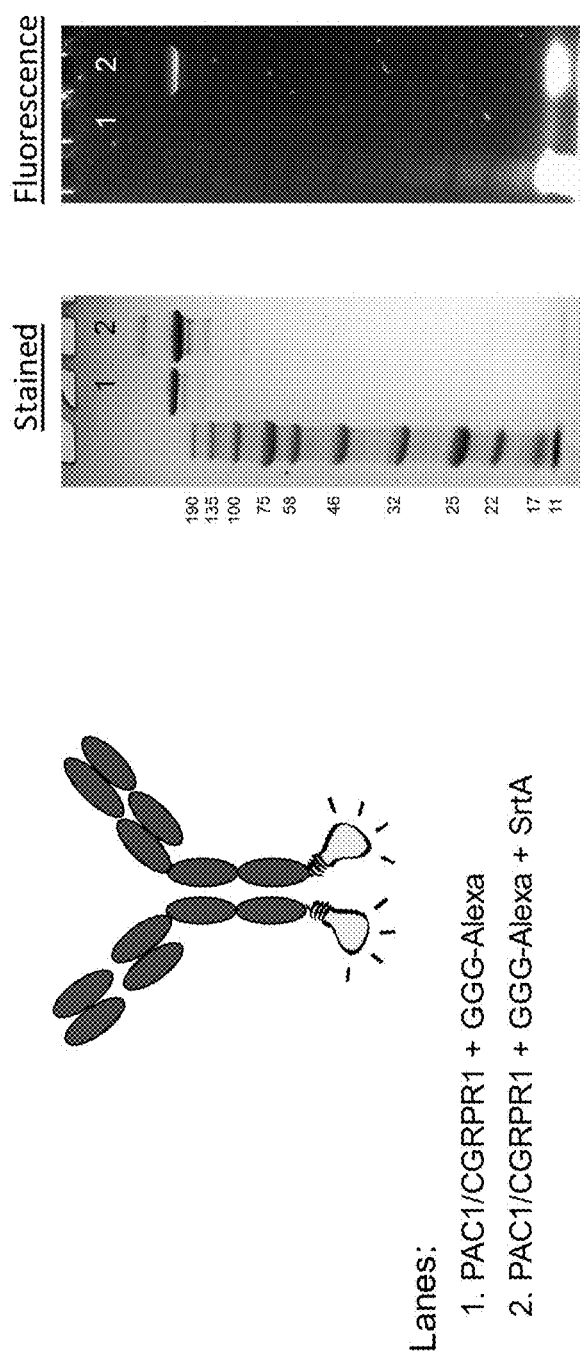
FIG. 38 depicts Site Specific Conjugation of -GGG-Alexa Fluorophore by Sortase A —PAC1/CGRPR1.
Figure 39:
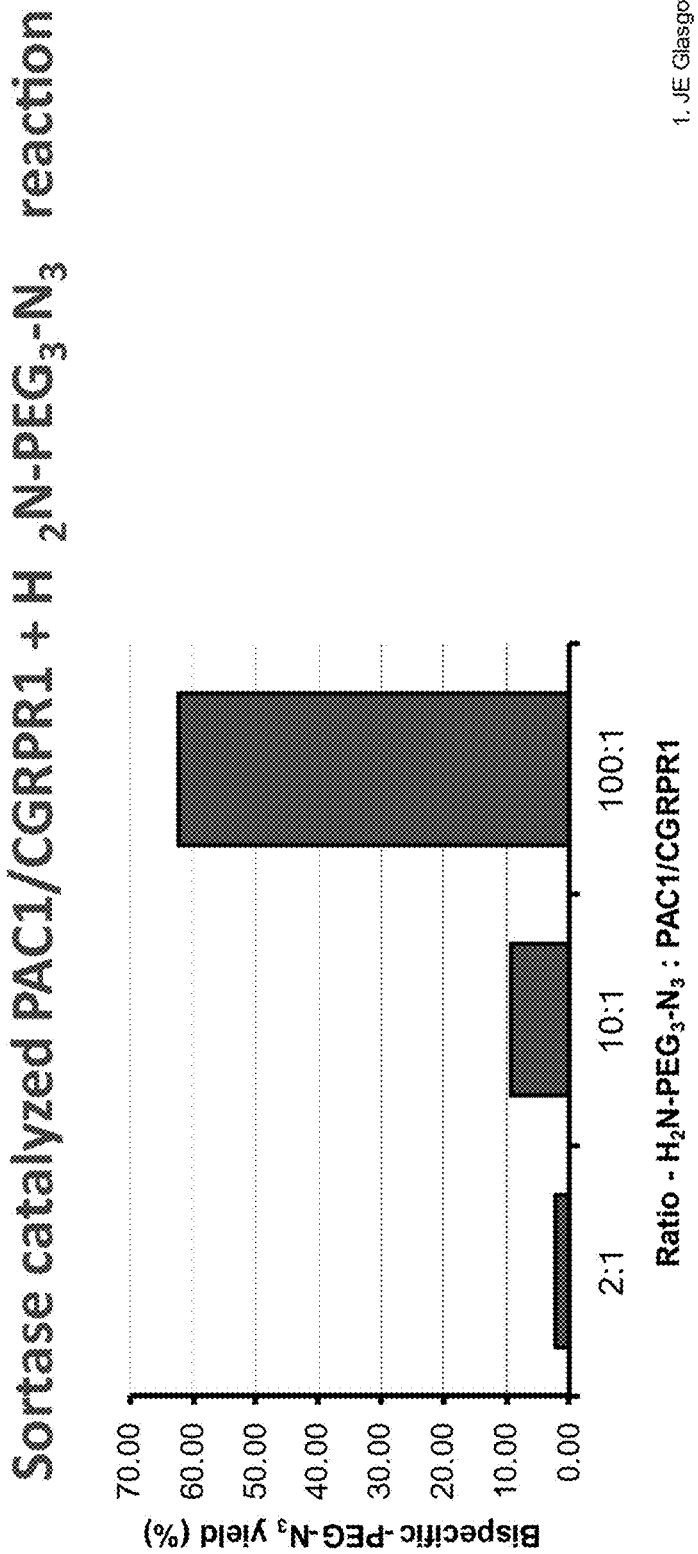
FIG. 39 depicts Sortase Can Also Utilize Non-Canonical Nucleophiles.

Without being bound by theory, applicants believe that the C-terminal charge pair tags described herein provide the initial trigger that drives the binding of two or more molecules together with a high degree of accuracy and efficiency surprisingly even in the presence of Fc regions of an immunoglobulin, which Fc regions are also naturally attracted to each other under cell culture conditions.

By reducing homodimerization of heavy chains, use of the oppositely charged C-terminal charge pair tags described herein provides a breakthrough in the ability to produce a homogeneous population of protein complexes comprising a CH3, CH2-CH3, or hinge-CH2-CH3 component (e.g., multi-specific or one-armed antibodies, etc.). Multi-specific complexes are advantageous for use in therapeutic applications because, for example, they can direct the co-localization of a target (e.g., a tumor cell) and an agent directed against the target (e.g., a T cell) or they can eliminate the need for combination therapy and the risk associated with providing two or more therapeutics to a subject. Further, proteases can be used to facilitate the removal of the C-terminal charge pair tags from the heterodimer.

Recombinant polypeptide and nucleic acid methods used herein, including in the Examples, are generally those set forth in Sambrook et al., Molecular Cloning: A Laboratory Manual (Cold Spring Harbor Laboratory Press, 1989) or Current Protocols in Molecular Biology (Ausubel et al., eds., Green Publishers Inc. and Wiley and Sons 1994), both of which are incorporated herein by reference for any purpose.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean ±1%.

Following convention, as used herein "a" and "an" mean "one or more" unless specifically indicated otherwise.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

A "naturally occurring amino acid" is an amino acid that is encoded by the genetic code, as well as those amino acids that are encoded by the genetic code that are modified after synthesis, e.g., hydroxyproline, γ-carboxyglutamate, and O-phosphoserine. An amino acid analog is a compound that has the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

An "amino acid mimetic" is a chemical compound that has a structure that is different from the general chemical structure of an amino acid, but that functions in a manner similar to a naturally occurring amino acid. Examples include a methacryloyl or acryloyl derivative of an amide, β-, γ-, δ-amino acids (such as piperidine-4-carboxylic acid) and the like.

A "non-naturally occurring amino acid" is a compound that has the same basic chemical structure as a naturally occurring amino acid, but is not incorporated into a growing polypeptide chain by the translation complex. "Non-naturally occurring amino acid" also includes, but is not limited to, amino acids that occur by modification (e.g., posttranslational modifications) of a naturally encoded amino acid (including but not limited to, the 20 common amino acids) but are not themselves naturally incorporated into a growing polypeptide chain by the translation complex. A non-limiting lists of examples of non-naturally occurring amino acids that can be inserted into a polypeptide sequence or substituted for a wild-type residue in polypeptide sequence include β-amino acids, homoamino acids, cyclic amino acids and amino acids with derivatized side chains. Examples include (in the L-form or D-form; abbreviated as in parentheses): citrulline (Cit), homocitrulline (hCit), Na-methylcitrulline (NMeCit), Na-methylhomocitrulline (Na-MeHoCit), ornithine (Orn), Na-Methylornithine (Na-MeOrn or NMeOrn), sarcosine (Sar), homolysine (hLys or hK), homoarginine (hArg or hR), homoglutamine (hQ), Na-methylarginine (NMeR), Na-methylleucine (Na-MeL or NMeL), N-methylhomolysine (NMeHoK), Na-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl) alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Na-methyl valine (NMeVal), N-α-methyl leucine (NMeLeu), Na-methylnorleucine (NMeNle), cyclopentylglycine (Cpg), cyclohexylglycine (Chg), acetylarginine (acetylarg), α, β-diaminopropionoic acid (Dpr), α, γ-diaminobutyric acid (Dab), diaminopropionic acid (Dap), cyclohexylalanine (Cha), 4-methyl-phenylalanine (MePhe), β, β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

The term "isolated nucleic acid molecule" refers to a single or double-stranded polymer of deoxyribonucleotide or ribonucleotide bases read from the 5' to the 3' end or an analog thereof, that has been separated from at least about 50 percent of polypeptides, peptides, lipids, carbohydrates, polynucleotides or other materials with which the nucleic acid is naturally found when total nucleic acid is isolated from the source cells. Preferably, an isolated nucleic acid molecule is substantially free from any other contaminating nucleic acid molecules or other molecules that are found in the natural environment of the nucleic acid that would interfere with its use in polypeptide production or its therapeutic, diagnostic, prophylactic or research use.

The term "isolated polypeptide" refers to a polypeptide that has been separated from at least about 50 percent of polypeptides, peptides, lipids, carbohydrates, polynucleotides, or other materials with which the polypeptide is naturally found when isolated from a source cell. Preferably, the isolated polypeptide is substantially free from any other contaminating polypeptides or other contaminants that are found in its natural environment that would interfere with its therapeutic, diagnostic, prophylactic or research use.

The term "encoding" refers to a polynucleotide sequence encoding one or more amino acids. The term does not require a start or stop codon.

The terms "identical" and percent "identity," in the context of two or more nucleic acids or polypeptide sequences, refer to two or more sequences or subsequences that are the same. "Percent identity" means the percent of identical residues between the amino acids or nucleotides in the compared molecules and is calculated based on the size of the smallest of the molecules being compared. For these calculations, gaps in alignments (if any) can be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) SIAM J. Applied Math. 48:1073.

In calculating percent identity, the sequences being compared are aligned in a way that gives the largest match between the sequences. The computer program used to determine percent identity is the GCG program package, which includes GAP (Devereux et al., (1984) Nucl. Acid Res. 12:387; Genetics Computer Group, University of Wisconsin, Madison, WI). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3x the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, J. Mol. Biol. 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

An "antigen binding protein" as used herein means any protein that specifically binds a specified target antigen. The term encompasses intact antibodies that comprise at least two full-length heavy chains and two full-length light chains, as well as derivatives, variants, fragments, and mutations thereof. Examples of antibody fragments include Fab, Fab', F(ab') 2, and Fv fragments. An antigen binding protein also includes domain antibodies such as nanobodies and scFvs as described further below.

In general, an antigen binding protein is the to "specifically bind" its target antigen when the antigen binding protein exhibits essentially background binding to non-target antigen molecules. An antigen binding protein that specifically binds its target antigen may, however, cross-react with target antigen polypeptides from different species. Typically, an antigen binding protein specifically binds its target antigen when the dissociation constant (KD) is $\leq 10^{-7}$ M as measured via a surface plasma resonance technique (e.g., BIACore, GE-Healthcare Uppsala, Sweden) or Kinetic Exclusion Assay (KinExA, Sapidyne, Boise, Idaho). An antigen binding protein specifically binds its target antigen with "high affinity" when the KD is $\leq 5\times 10^{-9}$ M, and with "very high affinity" when the KD is $\leq 5\times 10^{-10}$ M, as measured using methods described.

"Antigen binding region" means a protein, or a portion of a protein, that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs") of an immunoglobulin, single-chain immunoglobulin, or camelid antibody. Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen.

A "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and multi-specific antibodies. An "antibody" as such is a species of an antigen binding protein. An intact antibody generally will comprise at least two full-length heavy chains and two full-length light chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies.

The term "light chain" as used with respect to an antibody or fragments thereof includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" as used with respect to an antibody or fragment thereof includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains may be of any isotype, including IgG (including IgG1, IgG2, IgG3 and IgG4 subtypes), IgA (including IgA1 and IgA2 subtypes), IgM and IgE.

The term "immunologically functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope.

These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', and F(ab') 2 fragments.

In another embodiment, Fvs, domain antibodies and scFvs, and may be derived from an antibody of the present invention.

It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

A "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

An "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form an F(ab') 2 molecule.

An "F(ab') 2 fragment" contains two light chains and two heavy chains containing a portion of the constant region between the CH1 and CH2 domains, such that an interchain disulfide bond is formed between the two heavy chains. A F(ab') 2 fragment thus is composed of two Fab' fragments that are held together by a disulfide bond between the two heavy chains.

The "Fv region" comprises the variable regions from both the heavy and light chains, but lacks the constant regions.

"Single chain antibodies" or "scFvs" are Fv molecules in which the heavy and light chain variable regions have been connected by a flexible linker to form a single polypeptide chain, which forms an antigen-binding region. scFvs are discussed in detail in International Patent Application Publication No. WO 88/01649 and U.S. Pat. Nos. 4,946,778 and 5,260,203, the disclosures of which are incorporated by reference.

A "domain antibody" or "single chain immunoglobulin" is an immunologically functional immunoglobulin fragment containing only the variable region of a heavy chain or the variable region of a light chain. Examples of domain antibodies include Nanobodies®. In some instances, two or more VH regions are covalently joined with a peptide linker to create a bivalent domain antibody. The two VH regions of a bivalent domain antibody may target the same or different antigens.

A "bivalent antigen binding protein" or "bivalent antibody" comprises two antigen binding regions. In some instances, the two binding regions have the same antigen specificities. Bivalent antigen binding proteins and bivalent antibodies may be bispecific, see, infra.

A multi-specific antigen binding protein" or "multi-specific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multi-specific antigen binding protein or multi-specific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which may reside on the same or different protein targets.

The term "compete" when used in the context of antigen binding proteins (e.g., antibodies) means competition between antigen binding proteins is determined by an assay in which the antigen binding protein (e.g., antibody or immunologically functional fragment thereof) under test prevents or inhibits specific binding of a reference antigen binding protein to a common antigen. Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Additional details regarding methods for determining competitive binding are provided in the examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instances, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody. An epitope can be contiguous or non-contiguous (discontinuous) (e.g., in a polypeptide, amino acid residues that are not contiguous to one another in the polypeptide sequence but that within in context of the molecule are bound by the antigen binding protein). A conformational epitope is an epitope that exists within the conformation of an active protein but is not present in a denatured protein. In certain embodiments, epitopes may be mimetic in that they comprise a three-dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three-dimensional structural characteristics, and/or specific charge characteristics. Generally, antigen binding proteins specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, 96%, 97%, 98%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequences. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed with a nucleic acid sequence and thereby expresses a gene of interest. The term includes the progeny of the parent cell, whether or not the progeny is identical in morphology or in genetic make-up to the original parent cell, so long as the gene of interest is present.

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass antigen binding proteins, antibodies, or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antigen binding protein such as an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein such as an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

A "subject" or "patient" as used herein can be any mammal. In a typical embodiment, the subject or patient is a human.

A "conservative amino acid substitution" can involve a substitution of a native amino acid residue (i.e., a residue found in a given position of a polypeptide sequence) with a nonnative residue (i.e., a residue that is not found in the same given position of the polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Additional groups of amino acids can also be formulated using the principles described in, e.g., Creighton (1984) PROTEINS: STRUCTURE AND MOLECULAR PROPERTIES (2d Ed. 1993), W.H. Freeman and Company. In some instances, it can be useful to further characterize substitutions based on two or more of such features (e.g., substitution with a "small polar" residue, such as a Thr residue, can represent a highly conservative substitution in an appropriate context).

Conservative substitutions can involve the exchange of a member of one of these classes for another member of the same class. Non-conservative substitutions can involve the exchange of a member of one of these classes for a member from another class.

Synthetic, rare, or modified amino acid residues having known similar physiochemical properties to those of an above-described grouping can be used as a "conservative" substitute for a particular amino acid residue in a sequence. For example, a D-Arg residue may serve as a substitute for a typical L-Arg residue. It also can be the case that a particular substitution can be described in terms of two or more of the above described classes (e.g., a substitution with a small and hydrophobic residue means substituting one amino acid with a residue(s) that is found in both of the above-described classes or other synthetic, rare, or modified residues that are known in the art to have similar physiochemical properties to such residues meeting both definitions).

In order to express a nucleic acid sequence, the appropriate coding sequence can be cloned into a suitable vector and after introduction in a suitable host, the sequence can be expressed to produce the encoded polypeptide according to standard cloning and expression techniques, which are known in the art (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989). The invention also relates to such vectors comprising a nucleic acid sequence according to the invention.

A "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a protein in prokaryotic (e.g., *E. coli*) or eukaryotic cells (e.g., insect cells, using baculovirus expression vectors, yeast cells, or mammalian cells). In one embodiment the host cell is a mammalian, non-human host cell. Representative host cells include those hosts typically used for cloning and expression, including *Escherichia coli* strains TOP10F', TOP10, DH10B, DH5a, HB101, W3110, BL21 (DE3) and BL21 (DE3) pLysS, BLUESCRIPT (Stratagene), mammalian cell lines CHO, CHO-K1, HEK293, 293-EBNA pIN vectors (Van Heeke & Schuster, J. Biol. Chem. 264:5503-5509 (1989); pET vectors (Novagen, Madison Wis.). Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the trp promoter.

A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EFialpha promoter, CAG promoter), effective poly (A) termination sequences, an origin of replication for plasmid product in *E. coli*, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding a polypeptide which is operatively linked to a tissue specific promoter which promotes expression of the sequence in a metabolically-relevant tissue, such as liver or pancreatic tissue is provided.

In another aspect of the instant disclosure, host cells comprising the nucleic acids and vectors disclosed herein are provided. In various embodiments, the vector or nucleic acid is integrated into the host cell genome, which in other embodiments the vector or nucleic acid is extra-chromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments cells comprising a non-integrated nucleic acid, such as a plasmid, cosmid, phagemid, or linear expression element, which comprises a sequence coding for expression of a polypeptide, are provided.

A vector comprising a nucleic acid sequence encoding a polypeptide provided herein can be introduced into a host cell by transformation or by transfection. Methods of transforming a cell with an expression vector are well known.

A nucleic acid can be positioned in and/or delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a polypeptide-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

Protein purification methods that can be employed to isolate a polypeptide, as well as associated materials and reagents, are known in the art. Additional purification methods that may be useful for isolating a polypeptide can be found in references such as Bootcov MR, 1997, Proc. Natl. Acad. Sci. USA 94:11514-9, Fairlie WD, 2000, Gene 254: 67-76.

The antigen binding proteins provided are polypeptides into which one or more complementary determining regions (CDRs), as described herein, are embedded and/or joined. In some antigen binding proteins, the CDRs are embedded into a "framework" region, which orients the CDR(s) such that the proper antigen binding properties of the CDR(s) are achieved. Certain antigen binding proteins described herein are antibodies or are derived from antibodies. In other antigen binding proteins, the CDR sequences are embedded in a different type of protein scaffold. The various structures are further described below.

In general the antigen binding proteins that are provided typically comprise one or more CDRs as described herein (e.g., 1, 2, 3, 4, 5 or 6). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

In certain embodiments, the polypeptide structure of the antigen binding proteins is an antibody or is derived from an antibody. Accordingly, examples of certain antigen binding proteins that are provided include, but are not limited to, monoclonal antibodies, bispecific antibodies, minibodies, domain antibodies such as Nanobodies®, synthetic antibodies (sometimes referred to herein as "antibody mimetics"), chimeric antibodies, humanized antibodies, human antibodies, antibody fusions, and portions or fragments of each, respectively. In some instances, the antigen binding protein is an immunological fragment of a complete antibody (e.g., a Fab, a Fab', a F(ab')2). In other instances the antigen binding protein is a scFv that uses CDRs from an antibody of the present invention.

In one embodiment, an antigen binding protein has one or more of the following activities:

(a) binds target angien such that KD is ≤200 nM, is ≤150 nM, is ≤100 nM, is ≤50 nM, is ≤10 nM, is ≤5 nM, is ≤2 nM, or is ≤1 nM, e.g., as measured via a surface plasma resonance or kinetic exclusion assay technique.

(b) has a half-life in human serum of at least 3 days;

Some antigen binding proteins that are provided have an on-rate (ka) for target antigen of at least $10^4$/M x seconds, at least $10^5$/M x seconds, or at least $10^6$/M x seconds as measured, for instance, as described below. Certain antigen binding proteins that are provided have a slow dissociation rate or off-rate. Some antigen binding proteins, for instance, have a kd (off-rate) of $1X\ 10^{-2}\ s^{-1}$, or $1x\ 10^{-3}\ s^{-1}$, or $1x\ 10^{-4}\ s^{-1}$, or $1x\ 10^{-5}\ s^{-1}$. In certain embodiments, the antigen binding protein has a KD (equilibrium binding affinity) of less than 25 pM, 50 pM, 100 pM, 500 pM, 1 nM, 5 nM, 10 nM, 25 nM or 50 nM.

In another aspect, an antigen-binding protein is provided having a half-life of at least one day in vitro or in vivo (e.g., when administered to a human subject). In one embodiment, the antigen binding protein has a half-life of at least three days. In various other embodiments, the antigen binding protein has a half-life of 4, 5, 6, 7, 8, 9, 10, 15, 20, 25, 30, 40, 50, or 60 days or longer. In another embodiment, the antigen binding protein is derivatized or modified such that it has a longer half-life as compared to the underivatized or unmodified antibody. In another embodiment, the antigen binding protein contains point mutations to increase serum half-life. Further details regarding such mutant and derivatized forms are provided below.

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as CH1, CH2 and CH3. The antibodies that are provided can have any of these isotypes and subtypes. In certain embodiments, the antibody is of the IgG1, IgG2, or IgG4 subtype.

In full-length light and heavy chains, the variable and constant regions are joined by a "J" region of about twelve or more amino acids, with the heavy chain also including a "D" region of about ten more amino acids. See, e.g. Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

For the antibodies provided herein, the variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on target antigen. From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, J. Mol. Biol. 196:901-917; Chothia et al., 1989, Nature 342:878-883.

That being the, both the EU index as in Kabat et al., Sequences of Proteins of Immunological Interest, 5th Ed. Public Health Service, National Institutes of Health, Bethesda, MD (1991) and AHo numbering schemes (Honegger A. and Plückthun A. J Mol Biol. 2001 Jun. 8;309 (3): 657-70) can be used in the present invention. Amino acid positions and complementarity determining regions (CDRs) and framework regions (FR) of a given antibody may be identified using either system. For example, EU heavy chain positions of 39, 44, 183, 356, 357, 370, 392, 399, and 409 are equivalent to AHo heavy chain positions 46, 51, 230, 484, 485, 501, 528, 535, and 551, respectively. Similarly, EU light chain positions 38, 100, and 176 are equivalent to AHO light chain positions 46 141, and 230, respectively. Tables 1, 2, and 3 below demonstrate the equivalence between numbering positions.

In one aspect, the present invention is directed to a CH3-containing molecule comprising (a) a first polypeptide comprising a CH3 domain and a negatively charged domain comprising at least four consecutive negatively charged amino acid residues; and (b) a second polypeptide comprising a CH3 domain and a positively charged domain comprising at least four consecutive positively charged amino acid residues.

In one embodiment, the CH3 domain and the negatively charged domain of the first polypeptide are positioned relative to each other in an N-terminal to C-terminal direction and the CH3 domain and the positively charged domain of the second polypeptide are positioned relative to each other in an N-terminal to C-terminal direction. In one embodiment, the first and second polypeptides each further comprise a CH2 domain. In one embodiment, the first and second polypeptides each further comprise a hinge domain. In one embodiment, the first and second polypeptides each comprise VH, CH1, hinge, CH2, and CH3 domains positioned relative to each other in an N-terminal to C-terminal direction.

In one embodiment, the molecule further comprises a third and a fourth polypeptide, wherein the third polypeptide comprises a first VL domain and the fourth polypeptide comprises a second VL domain. In one embodiment, the third polypeptide further comprises a first CL domain wherein the first VL and CL domains are positioned relative to each other within the third polypeptide in an N-terminal to C-terminal direction, and the fourth polypeptide further comprises a second CL domain, and wherein the second VL and CL domains are positioned relative to each other within the fourth polypeptide in an N-terminal to C-terminal direction.

Mutations of heavy and light chains can be introduced in order to facilitate proper pairing of heavy and light chains. In Tables 1, 2 and 3 below, LC-E will pair with HC-K while LC-K will pair with HC-E. The common negative charges found on LC-E and HC-E will repel these two chains away from each other. Similarly, common positive charges found on LC-K and HC-K will repel these two chains away from each other. Accordingly, pairing between LC-E and HC—K and pairing between LC-K and HC-E will be favored.

TABLE 1 v1

| Chain | Domain | Mutation | AHo # | EU # | Kabat # |
|---|---|---|---|---|---|
| LC-E | Constant | E | 230 | 176 | 176 |
| LC-K | Constant | K | 230 | 176 | 176 |
| HC-E | CH1 | E | 230 | 183 | 188 |
| HC-K | CH1 | K | 230 | 183 | 188 |

TABLE 2 v2

| Chain | Domain | Mutation | AHo # | EU # | Kabat # |
|---|---|---|---|---|---|
| LC-E | Variable | E | 46 | 38 | 38 |
|  | Constant | E | 230 | 176 | 176 |
| LC-K | Variable | K | 46 | 38 | 38 |
|  | Constant | K | 230 | 176 | 176 |
| HC-E | Variable | E | 46 | 39 | 39 |
|  | CH1 | E | 230 | 183 | 188 |
| HC-K | Variable | K | 46 | 39 | 39 |
|  | CH1 | K | 230 | 183 | 188 |

TABLE 3 v3

| Chain | Domain | Mutation | AHo # | EU # | Kabat # |
|---|---|---|---|---|---|
| LC-E | Variable | E | 141 | 100 | 100 |
|  | Constant | E | 230 | 176 | 176 |
| LC-K | Variable | K | 141 | 100 | 100 |
|  | Constant | K | 230 | 176 | 176 |

TABLE 3-continued v3

| Chain | Domain | Mutation | AHo # | EU # | Kabat # |
|---|---|---|---|---|---|
| HC-E | Variable | E | 51 | 44 | 44 |
|  | CH1 | E | 230 | 183 | 188 |
| HC-K | Variable | K | 51 | 44 | 44 |
|  | CH1 | K | 230 | 183 | 188 |

To facilitate the association of a particular heavy chain with its cognate light chain, both the heavy and light chains may contain complimentary amino acid substitutions. As used herein, "complimentary amino acid substitutions" refer to a substitution to a positively-charged amino acid in one chain paired with a negatively-charged amino acid substitution in the other chain. For example, in some embodiments, the heavy chain comprises at least one amino acid substitution to introduce a charged amino acid and the corresponding light chain comprises at least one amino acid substitution to introduce a charged amino acid, wherein the charged amino acid introduced into the heavy chain has the opposite charge of the amino acid introduced into the light chain. In certain embodiments, one or more positively-charged residues (e.g., lysine, histidine or arginine) can be introduced into a first light chain (LC1) and one or more negatively-charged residues (e.g., aspartic acid or glutamic acid) can be introduced into the companion heavy chain (HC1) at the binding interface of LC1/HC1, whereas one or more negatively-charged residues (e.g., aspartic acid or glutamic acid) can be introduced into a second light chain (LC2) and one or more positively-charged residues (e.g., lysine, histidine or arginine) can be introduced into the companion heavy chain (HC2) at the binding interface of LC2/HC2. The electrostatic interactions will direct the LC1 to pair with HC1 and LC2 to pair with HC2, as the opposite charged residues (polarity) at the interface attract. The heavy/light chain pairs having the same charged residues (polarity) at an interface (e.g. LC1/HC2 and LC2/HC1) will repel, resulting in suppression of the unwanted HC/LC pairings.

In these and other embodiments, the CH1 domain of the heavy chain or the CL domain of the light chain comprises an amino acid sequence differing from wild-type IgG amino acid sequence such that one or more positively-charged amino acids in wild-type IgG amino acid sequence is replaced with one or more negatively-charged amino acids. Alternatively, the CH1 domain of the heavy chain or the CL domain of the light chain comprises an amino acid sequence differing from wild-type IgG amino acid sequence such that one or more negatively-charged amino acids in wild-type IgG amino acid sequence is replaced with one or more positively-charged amino acids. In some embodiments, one or more amino acids in the CH1 domain of the first and/or second heavy chain in the heterodimeric antibody at an EU position selected from F126, P127, L128, A141, L145, K147, D148, H168, F170, P171, V173, Q175, S176, S183, V185 and K213 is replaced with a charged amino acid. In certain embodiments, a heavy chain residue for substitution with a negatively- or positively-charged amino acid is S183 (EU numbering system). In some embodiments, S183 is substituted with a positively-charged amino acid. In alternative embodiments, S183 is substituted with a negatively-charged amino acid. For instance, in one embodiment, S183 is substituted with a negatively-charged amino acid (e.g.

S183E) in the first heavy chain, and S183 is substituted with a positively-charged amino acid (e.g. S183K) in the second heavy chain.

In embodiments in which the light chain is a kappa light chain, one or more amino acids in the CL domain of the first and/or second light chain in the heterodimeric antibody at a position (EU numbering in a kappa light chain) selected from F116, F118, S121, D122, E123, Q124, S131, V133, L135, N137, N138, Q160, S162, T164, S174 and S176 is replaced with a charged amino acid. In embodiments in which the light chain is a lambda light chain, one or more amino acids in the CL domain of the first and/or second light chain in the heterodimeric antibody at a position (EU numbering in a lambda chain) selected from T116, F118, S121, E123, E124, K129, T131, V133, L135, S137, E160, T162, S165, Q167, A174, S176 and Y178 is replaced with a charged amino acid. In some embodiments, a residue for substitution with a negatively- or positively-charged amino acid is S176 (EU numbering system) of the CL domain of either a kappa or lambda light chain. In certain embodiments, S176 of the CL domain is replaced with a positively-charged amino acid. In alternative embodiments, S176 of the CL domain is replaced with a negatively-charged amino acid. In one embodiment, S176 is substituted with a positively-charged amino acid (e.g. S176K) in the first light chain, and S176 is substituted with a negatively-charged amino acid (e.g. S176E) in the second light chain.

In addition to or as an alternative to the complimentary amino acid substitutions in the CH1 and CL domains, the variable regions of the light and heavy chains in the heterodimeric antibody may contain one or more complimentary amino acid substitutions to introduce charged amino acids. For instance, in some embodiments, the VH region of the heavy chain or the VL region of the light chain of a heterodimeric antibody comprises an amino acid sequence differing from wild-type IgG amino acid sequence such that one or more positively-charged amino acids in wild-type IgG amino acid sequence is replaced with one or more negatively-charged amino acids. Alternatively, the VH region of the heavy chain or the VL region of the light chain comprises an amino acid sequence differing from wild-type IgG amino acid sequence such that one or more negatively-charged amino acids in wild-type IgG amino acid sequence is replaced with one or more positively-charged amino acids.

V region interface residues (i.e., amino acid residues that mediate assembly of the VH and VL regions) within the VH region include EU positions 1, 3, 35, 37, 39, 43, 44, 45, 46, 47, 50, 59, 89, 91, and 93. One or more of these interface residues in the VH region can be substituted with a charged (positively- or negatively-charged) amino acid. In certain embodiments, the amino acid at EU position 39 in the VH region of the first and/or second heavy chain is substituted for a positively-charged amino acid, e.g., lysine. In alternative embodiments, the amino acid at EU position 39 in the VH1 region of the first and/or second heavy chain is substituted for a negatively-charged amino acid, e.g., glutamic acid. In some embodiments, the amino acid at EU position 39 in the VH region of the first heavy chain is substituted for a negatively-charged amino acid (e.g. G39E), and the amino acid at EU position 39 in the VH region of the second heavy chain is substituted for a positively-charged amino acid (e.g. G39K). In some embodiments, the amino acid at EU position 44 in the VH region of the first and/or second heavy chain is substituted for a positively-charged amino acid, e.g., lysine. In alternative embodiments, the amino acid at EU position 44 in the VH region of the first and/or second heavy chain is substituted for a negatively-charged amino acid, e.g., glutamic acid. In certain embodiments, the amino acid at EU position 44 in the VH region of the first heavy chain is substituted for a negatively-charged amino acid (e.g. G44E), and the amino acid at EU position 44 in the VH region of the second heavy chain is substituted for a positively-charged amino acid (e.g. G44K).

V region interface residues (i.e., amino acid residues that mediate assembly of the VH and VL regions) within the VL region include EU positions 32, 34, 35, 36, 38, 41, 42, 43, 44, 45, 46, 48, 49, 50, 51, 53, 54, 55, 56, 57, 58, 85, 87, 89, 90, 91, and 100. One or more interface residues in the VL region can be substituted with a charged amino acid, preferably an amino acid that has an opposite charge to those introduced into the VH region of the cognate heavy chain. In some embodiments, the amino acid at EU position 100 in the VL region of the first and/or second light chain is substituted for a positively-charged amino acid, e.g., lysine. In alternative embodiments, the amino acid at EU position 100 in the VL region of the first and/or second light chain is substituted for a negative-charged amino acid, e.g., glutamic acid. In certain embodiments, the amino acid at EU position 100 in the VL region of the first light chain is substituted for a positively-charged amino acid (e.g. G100K), and the amino acid at EU position 100 in the VL region of the second light chain is substituted for a negatively-charged amino acid (e.g. G100E).

Additionally, or alternatively, correct heavy-light chain pairing may be facilitated by swapping the CH1 and CL domains in the carboxyl-terminal Fab binding domain. By way of example, the first polypeptide, which is fused to the carboxyl terminus of the heavy chain, may comprise a VL domain and CH1 domain from the second antibody, and the second polypeptide may comprise a VH domain and CL domain from the second antibody. In another embodiment, the first polypeptide, which is fused to the carboxyl terminus of the heavy chain, may comprise a VH domain and a CL domain from the second antibody, and the second polypeptide may comprise a VL domain and CH1 domain from the second antibody.

The heavy chain constant regions or the Fc regions of the bispecific antigen binding proteins described herein may comprise one or more amino acid substitutions that affect the glycosylation and/or effector function of the antigen binding protein. One of the functions of the Fc region of an immunoglobulin is to communicate to the immune system when the immunoglobulin binds its target. This is commonly referred to as "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc region to Fc receptors on the surface of cells of the immune system. CDC is mediated through the binding of the Fc with proteins of the complement system, e.g., C1q. In some embodiments, the bispecific antigen binding proteins of the invention comprise one or more amino acid substitutions in the constant region to enhance effector function, including ADCC activity, CDC activity, ADCP activity, and/or the clearance or half-life of the antigen binding protein. Exemplary amino acid substitutions (EU numbering) that can enhance effector function include, but are not limited to, E233L, L234I, L234Y, L235S, G236A, S239D, F243L, F243V, P247I, D280H, K290S, K290E, K290N, K290Y, R292P, E294L, Y296W, S298A, S298D, S298V, S298G, S298T, T299A, Y300L, V305I, Q311M, K326A, K326E, K326W, A330S, A330L, A330M, A330F, I332E, D333A, E333S, E333A, K334A, K334V, A339D, A339Q, P396L, or combinations of any of the foregoing.

In other embodiments, the bispecific antigen binding proteins of the invention comprise one or more amino acid substitutions in the constant region to reduce effector function. Exemplary amino acid substitutions (EU numbering) that can reduce effector function include, but are not limited to, C220S, C226S, C229S, E233P, L234A, L234V, V234A, L234F, L235A, L235F, G237A, P238S, S267E, H268Q, N297A, N297G, V309L., E318A, L328F, A330S, A331S, P331S or combinations of any of the foregoing.

Glycosylation can contribute to the effector function of antibodies, particularly IgG1 antibodies. Thus, in some embodiments, the bispecific antigen binding proteins of the invention may comprise one or more amino acid substitutions that affect the level or type of glycosylation of the binding proteins. Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

In certain embodiments, glycosylation of the bispecific antigen binding proteins described herein is increased by adding one or more glycosylation sites, e.g., to the Fc region of the binding protein. Addition of glycosylation sites to the antigen binding protein can be conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

The invention also encompasses production of bispecific antigen binding protein molecules with altered carbohydrate structure resulting in altered effector activity, including antigen binding proteins with absent or reduced fucosylation that exhibit improved ADCC activity. Various methods are known in the art to reduce or eliminate fucosylation. For example, ADCC effector activity is mediated by binding of the antibody molecule to the FcγRIII receptor, which has been shown to be dependent on the carbohydrate structure of the N-linked glycosylation at the N297 residue of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (see Yamane-Ohnuki et al., Biotechnol Bioeng. 87 (5): 614-22, 2004). Similar effects can be accomplished through decreasing the activity of alpha-1,6-fucosyl transferase enzyme or other enzymes in the fucosylation pathway, e.g., through siRNA or antisense RNA treatment, engineering cell lines to knockout the enzyme(s), or culturing with selective glycosylation inhibitors (see Rothman et al., Mol Immunol. 26 (12): 1113-23, 1989). Some host cell strains, e.g. Lec13 or rat hybridoma YB2/0 cell line naturally produce antibodies with lower fucosylation levels (see Shields et al., J Biol Chem. 277 (30): 26733-40, 2002 and Shinkawa et al., J Biol Chem. 278 (5): 3466-73, 2003). An increase in the level of bisected carbohydrate, e.g. through recombinantly producing antibody in cells that overexpress GnTIII enzyme, has also been determined to increase ADCC activity (see Umana et al., Nat Biotechnol. 17 (2): 176-80, 1999).

In other embodiments, glycosylation of the bispecific antigen binding proteins described herein is decreased or eliminated by removing one or more glycosylation sites, e.g., from the Fc region of the binding protein. Amino acid substitutions that eliminate or alter N-linked glycosylation sites can reduce or eliminate N-linked glycosylation of the antigen binding protein. In certain embodiments, the bispecific antigen binding proteins described herein comprise a mutation at position N297 (EU numbering), such as N297Q, N297A, or N297G. In one particular embodiment, the bispecific antigen binding proteins of the invention comprise a Fc region from a human IgG1 antibody with a N297G mutation. To improve the stability of molecules comprising a N297 mutation, the Fc region of the molecules may be further engineered. For instance, in some embodiments, one or more amino acids in the Fc region are substituted with cysteine to promote disulfide bond formation in the dimeric state. Residues corresponding to V259, A287, R292, V302, L306, V323, or I332 (EU numbering) of an IgG1 Fc region may thus be substituted with cysteine. In one embodiment, specific pairs of residues are substituted with cysteine such that they preferentially form a disulfide bond with each other, thus limiting or preventing disulfide bond scrambling. In certain embodiments pairs include, but are not limited to, A287C and L306C, V259C and L306C, R292C and V302C, and V323C and I332C. In particular embodiments, the bispecific antigen binding proteins described herein comprise a Fc region from a human IgG1 antibody with mutations at R292C and V302C. In such embodiments, the Fc region may also comprise a N297G mutation.

Modifications of the bispecific antigen binding proteins of the invention to increase serum half-life also may be desirable, for example, by incorporation of or addition of a salvage receptor binding epitope (e.g., by mutation of the appropriate region or by incorporating the epitope into a peptide tag that is then fused to the antigen binding protein at either end or in the middle, e.g., by DNA or peptide synthesis; see, e.g., WO96/32478) or adding molecules such as PEG or other water soluble polymers, including polysaccharide polymers. The salvage receptor binding epitope preferably constitutes a region wherein any one or more amino acid residues from one or two loops of a Fc region are transferred to an analogous position in the antigen binding protein. In one embodiment, three or more residues from one or two loops of the Fc region are transferred. In one embodiment, the epitope is taken from the CH2 domain of the Fc region (e.g., an IgG Fc region) and transferred to the CH1, CH3, or VH region, or more than one such region, of the antigen binding protein. Alternatively, the epitope is taken from the CH2 domain of the Fc region and transferred to the CL region or VL region, or both, of the antigen binding protein. See International applications WO 97/34631 and WO 96/32478 for a description of Fc variants and their interaction with the salvage receptor.

In one embodiment, the negatively charged domain comprises at least two, at least three, at least four, at least five, at least six, or at least seven consecutive negatively charged amino acid residues and the positively charged domain comprises at least two, at least three, at least four, at least five, at least six, or at least seven consecutive positively charged amino acid residues.

In one embodiment, the negatively charged amino acid residues are aspartic acid residues and the positively charged amino acid residues are selected from the group consisting of lysine, arginine, and histidine residues. In one embodiment, the negatively charged amino acid residues are aspartic acid residues and the positively charged amino acid residues are lysine residues.

In one embodiment, the negatively charged amino acid residues are glutamic acid residues and the positively charged amino acid residues are selected from the group consisting of lysine, arginine, and histidine residues.

In one embodiment, the first polypeptide further comprises a linker sequence covalently attached to the C-terminus of the CH3 domain and the linker is attached to the N-terminus of the negatively charged domain; and wherein the second polypeptide further comprises a linker sequence covalently attached to the C-terminus of the CH3 domain and the linker is attached to the N-terminus of the positively charged domain.

In one embodiment, the linker of the first polypeptide is the same as the linker of the second polypeptide.

In one embodiment, the linker can be cleaved by an enzyme. In one embodiment, the enzyme is selected from the group consisting of sortase A, sortase B, sortase C, sortase D, sortase E, and sortase F.

In one embodiment, the linker comprises the amino acid sequence of SEQ ID NO: 1 (LPETGGEEST); SEQ ID NO: 2 (LPXTG, wherein X can be any amino acid); SEQ ID NO: 3 (LPETG); SEQ ID NO: 4 (LPETGG); SEQ ID NO: 5 (LPXTA, wherein X can be any amino acid): SEQ ID NO: 6 (NPX [T/S] [N/G/S], wherein X can be any amino acid); SEQ ID NO: 7 (IPXTG, wherein X can be any amino acid); and SEQ ID NO: 8 (LAXTG, wherein X can be any amino acid).

In one embodiment, either the first polypeptide, the second polypeptide, or both further comprises a purification tag attached to its C-terminus.

In one embodiment, the purification tag is selected from the group consisting of a his-tag, a strep-tag, a flag-tag, a T7-tag, a V5-peptide-tag, a GST-tag, a CBP-tag, a MBP-tag and a c-Myc-tag. In one embodiment, the purification tag is a his-tag comprising at least five consecutive histidine amino acid residues.

In one embodiment, the first polypeptide comprises the amino acid sequence of SEQ ID NO: 9 (LPETGGEESTDDDDDDD) and the second polypeptide comprises the amino acid sequence of SEQ ID NO: 10 (LPETGGEESTKKKKKKKHHHHHH).

In one embodiment, the first polypeptide comprises the amino acid sequence of SEQ ID NO: 11 (LPETGGEESTDDDDDDDHHHHHH) and the second polypeptide comprises the amino acid sequence of SEQ ID NO: 12 (LPETGGEESTKKKKKKK).

In one aspect the present invention is directed to a multi-specific antibody comprising a first heavy chain polypeptide, a first light chain polypeptide, a second heavy chain polypeptide, and a second light chain polypeptide, wherein
the first heavy chain polypeptide comprises a CH3 domain and a negatively charged domain comprising at least four consecutive negatively charged amino acid residues and the first heavy chain polypeptide and the first light chain polypeptide bind to a first antigen; and
the second heavy chain polypeptide comprises a CH3 domain and a positively charged domain comprising at least four consecutive positively charged amino acid residues and the second heavy chain polypeptide and the second light chain polypeptide bind to a second antigen.

In one embodiment, the multi-specific antibody is expressed by a mammalian cell. In one embodiment, the mammalian cell is a HEK or a CHO cell.

In one aspect, the present invention is directed to a method of producing a multi-specific antibody, the method comprising the step of culturing a cell comprising a vector encoding a multi-specific antibody of the present invention in a culture medium.

In one embodiment, the method further comprises recovering the multi-specific antibody from the cell or the culture medium.

In one aspect, the present invention is directed to a method for preparing an antibody conjugate, the method comprising the steps of;
a) providing a multi-specific antibody; and
b) treating the antibody with a sortase enzyme in the presence a synthetic molecule, wherein the molecule comprises an gly-gly-gly sequence. In one embodiment, step b) is performed using a synthetic molecule: antibody molar ratio of about 2 to about 1000.

EXAMPLES

Production of conjugated bispecific antibodies through sortase cleavable C-terminal charge-paired tags
Construct Design:
Heavy Chain: Heavy Chain (HC: HC) Pairing:

Constructs for two model bispecific antibodies, TNFα/TL1A and PAC1/CGRP1 were designed. TNFα and PAC1 heavy chains were both extended to contain a sortase recognition sequence (LPETG (SEQ ID NO: 13)), a short sortase-friendly linker (GEEST (SEQ ID NO:14)), and 7 aspartic acid residues to generate a 17 residue C-terminal extension: LPETGGEESTDDDDDDD (SEQ ID NO:15).

TL1A and CGRP1 heavy chains were both extended to contain a sortase recognition sequence (LPETG (SEQ ID NO:13)), a short sortase-friendly linker (GEEST (SEQ ID NO:14)), 7 lysine residues, and 6 histidine residues to generate a 23 residue C-terminal extension.

```
                                          (SEQ ID NO: 16)
LPETGGEESTKKKKKKKHHHHHH
```

These terminal extensions were added to the existing antibody constructs via site directed mutagenesis using standard methods (Carrigan et al. 2011).

Heavy chain: Light chain (HC: LC) pairing: Correct HC: LC pairing was designed according to (Liu et al. 2015; Florio et al. 2016).

Full gene sequences for TNFα/TL1A bispecific:
TNFα heavy chain:

```
                                          (SEQ ID NO: 17)
MRVPAQLLGLLLLWLRGARCEVQLVESGGGLVQPGGSLRLSCAASGYVFT

DYGMNWVRKAPGKGLEWMAWINTYIGEPIYADSVKGRFTISRDTSKSTAY

LQMNSLRAEDTAVYYCARGYRSYAMDYWGQGTLVTVSSASTKGPSVFPLA
```

PSSKSISGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYV
DGVEVHNAKTKPCEEQYGSTYRCVSVLTVLHQDWLNGKEYKCKVSNKALP
APIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMH
EALHNHYTQKSLSLSPGLPETGGEESTDDDDDDD.

TNFα light chain:

(SEQ ID NO: 18)
MDMRVPAQLLGLLLLWLRGARCDIQMTQSPSSLSASVGDRVTITCKASQN
VGTNVAWYQEKPGKAPKALIYSASFLYSGVPSRFSGSGSGTDFTLTISSL
QPEDFATYYCQQYNIYPLTFGQGTKVEIKRTVAAPSVFIFPPSDEQLKSG
TASVVCLLNNFYPREAKVQWKVDNALQSGNSQESVTEQDSKDSTYSLEST
LTLSKADYEKHKVYACEVTHQGLSSPVTKSFNRGEC.

TL1A heavy chain:

(SEQ ID NO: 19)
MKHLWFFLLLVAAPRWVLSQVQLQQSGAGLLKPSETLSLTCAVHGGSFSG
YYWNWIREPPGKGLEWIGEINHAGNTNYNPSLKSRVTISLDTSKNQFSLT
LTSVTAADTAVYYCARGYCRSTTCYFDYWGQGTLVTVSSASTKGPSVFPL
APSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWY
VDGVEVHNAKTKPCEEQYGSTYRCVSVLTVLHQDWLNGKEYKCKVSNKAL
PAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVM
HEALHNHYTQKSLSLSPGLPETGGEESTKKKKKKKHHHHHH.

TL1A light chain:

(SEQ ID NO: 20)
METPAQLLFLLLLWLPDTTGEIVLTQSPGTLSLSPGERATLSCRASQSVR
SSYLAWYQKKPGQAPRLLIYGASSRATGIPDRFSGSGSGTDFTLTISRLE
PEDFAVYYCQQYGSSPTFGQGTRLEIKRTVAAPSVFIFPPSDEQLKSGTA
SVVCLLNNFYPREAKVQWKVDNALQSGNSQESVTEQDSKDSTYSLKSTLT
LSKADYEKHKVYACEVTHQGLSSPVTKSFNRGEC.

Full gene sequences for PAC1/CGRP1:
PAC1 heavy chain:

(SEQ ID NO: 21)
MRVPAQLLGLLLLWLRGARCQVQLVESGAEVVKPGASVKVSCKASGFTFS
RFAMHWVRQAPGQGLEWMGVISYDGGNKYYAESVKGRVTMTRDTSTSTLY
MELSSLRSEDTAVYYCARGYDVLTGYPDYWGQGTLVTVSSASTKGPSVFP
LAPSSKSISGGTAALGCLVKDYFPEPVTVSWNSGALTSGVHTFPAVLQSS
GLYSLSSVVTVPSSSLGTQTYICNVNHKPSNTKVDKKVEPKSCDKTHTCP
PCPAPELLGGPSVFLFPPKPKDTLMISRTPEVTCVVVDVSHEDPEVKFNW
YVDGVEVHNAKTKPCEEQYGSTYRCVSVLTVLHQDWLNGKEYKCKVSNKA
LPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSV
MHEALHNHYTQKSLSLSPGLPETGGEESTDDDDDDD.

PAC1 light chain:

(SEQ ID NO: 22)
MDMRVPAQLLGLLLLWLRGARCDIQLTQSPSFLSASVGDRVTITCRASQS
IGRSLHWYQQKPGKAPKLLIKYASQSLSGVPSRFSGSGSGTEFTLTISSL
QPEDFATYYCHQSSRLPFTFGPGTKVDIKRTVAAPSVFIFPPSDEQLKSG
TASVVCLLNNFYPREAKVQWKVDNALQSGNSQESVTEQDSKDSTYSLEST
LTLSKADYEKHKVYACEVTHQGLSSPVTKSFNRGEC.

CGRP1 heavy chain:

(SEQ ID NO: 23)
MRVPAQLLGLLLLWLRGARCQVQLVESGGGVVQPGRSLRLSCAASGFTFS
SFGMHWVRQAPGKGLEWVAVISFDGSIKYSVDSVKGRFTISRDNSKNTLF
LQMNSLRAEDTAVYYCARDRLNYYESSGYYHYKYYGMAVWGQGTTVTVSS
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVICVVVDVS
HEDPEVKFNWYVDGVEVHNAKTKPCEEQYGSTYRCVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGLPETGGEESTKKKKKKKHHHH
HH.

CGRP1 light chain:

(SEQ ID NO: 24)
MAWALLLLTLLTQGTGSWAQSVLTQPPSVSAAPGQKVTISCSGSSSNIGN
NYVSWYQQLPGTAPKLLIYDNNKRPSGIPDRFSGSKSGTSATLGITGLQT
GDEADYYCGTWDSRLSAVVFGGGTKLTVLGQPKANPTVTLFPPSSEELQA
NKATLVCLISDFYPGAVTVAWKADGSPVKAGVETTKPSKQSNNKYAAKSY
LSLTPEQWKSHRSYSCQVTHEGSTVEKTVAPTECS.

Cloning

Genes for all heavy chains were cloned into vector pTT5.2 using the Golden Gate method (Engler et al. 2008), while genes for TNFα and TL1A light chains were cloned into pTT5.1 and PAC1 and CGRP1 light chains were cloned into pTT5 using Transient HEK 293-6e Cell Expression HEK 293-6e cells were grown to a VCD of 1.5e6 in FreeStyle F-17+0.1% (10 mL/L of 10%) Kolliphor P188+ 500 ML/L G418+6 mM (30 ml/L) L-glutamine at 36° C., 5% CO2, shaking in flasks at 150 rpm, before addition of a transfection complex consisting of FreeStyle F-17 media (10% of the final culture volume), 0.5 mg/L transfection DNA (1.25 g/L per chain), 2.0 mg/L PEI Max (pH 7.0) (Longo et al. 2013). Three hours after initial transfection, the cultures were fed with 0.5% w/v final concentration Yeastolate, and 2.5 g/L glucose.

Transiently transfected cells were allowed to incubate at 37° C., 5% CO2, shaking in flasks at 150 rpm for 7 days before harvesting by centrifugation at 4000 RPM for 10 mins. Conditioned media from each harvest was then collected and vacuum filtered through 0.22 µm bottle-top filters.

Purification

The antibodies were purified from conditioned media by ProA capture over HiTrap ProA HP resin (GE), and eluted in 100 mM Sodium Acetate pH 3.6. The $10^{-20}$ ml of ProA column eluate was adjusted to pH 5.0 by addition of 100-600 µl of 1M TRIS-HCl PH 9, and elution fractions were pooled and diluted 2-fold to reduce conductivity in preparation for loading onto the cation exchange column. The diluted ProA eluate was loaded onto a HiTrap SP column (GE) which was pre-equilibrated in 20 mM sodium acetate pH 5.0 and eluted by a linear gradient of o to 1M NaCl over 20 column volumes. The highly charged C-terminal extensions allowed base-line separation between the desired bispecific heterodimeric antibodies (75-85% of material generated) from mono-specific homodimeric antibody contaminants. CEX eluates were buffer exchanged into 10 mM sodium acetate+9% Sucrose pH 5 through serial concentration and dilution in a 15 ml. 30,000 MWCO centrifugal filter (Millipore) until a dilution factor of >50,000 was achieved.

Sortase Cleavage Reaction

Sortase cleavage reactions (Jacobitz et al. 2017; Ton-That, H., Mazmanian, S. K., Alksne, L., and Schneewind 2000; Clancy et al. 2010) to remove charge-paired tags via SrtA-mediated hydrolysis were conducted using 10 UM bispecific antibody, 20 uM SrtA2.0 (123 Bio) in 50 mM TRIS-HCl, at pH 5 (low pH was chosen specifically here to reduce formation of unwanted SrtA catalyzed isopeptide bond formation to Lys sidechains (Dasgupta et al. 2011) in polyK tail), for 24 hrs at 37° C. To our knowledge, removal of C terminal tags froa proteins by SrtA has not been reported anywhere. Furthermore, ours is the first report to show efficient SrtA cleavage of tags at pH 5.0. Normally SrtA mediated cleavage is performed at pH 7.0-8.5 Reaction progression was monitored by analytical CEX and the reaction products were verified by LCMS. After 24 hrs, reactions typically reached 85-90% completion. The fully de-tagged bispecific antibody could then be purified from the residual tagged molecules and the sortase by cation exchange chromatography (CEX) as described above.

Conjugation of Bispecific Antibodies with Molecular Entities

Sortase Transpeptidation Reactions

Sortase-mediated transpeptidation (Jacobitz et al. 2017; Levary et al. 2011; Mao et al. 2004; Ranganath Parthasarathy et al. 2007; Swee et al. 2013; Popp et al. 2007; Proft 2010; Spirig et al. 2011; Clancy et al. 2010; Antos et al. 2016) was employed to remove charge-paired tags and replace them with various synthetic molecules harboring a Gly3 sequence for sortase recognition, including Gly3, Gly3-biotin, Gly3-PEG20, Gly3-PEG20 kD, and Gly3-Alexa650. Reactions were conducted using $10^{-100}$ uM bispecific antibody at 0.1-10% w/w SrtA2.0 (123 Bio) with $10^{-100}$ fold molar excess of synthetic substrate: bispecific antibody, in 50 mM TRIS HCl, pH 6.5 for 24 hrs at 37° C. Progression of the reaction was monitored by analytical CEX and the products were analyzed by LCMS. Covalent attachment of fluorescent Gly3-Alexa650 probe via sortase-mediated transpeptidation was additionally verified by the appearance of a fluorescent band at the expected molecular weight via SDS-PAGE. After 24 hrs, reactions typically reached 85-99% yield. Transpeptidation products were purified from unreacted material and sortase through cation exchange chromatography as described above.

Generation of "Clickable" bispecific antibody via sortase-mediated transpeptidation with a non-canonical nucleophile and subsequent covalent attachment of fluorescent tag by click-chemistry Additional sortase mediated transpeptidation reactions were carried out to demonstrate the ability of sortase to covalently attach a non-canonical nucleophile (Ranganath Parthasarathy et al. 2007; Ton-That, H., Mazmanian, S. K., Alksne, L., and Schneewind 2000) containing a click-chemistry handle to the C-terminus of the bispecific. This clickable bispecific could subsequently be used to covalently attach a synthetic fluorophore via azide-DIBO click chemistry. 50 uM PAC1/CGRP1 bispecific antibody was incubated with 5 mM NH2-PEG3-N3 and 5 uM SrtA2.0 (123 Bio) in 25 mM TRIS HCl pH 6.5 for 24 hrs at 37° C. Reaction progress was monitored by CEX with a final yield of 87% after 24 hrs. Production of expected product species was verified by LCMS. Reaction products were removed from unreacted starting materials by CEX using the method detailed above. The resulting azide-functionalized bispecific was incubated at 1 uM with a 10 fold molar excess of DIBO-Alexa 488 for 24 hrs at room temperature, after which the covalent cross-linking between the newly formed bispecific with the fluorophore was confirmed by the appearance of a fluorescent band at the correct molecular weight on SDS-PAGE gel, and further verified by LCMS.

All patents, patent applications, patent application publications, and other publications cited or referred to in this specification are herein incorporated by reference to the same extent as if each independent patent, patent application, patent application publication or publication was specifically and individually indicated to be incorporated by reference.

REFERENCES

Antos, J.M., Truttmann, M.C. & Ploegh, H. L., 2016. Recent advances in sortase-catalyzed ligation methodology. Current Opinion in Structural Biology, 38, pp. 111-118. Available at: http://www.ncbi.nlm.nih.gov/pubmed/27318815 [Accessed Oct. 4, 2017].

Carrigan, P.E., Ballar, P. & Tuzmen, S., 2011. Site-Directed Mutagenesis. In J. K. DiStefano, ed. Disease Gene Identification: Methods and Protocols. Totowa, NJ: Humana Press, Totowa, NJ, pp. 107-124. Available at: http://link.springer.com/10.1007/978-1-61737-954-3 8 [Accessed Oct. 4, 2017].

Clancy, K.W., Melvin, J.A. & McCafferty, D. G., 2010. Sortase transpeptidases: insights into mechanism, substrate specificity, and inhibition. Biopolymers, 94 (4), pp. 385-396. Available at: http://www.ncbi.nlm.nih.gov/pubmed/20593474.

Dasgupta, S. et al., 2011. Isopeptide ligation catalyzed by quintessential sortase A: mechanistic cues from cyclic and branched oligomers of indolicidin. The Journal of biological chemistry, 286 (27), pp. 23996-4006. Available at: http://www.ncbi.nlm.nih.gov/pubmed/21566128 [Accessed Oct. 4, 2017].

Engler, C. et al., 2008. A One Pot, One Step, Precision Cloning Method with High Throughput Capability H. A.

El-Shemy, ed. PLOS ONE, 3 (11), p.c3647. Available at: http://dx.plos.org/10.1371/journal.pone.0003647 [Accessed Jul. 12, 2017].

Florio, M. et al., 2016. A bispecific antibody targeting sclerostin and DKK-1 promotes bone mass accrual and fracture repair. Nature communications, 7, p.11505. Available at: http://www.ncbi.nlm.nih.gov/pubmed/27230681 [Accessed Oct. 4, 2017].

Jacobitz, A. W. et al., 2017. Sortase Transpeptidases: Structural Biology and Catalytic Mechanism. In Advances in Protein Chemistry and Structural Biology. Available at: http://www.sciencedirect.com/science/article/pii/S1876162317300391 [Accessed Jun. 13, 2017].

Levary, D. A. et al., 2011. Protein-Protein Fusion Catalyzed by Sortase A J. Najbauer, ed. PLOS ONE, 6 (4), p.e18342. Available at: http://dx.plos.org/10.1371/journal.pone.0018342 [Accessed Dec. 16, 2016].

Liu, Z. et al., 2015. A novel antibody engineering strategy for making monovalent bispecific heterodimeric IgG antibodies by electrostatic steering mechanism. The Journal of biological chemistry, 290 (12), pp. 7535-62. Available at: http://www.ncbi.nlm.nih.gov/pubmed/25583986 [Accessed Oct. 4, 2017].

Longo, P.A. et al., 2013. Transient mammalian cell transfection with polyethylenimine pp. 227-40. Available at: (PEI). Methods in enzymology, 529, http://www.ncbi.nlm.nih.gov/pubmed/24011049 [Accessed Jan. 3, 2017].

Mao, H. et al., 2004. Sortase-mediated protein ligation: a new method for protein engineering. Journal of the American Chemical Society, 126 (9), pp. 2670-1. Available at: http://www.ncbi.nlm.nih.gov/pubmed/14995162 [Accessed Jul. 1, 2015].

Popp, M. W. et al., 2007. Sortagging: a versatile method for protein labeling. Nature Chemical Biology, 3 (11), pp. 707-708. Available at: http://www.nature.com/doifinder/10.1038/nchembio.2007.31 [Accessed May 23, 2017].

Proft, T., 2010. Sortase-mediated protein ligation: an emerging biotechnology tool for protein modification and immobilisation. Biotechnology Letters, 32 (1), pp. 1-10. Available at: http://link.springer.com/article/10.1007/s10529-009-0116-0 [Accessed May 23, 2013].

Ranganath Parthasarathy, +, Shyamsundar Subramanian, t and & Eric T. Boder*, t,+, 2007. Sortase A as a Novel Molecular "Stapler" for Sequence-Specific Protein Conjugation.

Spirig, T., Weiner, E.M. & Clubb, R. T., 2011. Sortase enzymes in Gram-positive bacteria. Molecular microbiology, 82 (5), pp. 1044-59. Available at: http://www.ncbi.nlm.nih.gov/pubmed/22026821 [Accessed Dec. 20, 2012].

Swee, L. K. et al., 2013. Sortase-mediated modification of aDEC205 affords optimization of antigen presentation and immunization against a set of viral epitopes. Proceedings of the National Academy of Sciences of the United States of America, 110 (4), pp. 1428-33. Available at: http://www.ncbi.nlm.nih.gov/pubmed/23297227 [Accessed Dec. 16, 2016].

Ton-That, H., Mazmanian, S. K., Alksne, L., and Schneewind, O., 2000. Anchoring of Surface Proteins to the Cell Wall of *Staphylococcus aureus*. SORTASE CATALYZED IN VITRO TRANSPEPTIDATION REACTION USING LPXTG PEPTIDE AND NH2-GLY3 SUBSTRATES. Journal of Biological Chemistry, 275 (13), pp. 9876-9881. Available at: http://www.jbc.org/content/275/13/9876.full [Accessed Jun. 9, 2015].

What is claimed is:

1. A CH3-containing molecule comprising:
   (a) a first polypeptide comprising a CH3 domain and a negatively charged domain comprising at least six consecutive negatively charged amino acid residues; and
   (b) a second polypeptide comprising a CH3 domain and a positively charged domain comprising at least six consecutive positively charged amino acid residues;
   wherein the CH3 domain and the negatively charged domain of the first polypeptide are positioned relative to each other in an N-terminal to C-terminal direction and the CH3 domain and the positively charged domain of the second polypeptide are positioned relative to each other in an N-terminal to C-terminal direction;
   wherein the first polypeptide comprises the amino acid sequence of SEQ ID NO: 9 (LPETG-GEESTDDDDDDD) and the second polypeptide comprises the amino acid sequence of SEQ ID NO: 10 (LPETGGEESTKKKKKKKHHHHHH).

2. A CH3-containing molecule comprising:
   (a) a first polypeptide comprising a CH3 domain and a negatively charged domain comprising at least six consecutive negatively charged amino acid residues; and
   (b) a second polypeptide comprising a CH3 domain and a positively charged domain comprising at least six consecutive positively charged amino acid residues;
   wherein the CH3 domain and the negatively charged domain of the first polypeptide are positioned relative to each other in an N-terminal to C-terminal direction and the CH3 domain and the positively charged domain of the second polypeptide are positioned relative to each other in an N-terminal to C-terminal direction;
   wherein the first polypeptide comprises the amino acid sequence of SEQ ID NO: 11 (LPETG-GEESTDDDDDDDHHHHHH) and the second polypeptide comprises the amino acid sequence of SEQ ID NO: 12 (LPETGGEESTKKKKKKK).

3. A multi-specific antibody comprising a first heavy chain polypeptide, a first light chain polypeptide, a second heavy chain polypeptide, and a second light chain polypeptide, wherein the first heavy chain polypeptide comprises a CH3 domain and a negatively charged domain comprising at least six consecutive negatively charged amino acid residues and the first heavy chain polypeptide and the first light chain polypeptide bind to a first antigen; and the second heavy chain polypeptide comprises a CH3 domain and a positively charged domain comprising at least six consecutive positively charged amino acid residues and the second heavy chain polypeptide and the second light chain polypeptide bind to a second antigen;

wherein the CH3 domain and the negatively charged domain of the first heavy chain polypeptide are positioned relative to each other in an N-terminal to C-terminal direction and the CH3 domain and the positively charged domain of the second heavy chain polypeptide are positioned relative to each other in an N-terminal to C-terminal direction;

wherein the first heavy chain polypeptide further comprises a linker sequence covalently attached to the C-terminus of the CH3 domain and the linker is attached to the N-terminus of the negatively charged domain;

wherein the second heavy chain polypeptide further comprises a linker sequence covalently attached to the C-terminus of the CH3 domain and the linker is attached to the N-terminus of the positively charged domain; and wherein the first heavy chain polypeptide comprises the amino acid sequence of SEQ ID NO: 11 (LPETG-GEESTDDDDDDDHHHHHH) and the second heavy chain polypeptide comprises the amino acid sequence of SEQ ID NO: 12 (LPETGGEESTKKKKKKK).

4. A multi-specific antibody comprising a first heavy chain polypeptide, a first light chain polypeptide, a second heavy chain polypeptide, and a second light chain polypeptide, wherein the first heavy chain polypeptide comprises a CH3 domain and a negatively charged domain comprising at least six consecutive negatively charged amino acid residues and the first heavy chain polypeptide and the first light chain polypeptide bind to a first antigen; and the second heavy chain polypeptide comprises a CH3 domain and a positively charged domain comprising at least six consecutive positively charged amino acid residues and the second heavy chain polypeptide and the second light chain polypeptide bind to a second antigen;

wherein the CH3 domain and the negatively charged domain of the first heavy chain polypeptide are positioned relative to each other in an N-terminal to C-terminal direction and the CH3 domain and the positively charged domain of the second heavy chain polypeptide are positioned relative to each other in an N-terminal to C-terminal direction;

wherein the first heavy chain polypeptide further comprises a linker sequence covalently attached to the C-terminus of the CH3 domain and the linker is attached to the N-terminus of the negatively charged domain;

wherein the second heavy chain polypeptide further comprises a linker sequence covalently attached to the C-terminus of the CH3 domain and the linker is attached to the N-terminus of the positively charged domain; and wherein the first heavy chain polypeptide comprises the amino acid sequence of SEQ ID NO: 9 (LPETG-GEESTDDDDDD) and the second heavy chain polypeptide comprises the amino acid sequence of SEQ ID NO: 10 (LPETGGEESTKKKKKKKHHHHHH).

5. A method of producing a multi-specific antibody, the method comprising the step of culturing a cell comprising a vector encoding the multi-specific antibody of claim 3 in a culture medium.

6. The method of claim 5, wherein the method further comprises recovering the multi-specific antibody from the cell or the culture medium.

7. The multi-specific antibody of claim 3, wherein either the first heavy chain polypeptide, the second heavy chain polypeptide, or both further comprises a purification tag attached to its C-terminus.

8. The multi-specific antibody of claim 7, where the purification tag is selected from the group consisting of a his-tag, a strep-tag, a flag-tag, a T7-tag, a V5-peptide-tag, a GST-tag, a CBP-tag, a MBP-tag and a c-Myc-tag.

9. The multi-specific antibody of claim 8, where the purification tag is a his-tag comprising at least five consecutive histidine amino acid residues.

10. The multi-specific antibody of claim 3, wherein the multi-specific antibody is expressed by a mammalian cell.

11. The multi-specific antibody of claim 10, wherein the mammalian cell is a HEK or a CHO cell.

12. A method of producing a multi-specific antibody, the method comprising the step of culturing a cell comprising a vector encoding the multi-specific antibody of claim 4 in a culture medium.

13. The method of claim 12, wherein the method further comprises recovering the multi-specific antibody from the cell or the culture medium.

* * * * *

SEQUENCE LISTING

```
<160> NUMBER OF SEQ ID NOS: 24

<210> SEQ ID NO 1
<211> LENGTH: 10
<212> TYPE: PRT
<213> ORGANISM: ARTIFICIAL SEQUENCE
<220> FEATURE:
<223> OTHER INFORMATION: LINKER SEQUENCE

<400> SEQUENCE: 1

Leu Pro Glu Thr Gly Gly Glu Glu Ser Thr
1               5                   10

<210> SEQ ID NO 2
<211> LENGTH: 5
<212> TYPE: PRT
<213> ORGANISM: ARTIFICIAL SEQUENCE
<220> FEATURE:
<223> OTHER INFORMATION: LINKER SEQUENCE
<220> FEATURE:
<221> NAME/KEY: MISC_FEATURE
<222> LOCATION: (3)..(3)
<223> OTHER INFORMATION: Xaa can be any amino acid

<400> SEQUENCE: 2

Leu Pro Xaa Thr Gly
1               5

<210> SEQ ID NO 3
<211> LENGTH: 5
<212> TYPE: PRT
<213> ORGANISM: ARTIFICIAL SEQUENCE
<220> FEATURE:
```

```
<223> OTHER INFORMATION: LINKER SEQUENCE

<400> SEQUENCE: 3

Leu Pro Glu Thr Gly
1               5

<210> SEQ ID NO 4
<211> LENGTH: 6
<212> TYPE: PRT
<213> ORGANISM: ARTIFICIAL SEQUENCE
<220> FEATURE:
<223> OTHER INFORMATION: LINKER SEQUENCE

<400> SEQUENCE: 4

Leu Pro Glu Thr Gly Gly
1               5

<210> SEQ ID NO 5
<211> LENGTH: 5
<212> TYPE: PRT
<213> ORGANISM: ARTIFICIAL SEQUENCE
<220> FEATURE:
<223> OTHER INFORMATION: LINKER SEQUENCE
<220> FEATURE:
<221> NAME/KEY: MISC_FEATURE
<222> LOCATION: (3)..(3)
<223> OTHER INFORMATION: Xaa can be any amino acid

<400> SEQUENCE: 5

Leu Pro Xaa Thr Ala
1               5

<210> SEQ ID NO 6
<211> LENGTH: 8
<212> TYPE: PRT
<213> ORGANISM: ARTIFICIAL SEQUENCE
<220> FEATURE:
<223> OTHER INFORMATION: LINKER SEQUENCE
<220> FEATURE:
<221> NAME/KEY: MISC_FEATURE
<222> LOCATION: (3)..(3)
<223> OTHER INFORMATION: Xaa can be any amino acid

<400> SEQUENCE: 6

Asn Pro Xaa Thr Ser Asn Gly Ser
1               5

<210> SEQ ID NO 7
<211> LENGTH: 5
<212> TYPE: PRT
<213> ORGANISM: ARTIFICIAL SEQUENCE
<220> FEATURE:
<223> OTHER INFORMATION: LINKER SEQUENCE
<220> FEATURE:
<221> NAME/KEY: MISC_FEATURE
<222> LOCATION: (3)..(3)
<223> OTHER INFORMATION: Xaa can be any amino acid

<400> SEQUENCE: 7

Ile Pro Xaa Thr Gly
1               5

<210> SEQ ID NO 8
<211> LENGTH: 5
<212> TYPE: PRT
<213> ORGANISM: ARTIFICIAL SEQUENCE
<220> FEATURE:
<223> OTHER INFORMATION: LINKER SEQUENCE
<220> FEATURE:
```

```
<221> NAME/KEY: MISC_FEATURE
<222> LOCATION: (3)..(3)
<223> OTHER INFORMATION: Xaa can be any amino acid

<400> SEQUENCE: 8

Leu Ala Xaa Thr Gly
1               5

<210> SEQ ID NO 9
<211> LENGTH: 17
<212> TYPE: PRT
<213> ORGANISM: ARTIFICIAL SEQUENCE
<220> FEATURE:
<223> OTHER INFORMATION: Polypeptide

<400> SEQUENCE: 9

Leu Pro Glu Thr Gly Gly Glu Glu Ser Thr Asp Asp Asp Asp Asp
1               5                   10                  15

Asp

<210> SEQ ID NO 10
<211> LENGTH: 23
<212> TYPE: PRT
<213> ORGANISM: ARTIFICIAL SEQUENCE
<220> FEATURE:
<223> OTHER INFORMATION: Polypeptide

<400> SEQUENCE: 10

Leu Pro Glu Thr Gly Gly Glu Glu Ser Thr Lys Lys Lys Lys Lys
1               5                   10                  15

Lys His His His His His His
            20

<210> SEQ ID NO 11
<211> LENGTH: 23
<212> TYPE: PRT
<213> ORGANISM: ARTIFICIAL SEQUENCE
<220> FEATURE:
<223> OTHER INFORMATION: Polypeptide

<400> SEQUENCE: 11

Leu Pro Glu Thr Gly Gly Glu Glu Ser Thr Asp Asp Asp Asp Asp
1               5                   10                  15

Asp His His His His His His
            20

<210> SEQ ID NO 12
<211> LENGTH: 17
<212> TYPE: PRT
<213> ORGANISM: ARTIFICIAL SEQUENCE
<220> FEATURE:
<223> OTHER INFORMATION: Polypeptide

<400> SEQUENCE: 12

Leu Pro Glu Thr Gly Gly Glu Glu Ser Thr Lys Lys Lys Lys Lys
1               5                   10                  15

Lys

<210> SEQ ID NO 13
<211> LENGTH: 5
<212> TYPE: PRT
<213> ORGANISM: ARTIFICIAL SEQUENCE
<220> FEATURE:
<223> OTHER INFORMATION: A sortase recognition heavy chain sequence
```

```
<400> SEQUENCE: 13

Leu Pro Glu Thr Gly
1               5

<210> SEQ ID NO 14
<211> LENGTH: 5
<212> TYPE: PRT
<213> ORGANISM: ARTIFICIAL SEQUENCE
<220> FEATURE:
<223> OTHER INFORMATION: A short sortase-friendly linker, heavy chain
      sequence

<400> SEQUENCE: 14

Gly Glu Glu Ser Thr
1               5

<210> SEQ ID NO 15
<211> LENGTH: 17
<212> TYPE: PRT
<213> ORGANISM: ARTIFICIAL SEQUENCE
<220> FEATURE:
<223> OTHER INFORMATION: C-terminal extension sequence

<400> SEQUENCE: 15

Leu Pro Glu Thr Gly Gly Glu Glu Ser Thr Asp Asp Asp Asp Asp Asp
1               5                   10                  15

Asp

<210> SEQ ID NO 16
<211> LENGTH: 23
<212> TYPE: PRT
<213> ORGANISM: ARTIFICIAL SEQUENCE
<220> FEATURE:
<223> OTHER INFORMATION: C-terminal extension sequence

<400> SEQUENCE: 16

Leu Pro Glu Thr Gly Gly Glu Glu Ser Thr Lys Lys Lys Lys Lys Lys
1               5                   10                  15

Lys His His His His His His
            20

<210> SEQ ID NO 17
<211> LENGTH: 484
<212> TYPE: PRT
<213> ORGANISM: ARTIFICIAL SEQUENCE
<220> FEATURE:
<223> OTHER INFORMATION: TNFalpha heavy chain sequence

<400> SEQUENCE: 17

Met Arg Val Pro Ala Gln Leu Leu Gly Leu Leu Leu Leu Trp Leu Arg
1               5                   10                  15

Gly Ala Arg Cys Glu Val Gln Leu Val Glu Ser Gly Gly Gly Leu Val
                20                  25                  30

Gln Pro Gly Gly Ser Leu Arg Leu Ser Cys Ala Ala Ser Gly Tyr Val
            35                  40                  45

Phe Thr Asp Tyr Gly Met Asn Trp Val Arg Lys Ala Pro Gly Lys Gly
        50                  55                  60

Leu Glu Trp Met Ala Trp Ile Asn Thr Tyr Ile Gly Glu Pro Ile Tyr
65                  70                  75                  80

Ala Asp Ser Val Lys Gly Arg Phe Thr Ile Ser Arg Asp Thr Ser Lys
                85                  90                  95

Ser Thr Ala Tyr Leu Gln Met Asn Ser Leu Arg Ala Glu Asp Thr Ala
```

```
            100             105             110
Val Tyr Tyr Cys Ala Arg Gly Tyr Arg Ser Tyr Ala Met Asp Tyr Trp
        115             120             125
Gly Gln Gly Thr Leu Val Thr Val Ser Ser Ala Ser Thr Lys Gly Pro
        130             135             140
Ser Val Phe Pro Leu Ala Pro Ser Ser Lys Ser Thr Ser Gly Gly Thr
145             150             155             160
Ala Ala Leu Gly Cys Leu Val Lys Asp Tyr Phe Pro Glu Pro Val Thr
                165             170             175
Val Ser Trp Asn Ser Gly Ala Leu Thr Ser Gly Val His Thr Phe Pro
                180             185             190
Ala Val Leu Gln Ser Ser Gly Leu Tyr Ser Leu Ser Ser Val Val Thr
                195             200             205
Val Pro Ser Ser Ser Leu Gly Thr Gln Thr Tyr Ile Cys Asn Val Asn
        210             215             220
His Lys Pro Ser Asn Thr Lys Val Asp Lys Lys Val Glu Pro Lys Ser
225             230             235             240
Cys Asp Lys Thr His Thr Cys Pro Pro Cys Pro Ala Pro Glu Leu Leu
                245             250             255
Gly Gly Pro Ser Val Phe Leu Phe Pro Pro Lys Pro Lys Asp Thr Leu
                260             265             270
Met Ile Ser Arg Thr Pro Glu Val Thr Cys Val Val Val Asp Val Ser
        275             280             285
His Glu Asp Pro Glu Val Lys Phe Asn Trp Tyr Val Asp Gly Val Glu
        290             295             300
Val His Asn Ala Lys Thr Lys Pro Cys Glu Glu Gln Tyr Gly Ser Thr
305             310             315             320
Tyr Arg Cys Val Ser Val Leu Thr Val Leu His Gln Asp Trp Leu Asn
                325             330             335
Gly Lys Glu Tyr Lys Cys Lys Val Ser Asn Lys Ala Leu Pro Ala Pro
                340             345             350
Ile Glu Lys Thr Ile Ser Lys Ala Lys Gly Gln Pro Arg Glu Pro Gln
        355             360             365
Val Tyr Thr Leu Pro Pro Ser Arg Glu Glu Met Thr Lys Asn Gln Val
        370             375             380
Ser Leu Thr Cys Leu Val Lys Gly Phe Tyr Pro Ser Asp Ile Ala Val
385             390             395             400
Glu Trp Glu Ser Asn Gly Gln Pro Glu Asn Asn Tyr Lys Thr Thr Pro
                405             410             415
Pro Val Leu Asp Ser Asp Gly Ser Phe Phe Leu Tyr Ser Lys Leu Thr
                420             425             430
Val Asp Lys Ser Arg Trp Gln Gln Gly Asn Val Phe Ser Cys Ser Val
        435             440             445
Met His Glu Ala Leu His Asn His Tyr Thr Gln Lys Ser Leu Ser Leu
        450             455             460
Ser Pro Gly Leu Pro Glu Thr Gly Gly Glu Glu Ser Thr Asp Asp Asp
465             470             475             480
Asp Asp Asp Asp

<210> SEQ ID NO 18
<211> LENGTH: 236
<212> TYPE: PRT
<213> ORGANISM: ARTIFICIAL SEQUENCE
<220> FEATURE:
```

<223> OTHER INFORMATION: TNFalpha light chain sequence

<400> SEQUENCE: 18

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asn Val Gly Thr Asn Val Ala Trp Tyr Gln Glu Lys Pro Gly Lys
    50                  55                  60

Ala Pro Lys Ala Leu Ile Tyr Ser Ala Ser Phe Leu Tyr Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ile Tyr Pro Leu Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Glu Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 19
<211> LENGTH: 491
<212> TYPE: PRT
<213> ORGANISM: ARTIFICIAL SEQUENCE
<220> FEATURE:
<223> OTHER INFORMATION: TL1A heavy chain sequence

<400> SEQUENCE: 19

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Gly Leu Leu Lys
            20                  25                  30

Pro Ser Glu Thr Leu Ser Leu Thr Cys Ala Val His Gly Gly Ser Phe
        35                  40                  45

Ser Gly Tyr Tyr Trp Asn Trp Ile Arg Glu Pro Pro Gly Lys Gly Leu
    50                  55                  60

Glu Trp Ile Gly Glu Ile Asn His Ala Gly Asn Thr Asn Tyr Asn Pro
65                  70                  75                  80

Ser Leu Lys Ser Arg Val Thr Ile Ser Leu Asp Thr Ser Lys Asn Gln
                85                  90                  95

Phe Ser Leu Thr Leu Thr Ser Val Thr Ala Ala Asp Thr Ala Val Tyr
            100                 105                 110
```

-continued

Tyr Cys Ala Arg Gly Tyr Cys Arg Ser Thr Thr Cys Tyr Phe Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Cys Glu Glu Gln Tyr Gly Ser
305                 310                 315                 320

Thr Tyr Arg Cys Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Leu Pro Glu Thr Gly Gly Glu Ser Thr Lys Lys
465                 470                 475                 480

Lys Lys Lys Lys His His His His His
                485                 490

<210> SEQ ID NO 20
<211> LENGTH: 234
<212> TYPE: PRT
<213> ORGANISM: ARTIFICIAL SEQUENCE
<220> FEATURE:

-continued

<223> OTHER INFORMATION: TL1A light chain sequence

<400> SEQUENCE: 20

```
Met Glu Thr Pro Ala Gln Leu Leu Phe Leu Leu Leu Trp Leu Pro
1               5                  10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Arg Ser Ser Tyr Leu Ala Trp Tyr Gln Lys Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Lys Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 21
<211> LENGTH: 486
<212> TYPE: PRT
<213> ORGANISM: ARTIFICIAL SEQUENCE
<220> FEATURE:
<223> OTHER INFORMATION: PAC1 heavy chain sequence

<400> SEQUENCE: 21

```
Met Arg Val Pro Ala Gln Leu Leu Gly Leu Leu Leu Trp Leu Arg
1               5                  10                  15

Gly Ala Arg Cys Gln Val Gln Leu Val Glu Ser Gly Ala Glu Val Val
            20                  25                  30

Lys Pro Gly Ala Ser Val Lys Val Ser Cys Lys Ala Ser Gly Phe Thr
        35                  40                  45

Phe Ser Arg Phe Ala Met His Trp Val Arg Gln Ala Pro Gly Gln Gly
    50                  55                  60

Leu Glu Trp Met Gly Val Ile Ser Tyr Asp Gly Gly Asn Lys Tyr Tyr
65                  70                  75                  80

Ala Glu Ser Val Lys Gly Arg Val Thr Met Thr Arg Asp Thr Ser Thr
                85                  90                  95

Ser Thr Leu Tyr Met Glu Leu Ser Ser Leu Arg Ser Glu Asp Thr Ala
            100                 105                 110
```

Val Tyr Tyr Cys Ala Arg Gly Tyr Asp Val Leu Thr Gly Tyr Pro Asp
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Gly
305                 310                 315                 320

Ser Thr Tyr Arg Cys Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Leu Pro Glu Thr Gly Gly Glu Glu Ser Thr Asp
465                 470                 475                 480

Asp Asp Asp Asp Asp
            485

<210> SEQ ID NO 22
<211> LENGTH: 236
<212> TYPE: PRT
<213> ORGANISM: ARTIFICIAL SEQUENCE
<220> FEATURE:

<223> OTHER INFORMATION: PAC1 light chain sequence

<400> SEQUENCE: 22

Met Asp Met Arg Val Pro Ala Gln Leu Leu Gly Leu Leu Leu Leu Trp
1               5                   10                  15

Leu Arg Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Gln Ser Ile Gly Arg Ser Leu His Trp Tyr Gln Gln Lys Pro Gly Lys
    50                  55                  60

Ala Pro Lys Leu Leu Ile Lys Tyr Ala Ser Gln Ser Leu Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys His Gln
            100                 105                 110

Ser Ser Arg Leu Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Glu Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 23
<211> LENGTH: 502
<212> TYPE: PRT
<213> ORGANISM: ARTIFICIAL SEQUENCE
<220> FEATURE:
<223> OTHER INFORMATION: CGRP1 heavy chain sequence

<400> SEQUENCE: 23

Met Arg Val Pro Ala Gln Leu Leu Gly Leu Leu Leu Leu Trp Leu Arg
1               5                   10                  15

Gly Ala Arg Cys Gln Val Gln Leu Val Glu Ser Gly Gly Gly Val Val
            20                  25                  30

Gln Pro Gly Arg Ser Leu Arg Leu Ser Cys Ala Ala Ser Gly Phe Thr
        35                  40                  45

Phe Ser Ser Phe Gly Met His Trp Val Arg Gln Ala Pro Gly Lys Gly
    50                  55                  60

Leu Glu Trp Val Ala Val Ile Ser Phe Asp Gly Ser Ile Lys Tyr Ser
65                  70                  75                  80

Val Asp Ser Val Lys Gly Arg Phe Thr Ile Ser Arg Asp Asn Ser Lys
                85                  90                  95

Asn Thr Leu Phe Leu Gln Met Asn Ser Leu Arg Ala Glu Asp Thr Ala
            100                 105                 110

Val Tyr Tyr Cys Ala Arg Asp Arg Leu Asn Tyr Tyr Glu Ser Ser Gly
            115                 120                 125

Tyr Tyr His Tyr Lys Tyr Tyr Gly Met Ala Val Trp Gly Gln Gly Thr
        130                 135                 140

Thr Val Thr Val Ser Ser Ala Ser Thr Lys Gly Pro Ser Val Phe Pro
145                 150                 155                 160

Leu Ala Pro Ser Ser Lys Ser Thr Ser Gly Gly Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
210                 215                 220

Ser Leu Gly Thr Gln Thr Tyr Ile Cys Asn Val Asn His Lys Pro Ser
225                 230                 235                 240

Asn Thr Lys Val Asp Lys Lys Val Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
290                 295                 300

Glu Val Lys Phe Asn Trp Tyr Val Asp Gly Val Glu Val His Asn Ala
305                 310                 315                 320

Lys Thr Lys Pro Cys Glu Glu Gln Tyr Gly Ser Thr Tyr Arg Cys Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
370                 375                 380

Pro Pro Ser Arg Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
450                 455                 460

Leu His Asn His Tyr Thr Gln Lys Ser Leu Ser Leu Ser Pro Gly Leu
465                 470                 475                 480

Pro Glu Thr Gly Gly Glu Glu Ser Thr Lys Lys Lys Lys Lys Lys Lys
                485                 490                 495

His His His His His His
            500

<210> SEQ ID NO 24
<211> LENGTH: 235

<212> TYPE: PRT
<213> ORGANISM: ARTIFICIAL SEQUENCE
<220> FEATURE:
<223> OTHER INFORMATION: CGRP1 light chain sequence

<400> SEQUENCE: 24

```
Met Ala Trp Ala Leu Leu Leu Leu Thr Leu Leu Thr Gln Gly Thr Gly
1               5                   10                  15

Ser Trp Ala Gln Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
            35                  40                  45

Gly Asn Asn Tyr Val Ser Trp Tyr Gln Gln Leu Pro Gly Thr Ala Pro
    50                  55                  60

Lys Leu Leu Ile Tyr Asp Asn Asn Lys Arg Pro Ser Gly Ile Pro Asp
65                  70                  75                  80

Arg Phe Ser Gly Ser Lys Ser Gly Thr Ser Ala Thr Leu Gly Ile Thr
                85                  90                  95

Gly Leu Gln Thr Gly Asp Glu Ala Asp Tyr Tyr Cys Gly Thr Trp Asp
            100                 105                 110

Ser Arg Leu Ser Ala Val Val Phe Gly Gly Thr Lys Leu Thr Val
            115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Lys Ser Tyr Leu Ser Leu Thr Pro Glu Gln Trp
            195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235
```